(12) United States Patent
Cully et al.

(10) Patent No.: US 11,052,230 B2
(45) Date of Patent: Jul. 6, 2021

(54) IMPLANTABLE ENCAPSULATION DEVICES

(71) Applicant: W. L. Gore & Associates, Inc., Newark, DE (US)

(72) Inventors: Edward H. Cully, Flagstaff, AZ (US); Edward Gunzel, Oxford, PA (US); Keith Knisley, Flagstaff, AZ (US); Greg Rusch, Newark, DE (US); Lauren Zambotti, Wilmington, DE (US)

(73) Assignee: W. L. Gore & Associates, Inc., Newark, DE (US)

( * ) Notice: Subject to any disclaimer, the term of this patent is extended or adjusted under 35 U.S.C. 154(b) by 316 days.

(21) Appl. No.: 15/806,054

(22) Filed: Nov. 7, 2017

(65) Prior Publication Data
US 2018/0126134 A1    May 10, 2018

Related U.S. Application Data

(60) Provisional application No. 62/419,204, filed on Nov. 8, 2016.

(51) Int. Cl.
*A61M 31/00*  (2006.01)
*A61F 2/02*  (2006.01)
(Continued)

(52) U.S. Cl.
CPC .......... *A61M 31/002* (2013.01); *A61F 2/022* (2013.01); *A61K 9/0092* (2013.01);
(Continued)

(58) Field of Classification Search
CPC ............ A61M 31/002; A61M 39/0247; A61M 39/04; A61M 2039/0264;
(Continued)

(56) References Cited

U.S. PATENT DOCUMENTS 5,324,518 A * 6/1994 Orth .................. A61M 39/0208
128/899
5,595,621 A    1/1997 Light et al.
(Continued)

FOREIGN PATENT DOCUMENTS

CN    1703175 A    11/2005
CN    101022769 A    8/2007
(Continued)

OTHER PUBLICATIONS

International Search Report PCT/US2017/060494 dated Jun. 6, 2018.

*Primary Examiner* — Bhisma Mehta
*Assistant Examiner* — James D Ponton
(74) *Attorney, Agent, or Firm* — Amy L. Miller

(57) ABSTRACT

The present disclosure relates to implantable encapsulation devices for housing a biological moiety or a therapeutic device that contains a biological moiety. Particularly, aspects of the present disclosure are directed to an implantable apparatus that includes a distal end, a proximal end, a manifold including at least one access port positioned either at the distal end or the proximal end, and a plurality of containment tubes affixed to the manifold and in fluid communication with the at least one access port. Additionally, the encapsulation device may contain a flush port and a tube that are fluidly connected to the manifold. The containment tubes may contain therein a biological moiety (e.g., cells) or a therapeutic device (e.g. a cell encapsulation member).

47 Claims, 41 Drawing Sheets

(51) Int. Cl.
*A61K 9/00* (2006.01)
*A61L 31/04* (2006.01)
*A61L 31/14* (2006.01)
*A61L 31/16* (2006.01)
*A61M 39/02* (2006.01)
*A61F 2/30* (2006.01)
*A61M 39/04* (2006.01)

(52) U.S. Cl.
CPC ............ *A61L 31/048* (2013.01); *A61L 31/14* (2013.01); *A61L 31/146* (2013.01); *A61L 31/148* (2013.01); *A61L 31/16* (2013.01); *A61M 39/0247* (2013.01); *A61F 2002/30235* (2013.01); *A61L 2400/16* (2013.01); *A61M 39/04* (2013.01); *A61M 2039/0264* (2013.01); *A61M 2039/0282* (2013.01)

(58) Field of Classification Search
CPC ............ A61M 2039/0282; A61F 2/022; A61F 2002/30235; A61K 9/0092; A61L 31/048; A61L 31/14; A61L 31/146; A61L 31/148; A61L 31/16; A61L 2400/16
See application file for complete search history.

(56) References Cited

U.S. PATENT DOCUMENTS

| | | | |
|---|---|---|---|
| 5,626,561 A | 5/1997 | Butler et al. | |
| 5,786,216 A * | 7/1998 | Dionne | A61F 2/022 |
| | | | 424/422 |
| 5,843,069 A * | 12/1998 | Butler | A61F 2/0004 |
| | | | 604/891.1 |
| 5,980,889 A | 11/1999 | Butler et al. | |
| 6,113,581 A * | 9/2000 | Levy | A61M 5/158 |
| | | | 604/265 |
| 6,426,214 B1 | 7/2002 | Butler et al. | |
| 7,659,219 B2 | 2/2010 | Biran et al. | |
| 8,425,928 B2 | 4/2013 | Martinson et al. | |
| 9,011,899 B2 | 4/2015 | Hasilo et al. | |
| 9,259,435 B2 | 2/2016 | Brown et al. | |
| 2008/0279833 A1 | 11/2008 | Matheny | |
| 2010/0204683 A1* | 8/2010 | Bodor | A61F 2/022 |
| | | | 604/891.1 |
| 2012/0245705 A1* | 9/2012 | Hasilo | A61M 39/0247 |
| | | | 623/23.72 |
| 2014/0088347 A1* | 3/2014 | Frigstad | A61F 2/0045 |
| | | | 600/37 |
| 2014/0257515 A1 | 9/2014 | So et al. | |
| 2015/0209479 A1 | 7/2015 | Hasilo et al. | |
| 2015/0314056 A1* | 11/2015 | Giordano | A61M 1/3486 |
| | | | 604/29 |

FOREIGN PATENT DOCUMENTS

| | | |
|---|---|---|
| EP | 0746343 | 4/1995 |
| WO | WO 91/00119 | 1/1991 |
| WO | WO93/21902 | 11/1993 |
| WO | WO98/51236 | 11/1998 |
| WO | WO2005/097219 | 10/2005 |
| WO | WO2011/025977 | 3/2011 |

* cited by examiner

IMPLANTABLE ENCAPSULATION DEVICES

FIELD

The present invention relates to implantable biological devices, and more particularly, to implantable encapsulation devices for housing a biological moiety.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other biological moieties may be introduced into a patient by surgical and/or interventional methods that place the biological moiety into a tissue bed of a patient. Surgical techniques include blunt planar dissection into a tissue or organ. Interventional techniques include injection to a target site via catheter or needle. These methods cause trauma to host tissue, leading to inflammation, lack of vascularity, and immune reactions, all of which can reduce viability and efficacy of the biological moiety. Interventional methods may also reduce the viability and efficacy of the biological moiety due to shearing forces experienced during transport through a fine-bore needle or catheter. Additionally, increases in pressure caused by the injection of the biological moiety into dense tissue can induce trauma to the biological moiety. As a result, implanted moieties often do not engraft and may undesirably migrate from the injection site.

In some instances, the biological moiety is protected from the host immune system prior to introduction into a body. One way of protecting the biological moiety is to encapsulate the moiety prior to introducing the biological moiety into tissue of a patient. While the device restricts access to elements of the host's immune system, it must also allow for the passage of nutrients and other biomolecules into the device to keep the biological moiety viable throughout its life (e.g., loading, implantation, and explanation). However, there remains many challenges with the effectiveness of current encapsulation systems through various stages of its life cycle. One challenge includes maintaining survival of the biological moiety during the implantation and healing phase where the biological moiety is exposed to a hypoxic environment with a limited source of oxygen and nutrients. There are also challenges of scalability of designing the encapsulation device for various therapies and dose ranges. One example is the need to scale various device geometries through pre-clinical animal models to a therapeutic dose in humans without changing critical design dimensions that would result in a different environment for the biological moiety. Additionally as the biological moiety reaches the end of life, there is a desire to extend the useful life of the encapsulation device or preserve the surface area in the region of the implant such that the area can be re-used for future therapies.

Therefore, there remains a need for devices that encapsulate cells and other biological moieties that are scalable to different sizes, are able to incorporate various types of biological moieties and/or sizes of biological moieties, and can be easily accessed to remove and/or replace a therapeutic device to allow for leveraging different therapies at different stages of the device life or for extending the useful life of the device through replacement.

SUMMARY

One aspect relates to an implantable encapsulation device that includes a single containment tube, a first access port located at the first end of the containment tube, a second access port located at the second end of the containment tube, a flush port fluidly connected to the second access port via a tube, and a cap releasably attached to the first end of the containment tube and covering the first access port. The flush port may also include a resealable cap. The containment tube may contain therein a biological moiety (e.g., cells) or a therapeutic device (e.g. a cell encapsulation member).

A second aspect relates to an implantable encapsulation device that includes a containment tube that has a first end and a second end and a single access port at one end (e.g., the first end). The other end (e.g., the second end) may simply be the end of the containment tube or a permanent seal affixed to the second end. The permanent seal may be a cap non-releasably attached to the second end. The containment tube may contain therein a biological moiety (e.g., cells) or a therapeutic device (e.g. a cell encapsulation member).

A third aspect relates to an implantable encapsulation device that includes a plurality of containment tubes, each containment tube having a first access port located at the first end of the containment tube and a second access port located at the second end of the containment tube. The first access ports may have thereon resealable caps to seal the first end of the containment tubes. The containment tubes may be interconnected at or near the second ends by connection members. The containment tubes are independently movable from each other and are substantially parallel to each other along a length of the device. The containment tubes may contain therein a biological moiety (e.g., cells) or a therapeutic device (e.g. a cell encapsulation member). The encapsulation device may further include a removable manifold having at least one access port that is in fluid communication with one or more of the containment tubes. A flush port may be fluidly connected to the manifold by a tube.

A fourth aspect relates to an implantable encapsulation device that includes a manifold and a plurality of containment tubes, each containment tube having a first access port at a first end and a second access port at a second end. The containment tubes are affixed to the manifold at their second ends and are fluidly connected to the manifold through the second access ports. The manifold may be located at the first end or the second end of the containment tubes. A resealable (or permanent) port may be located at the opposing end of the containment tubes. The containment tubes may be connected to each other at spaced intervals along their lengths by one or more connection member and/or may be substantially parallel to one another along a length of the containment tubes. The periodically spaced intervals may be regular (e.g., spacing is the same between connection members) or irregular (e.g., the spacing between connection members are different). In some embodiments, the containment tubes are stacked upon each other in a three dimensional configuration. In yet other embodiments, the containment tubes have a substantially planar configuration with off-axis interconnection members. The containment tubes may contain therein a biological moiety (e.g., cells) or a therapeutic device (e.g. a cell encapsulation member).

A fifth aspect relates to an implantable encapsulation device that includes at least one containment tube having a first end and a second end and a manifold centrally located between the first end and the second end. The manifold has at least one access port and is fluidly connected to the at least one containment tube. In some embodiments, the manifold includes a divider element positioned below the at least one access port.

A sixth aspect relates to an implantable encapsulation device that includes a laminate sheet and a plurality of containment channels formed by adhered layers of the laminate sheet with seams interposed between each containment channel. The plurality of containment channels may be periodically connected to each other via the seams along a length of the containment channels. It is to be appreciated that access ports, manifolds, and/or flush ports may also be included this aspect.

A seventh aspect relates to an implantable encapsulation device that includes a manifold located at the first end or the second end of the encapsulation device and a plurality of containment tubes individually affixed to the manifold and in fluid communication with the manifold. The plurality of containment tubes may be interconnected in a non-planar arrangement. In at least one embodiment, the containment tubes include a shape memory material such that the containment tubes are configured to take on the non-planar arrangement.

An eighth aspect relates to an implantable encapsulation device that includes a single containment tube having a first end, a second end, a point located between the first end and the second end, a divider element, and a manifold having a single access port positioned at the point which is centrally located between the first and second ends of the containment tube. The divider element enables the flow of a fluid containing cells to be divided such that a portion of the cells flow in a first direction (e.g., towards the first end) and a portion of the cells flow in a second direction (e.g., towards the second end). Alternatively, a cell containment member (or other therapeutic device) may be placed inside the containment tube though the access port.

A ninth aspect relates to an implantable encapsulation device that includes a first containment tube including a first distal end and a first proximal end having a first access port and a second containment tube including a second distal end and a second proximal end having a second access port, and a manifold fluidly connected to the first access port of the first proximal end and to the second access port of the second proximal end. The manifold fluidly connects the first and second containment tubes.

A tenth aspect relates to an implantable encapsulation device that includes a plurality of containment tubes having a first end and a second end, a point centrally located between the first end and the second end of the containment tubes, and a manifold having multiple access ports. The manifold is in fluid connection with the containment tubes. In some embodiments, the manifold includes divider elements that enable the flow of a fluid containing cells to be divided such that a portion of the cells flow in a first direction (e.g., towards the first end) and a portion of the cells flow in a second direction (e.g., towards the second end). It is to be noted that cell containment members may be placed inside the containment tubes though the access ports. In addition, the encapsulation device could be formed of a plurality of first containment tubes and second containment tubes connected by the manifold.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIGS. 15-17A show various three dimensional arrangements for encapsulation devices having a plurality of containment tubes in accordance with some embodiments;

DETAILED DESCRIPTION

Figure 1A:
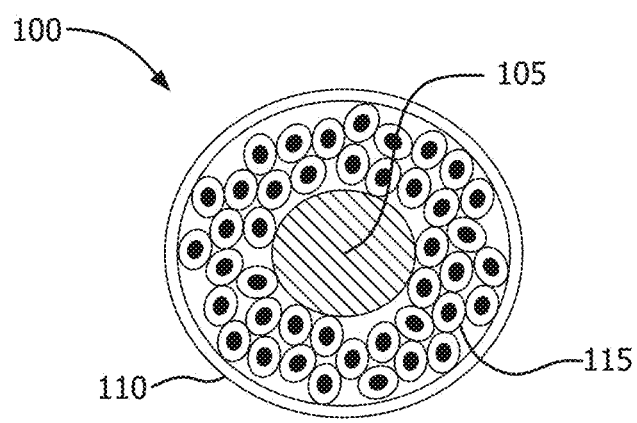
FIGS. 1A and 1B are schematic illustrations of cross-sections of a cell containment member in accordance with some embodiments.

Persons skilled in the art will readily appreciate that various aspects of the present disclosure can be realized by any number of methods and apparatus configured to perform the intended functions. It should also be noted that the accompanying figures referred to herein are not necessarily drawn to scale, and may be exaggerated to illustrate various aspects of the present disclosure, and in that regard, the figures should not be construed as limiting. Also, it is to be noted that the terms "containment tube" and "cell containment tube" are used interchangeably herein. In addition, the terms "porous polymeric membrane" and "polymeric membrane" are used interchangeably herein. It is also to be appreciated that the term "therapeutic device" may be used interchangeably with term "cell containment member" herein.

The present disclosure relates to implantable encapsulation devices that contain at least one containment tube capable of containing therein a biological moiety or a therapeutic device containing a biological moiety. Therapeutic devices may include a cell encapsulation device, a drug delivery device, or a gene therapy device. Biological moieties suitable for encapsulation and implantation using the devices described herein include cells, viruses, viral vectors, gene therapies, bacteria, proteins, polysaccharides, antibodies, and other bioactive moieties. For simplicity, herein the biological moiety is referred to as a cell or cells, but nothing in this description limits the biological moiety to cells or to any particular type of cell, and the following description applies also to biological moieties that are not cells.

The encapsulation devices include one or a plurality of containment tubes. In encapsulation devices having one containment tube, the encapsulation device may include the single containment tube, an access port at both the proximal and distal end of the containment tube, a flush port fluidly connected to the access port at the distal end, and a resealable (or permanent) cap attached to the proximal end of the containment tube. The flush port may also include a resealable cap. Although resealable caps are described herein as a means to close off and/or seal the access ports, any resealable device (e.g., permanent caps or welded seals) may be used to close and/or seal the access ports. Also, the term "access port" as used herein is meant to include any opening into the containment tube for the introduction and/or extraction of fluids, biologic moieties, and/or therapeutic devices.

In encapsulation devices having multiple containment tubes, the device may include a plurality of interconnected containment tubes substantially parallel to each other along a length of the device. As used herein, the term "substantially parallel" is meant to describe containment tubes that extend in the same direction and do not intersect each other. In another embodiment, the containment tubes intersect at least once and are independently movable. The containment tubes have an access port at the proximal end. It is to be appreciated that the terms "proximal end" and "distal end" as used herein with respect to members of the device are used for convenience to describe the device, and are exemplary in nature. For instance, a member described as being on the proximal end of the device may equally be employed at the distal end. In some embodiments, the containment tubes are formed of multiple layers that balance and enhance the hoop and tensile strength of the individual tubes. In another embodiment, the tubes are formed from a laminate material in which strength is derived, at least in part, to the materials forming the laminate. In at least one embodiment, the containment tubes are independently movable from each other, thus making the device flexible and/or compliant with tissue and/or tissue movement. In addition the periodic separation of the tubes can allow for tissue ingrowth around the tubes through the periodic tube separations, thereby improving effective device surface area for vascularization and nutrient and biomolecule exchange. The containment tubes maximize surface area available for vascularization relative to the device footprint in the body. For instance, the containment tubes take advantage of the z-direction without making the footprint larger. Additionally, there is no significant non-usable surface are due to perimeter or distal seals. In some embodiments, the containment tubes are configured to house at least one therapeutic device that provides therapeutic substances to an individual in need of treatment. In other embodiments, the containment tubes are configured to house the cells directly (i.e., with no therapeutic device). In some embodiments, the cells may be microencapsulated. For instance, the cells may be microencapsulated within a biomaterial of natural or synthetic origin, including, but not limited to, a hydrogel biomaterial. Additionally, the containment tubes may be fluidly connected so that insertion of cells into one containment tube may flow into another containment tube or so that a fluid stream may be used to remove a therapeutic device from a containment tube. In other embodiments, the containment tubes may be stacked three dimensionally or have a substantially planar arrangement with off-axis interconnection members.

The encapsulation device may also include a removable or non-removable (e.g., permanent) manifold attached at one or both ends of the containment tubes. It is to be noted that with respect to the manifolds, caps, and seals described herein may be removable or non-removable, depending on the particular situation. In some embodiments, a flush port is fluidly connected to the manifold via a tube. The tube may have a length that is substantially the length of the containment tube. Fluid can be introduced into the distal ends of the containment tubes via the flush port and manifold to assist in the discharge or removal of the one or more therapeutic devices from the proximal ends of the containment tubes. In another embodiment the encapsulation device includes a single or a plurality of containment tubes and a manifold positioned at a point between the distal end and the proximal end of the containment tube(s) (e.g., center or off center by a predetermined distance). The manifold optionally includes a divider element that directs the therapeutic device(s) or cells toward the distal end and/or the proximal end of the containment tube. The containment tube(s) may be configured to house one or more therapeutic device that provide therapeutic substances. In other embodiments, the containment tube(s) are configured to house the cells directly.

Figure 1B:
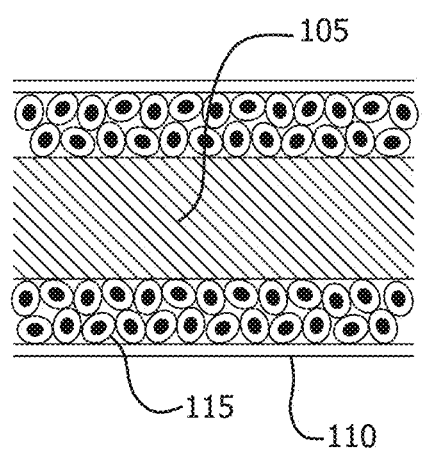

Encapsulation devices described herein may be implanted into a patient prior to or after insertion of a therapeutic device or cells into one or more of the containment tubes. For example, an encapsulation device may be inserted into a patient and allowed to vascularize such that vascular tissue grows into a vascularizing layer of the containment tube. Then, the cells or therapeutic device may be added to the containment tube in vivo. Alternatively, a therapeutic device or cells may be placed within the containment tubes prior to insertion of the encapsulation device into a tissue bed of a patient. The encapsulation devices described herein are also capable of explanation or removal from the patient such as if the patient goes into remission and no longer needs the device or the device needs to be taken out for other reasons such as a severe immunologic response. In such a case, a new encapsulation device may be implanted I. Cell Containment Member In some embodiments, a therapeutic device, such as a cell containment member, is implemented for providing therapeutic substances to an individual in need of treatment. It is to be appreciated that the term "therapeutic device" may be used interchangeably with term "cell containment member" herein. The cell containment member is structured such that it maximizes a proportion of cells in close proximity to a permeable membrane that is in contact with the environment while maintaining a geometry that is practical for implantation in a patient. As shown in FIGS. 1A and 1B, this may be accomplished by providing a cell containment member 100 that includes a core 105 that is surrounded by a permeable membrane 110. The space between the outer surface of the core 105 and the inner surface of the permeable membrane 110 define a boundary zone in which cells 115 may be contained. In some embodiments, the cells may be microencapsulated. The cells may be microencapsulated within a biomaterial of natural or synthetic origin, including, but not limited to, a hydrogel biomaterial. A maximum distance between the outer surface of the core 105 and the inner surface of the permeable membrane 110 is sufficiently narrow to provide conditions suitable for the survival and function of the contained cells 115, whereby the viability of a large proportion of the contained cells 115 is maintained. In particular, the cells 115 contained within the cell containment member 100 are able to obtain nutrients and other biomolecules from the environment outside the cell containment member 100 and expel waste products and therapeutic substances outside the cell containment member 100 through the permeable membrane 110. Suitable distances to ensure cell survival may include from about 30 microns to about 1,000 microns, from about 40 microns to about 900 microns, from about 50 microns to about 800 microns, or from about 40 microns to about 700 microns.

Any material which acts to displace cells from the center of the cell containment member 100 is suitable for use as the material of the core 105. For example, suitable core materials include, but are not limited to, polytetrafluoroethylene (PTFE), expanded polytetrafluoroethylene (ePTFE), polydimethylsiloxane, polyurethane, polyester, polyamide, or hydrogels derived from polysaccharides, alginate, hydrolyzed polyacrylonitrile, and combinations thereof. In some embodiments, the core is a flexible polymer or elastomer. In other embodiments, the core may be manufactured from polysaccharides, hydrophilic copolymers of polyacrylonitrile, a copolymer of polyacrylonitrile and acrylamide, and/or other non-porous polymers.

The permeable membrane may be manufactured from any biologically compatible material having the appropriate permeability characteristics. The permeable membrane has permeability characteristics that permit the passage therethrough of cellular nutrients, biomolecules, waste products, and therapeutic substances secreted by cells contained within the device while not permitting the passage of cells external to the cell encapsulation device. Non-limiting examples of polymers having suitable selective permeability and/or porous properties and which may be used as the permeable membrane include, but are not limited to, alginate, cellulose acetate, polyalkylene glycols such as polyethylene glycol and polypropylene glycol, panvinyl polymers such as polyvinyl alcohol, chitosan, polyacrylates such as polyhydroxyethylmethacrylate, agarose, hydrolyzed polyacrylonitrile polyacrylonitrile copolymers, polyvinyl acrylates such as polyethylene-co-acrylic acid, porous polytetrafluoroethylene (PTFE), modified polytetrafluoroethylene polymers, tetrafluoroethylene (TFE) copolymers, porous polyalkylenes such as porous polypropylene and porous polyethylene, porous polyvinylidene fluoride, porous polyester sulfone (PES), porous polyurethanes, porous polyesters, porous PPX (ePPX), porous ultra-high molecular weight polyethylene (eUHMWPE), porous ethylene tetrafluoroethylene (eETFE), porous vinylidene fluoride (eVDF), porous polylactic acid (ePLLA), and copolymers and combinations thereof, as well as woven or non-woven collections of fibers or yarns, or fibrous matrices, either alone or in combination.

Various types of prokaryotic and eukaryotic cells, mammalian cells, non-mammalian cells, and stem cells may be used with the cell containment members and containment tubes described herein. In some embodiments, the cells may be microencapsulated within a biomaterial of natural or synthetic origin, including, but not limited to, a hydrogel biomaterial. In some embodiments, the cells secrete a therapeutically useful substance. Such therapeutically useful substances include hormones, growth factors, trophic factors, neurotransmitters, lymphokines, antibodies or other cell products which provide a therapeutic benefit to the device recipient. Examples of such therapeutic cell products include, but are not limited to, insulin, growth factors, interleukins, parathyroid hormone, erythropoietin, transferrin, and Factor VIII. Non-limiting examples of suitable growth factors include vascular endothelial growth factor, platelet-derived growth factor, platelet-activating factor, transforming growth factors bone morphogenetic protein, activin, inhibin, fibroblast growth factors, granulocyte-colony stimulating factor, granulocyte-macrophage colony stimulating factor, glial cell line-derived neurotrophic factor, growth differentiation factor-9, epidermal growth factor, and combinations thereof.

II. Containment Tubes

Figure 2:
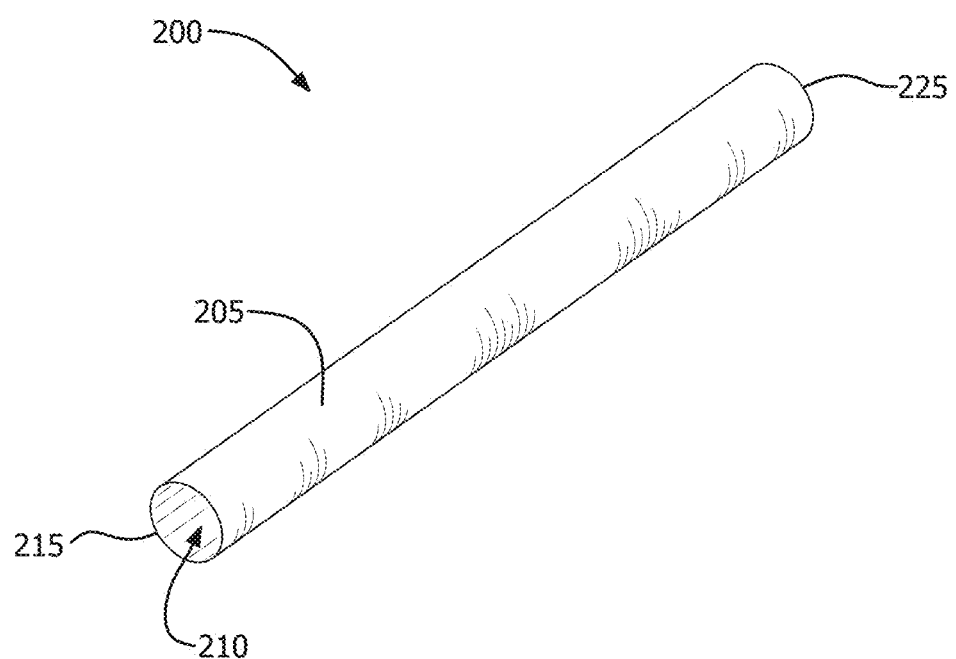
FIG. 2 is a schematic illustration of a containment tube in accordance with some embodiments.

FIG. 2 shows an exemplary implantable containment tube 200 that includes a first access port 215, a second access port 225, a permeable membrane 205 forming the exterior of the containment tube 200, and a lumen 210 extending through the containment tube 200. In some embodiments, the containment tube 200 is a flexible tube that is configured to receive one or more therapeutic device that provides therapeutic substances to an individual in need of treatment. In accordance with some aspects of the present disclosure, the containment tube 200 has a cross-section in a shape that conforms or substantially conforms, at least in part, to the form of the therapeutic device (e.g., cell containment member) the containment tube 200 is intended to house. As non-limiting examples, the cross-section of the containment tube 200 may be circular, ovoid, or elliptical. In the embodiments disclosed herein, the containment tubes may have inner diameters that range from about 100 microns to about 5 mm, from about 150 microns to about 4.5 mm, from about 200 microns to about 4 mm, or from about 250 microns to about 3.5 mm. In some embodiments in which multiple containment tubes are utilized, the containment tubes may be separated from each other a distance from about 0.1 microns to about 3 mm, from about 5 microns to about 2.5 mm, from about 10 microns to about 2 mm, from about 25 microns to about 1.5 mm, or from about 50 microns to about 1 mm. It is to be noted that all ranges described herein are exemplary in nature and include any and all values in between.

In some embodiments, the containment tube 200 is a flexible tube configured to receive cells directly (e.g., without the presence of a therapeutic device). The containment tube 200 is structured such that it maximizes the number of cells in close proximity to the permeable membrane 205 that is in contact with the environment while maintaining a geometry which is practical for implantation in a patient. The lumen 210 defines an area in which cells may be contained. In addition, the lumen 210 provides conditions that are suitable for survival and function of the contained cells. Suitable distances to ensure cell survival may include from about 30 microns to about 1,000 microns, from about 40 microns to about 900 microns, from about 50 microns to about 800 microns, or from about 40 microns to about 700 microns. For example, the cells contained within the lumen 210 of the containment tube 200 are able to obtain nutrients and other biomolecules from the environment outside the containment tube 200 and expel waste products and therapeutic substances outside the containment tube 200 through the permeable membrane 205.

The containment tube 200 is scalable in that it can easily be configured throughout a range of diameters so that the containment tube can be used to house cells and/or therapeutic devices with varying shapes and sizes while ensuring survival and function of these cells. To ensure that conditions are suitable for the survival and function of the cells contained within the containment tube 200, the diameter of the containment tube 200 is either sufficiently small such that nutrients and other biomolecules are able to reach the center of the tube 200 or a central portion of the containment tube 200 contains a cell displacing member so that a maximum distance between the displacing member and the wall of the containment tube 200 is such that the viability of a large portion of the cells is maintained. In some embodiments, cells are introduced into the containment tube 200 in the form of a suspension or slurry in a medium. The cells may be individual cells, cell aggregates, or cell clusters. As one example, the medium may be a cell culture or cell growth medium, optionally including desired nutrients and other biomolecules. In some embodiments, insertion of the cells into the containment tube may be accomplished using a syringe.

In some embodiments, the permeable membrane 205 of the containment tube 200 is made of a porous polymeric material having selective sieving and/or porous properties. The porous polymeric material controls the passage of solutes, biochemical substances, viruses, and cells, for example, through the material, primarily on the basis of size. Porous polymeric materials having suitable selective permeability and/or porous properties useful for construction of containment tubes as described herein include, but are not limited to, alginate, cellulose acetate, polyalkylene glycols such as polyethylene glycol and polypropylene glycol, pan-vinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene (PTFE), modified polytetrafluoroethylene polymers, tetrafluoroethylene (TFE) copolymers, porous polyalkylenes such as porous polypropylene and porous polyethylene, porous polyvinylidene fluoride, porous polyester sulfone (PES), porous polyurethanes, porous polyesters, and copolymers and combinations thereof. In other embodiments, the materials useful as an outer porous layer include biomaterial textiles.

In some embodiments, the porous polymeric material may be a bio-absorbable material. Alternatively, the porous polymeric material may be coated with a bio-absorbable material or a bio-absorbable material may be incorporated into or onto the porous polymeric material in the form of a powder. Coated materials may promote infection site reduction, vascularization, and favorable type 1 collagen deposition. The porous polymeric materials described herein may include any bio-absorbable material known in the art. Non-limiting examples include, but are not limited to, polyglycolide:trimethylene carbonate (PGA:TMC), polyalphahydroxy acid such as polylactic acid, polyglycolic acid, poly(glycolide), and poly(lactide-co-caprolactone), poly(caprolactone), poly(carbonates), poly(dioxanone), poly (hydroxybutyrates), poly(hydroxyvalerates), poly (hydroxybutyrates-co-valerates), and copolymers and blends thereof.

In some embodiments, the bio-absorbable material may have the capability to generate reactive oxygen species (ROS) at different levels in the body. ROS have been shown to promote various cell responses in the body, including, but not limited to, inhibiting or promoting cell proliferation, differentiation, migration, apoptosis, and angiogenesis. ROS generating materials can be made according to the teachings set forth in, for example, U.S. Pat. No. 9,259,435 to Brown, et al.

Figure 3:
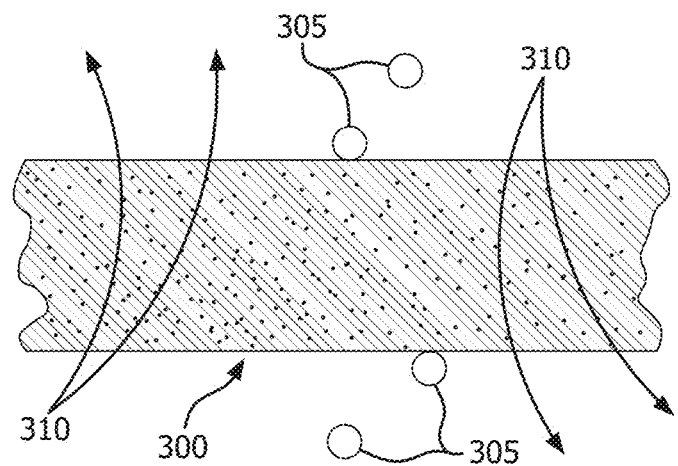
FIGS. 3-10 are schematic illustrations of cross-sections of a porous polymeric material used to construct a containment tube in accordance with some embodiments.

In embodiments where the permeable membrane 205 is porous only through a portion of its thickness, the molecular weight cutoff, or sieving property, of the porous membrane 205 begins at the surface. As a result, certain solutes and/or cells do not enter and pass through the porous spaces of the material from one side to the other. FIG. 3 shows a cross-sectional view of a porous polymeric material 300 useful in a containment tube described herein, where the selective permeability of the polymeric material 300 excludes cells 305 from migrating or growing into the porous spaces of the polymeric material 300 while permitting bi-directional flux of solutes 310 across the thickness of the polymeric material 300. Vascular endothelial cells can combine to form capillaries thereon. Such capillary formation or neovascularization of the polymeric material 300 of the containment tube permits fluid and solute flux between tissues of a patient and the contents of a therapeutic device to be enhanced.

Figure 4:
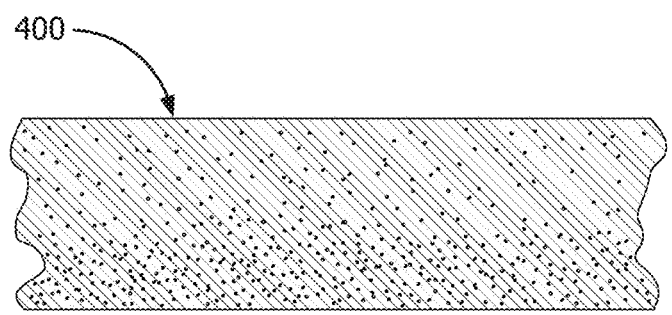
Figure 5:
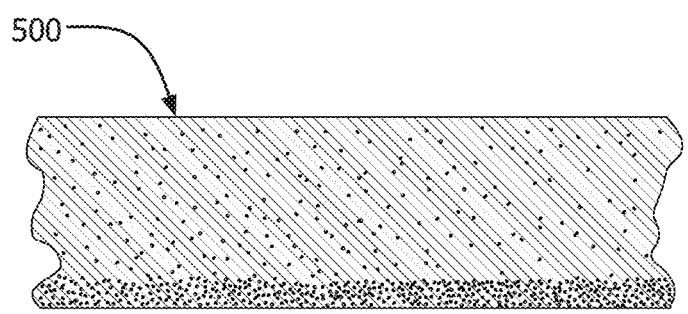

In some embodiments, permeability of the polymeric material can be varied continuously across the thickness of the polymeric material. FIG. 4 is a cross-sectional view of a porous polymeric material 400 useful in a containment tube described herein, where the selective permeability of the polymeric material 400 varies continuously across the thickness of the material as indicated by the gradually increasing density of the stippling in the figure. In some embodiments, the permeability of the porous polymeric material 400 is varied from one cross-sectional area of the material to another to form a stratified structure. FIG. 5 is a cross-sectional view of a polymeric material 500 useful in a containment tube described herein, where the selective permeability of the polymeric material 500 varies across the thickness of the polymeric material 500 as indicated by the increasing density of the stippling in the figure.

Figure 6:
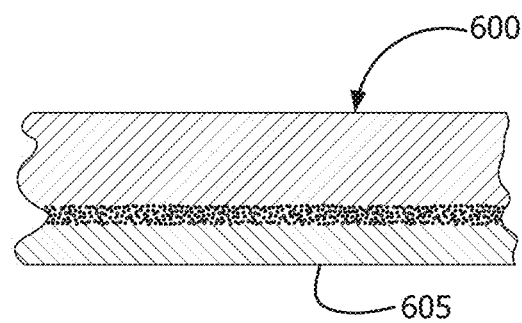

In some embodiments, the permeability of the porous polymeric material is varied across its thickness with additional layers of porous polymeric material. FIG. 6 is a cross-sectional view of a porous polymeric material 600 useful in a containment tube described herein, where the selective permeability of the polymeric material 600 is varied across the thickness of the polymeric material 600 with one or more additional layers of porous polymeric material 605. The additional layers of porous polymeric material 605 may have the same composition and permeability as the initial layer of porous polymeric material 600 or the one or more additional layers 605 may have a different composition and/or permeability.

Figure 7:
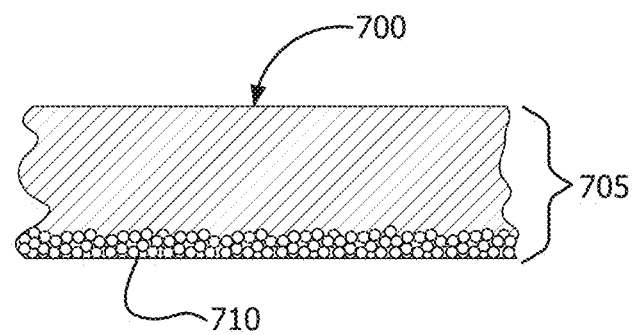

In another embodiment, the selective permeability of the porous polymeric material is varied by impregnating the void spaces of the porous polymeric material with a hydrogel material. A hydrogel material can be impregnated in all or substantially all of the void spaces of a porous polymeric material (e.g., pores of a porous membrane) or in only a portion of the void spaces. For example, by impregnating a porous polymeric material with a hydrogel material in a continuous band within the polymeric material adjacent to and/or along the interior surface of the porous polymeric material, the selective permeability of the porous polymeric material is varied from an outer cross-sectional area of the porous polymeric material to an inner cross-sectional area of the porous polymeric material. FIG. 7 is a cross-sectional view of a porous polymeric material 700 useful in a containment tube described herein, where the selective permeability of the polymeric material 700 is varied across the thickness 705 of the polymeric material 700 with a hydrogel material 710.

The amount and composition of hydrogel material impregnated into the porous polymeric material depends in large part on the particular porous polymeric material used to construct an apparatus, the degree of permeability required for a given application, and the biocompatibility of the hydrogel material. Non-limiting examples of useful hydrogel materials for use in the present invention include, but are not limited to, hydrolyzed polyacrylonitrile, alginate, agarose, carrageenan, collagen, gelatin, polyvinyl alcohol, poly(2-hydroxyethyl methacrylate), poly(N-vinyl-2-pyrrolidone), polyethylene glycol, polyethyleneimine, fibrin-thrombin gels, or gellan gum, and copolymers thereof, either alone or in combination. In certain aspects of the present invention, the total thickness of an expanded PTFE/hydrogel composite may range from about 2 µm to about 1000 µm.

Figure 8:
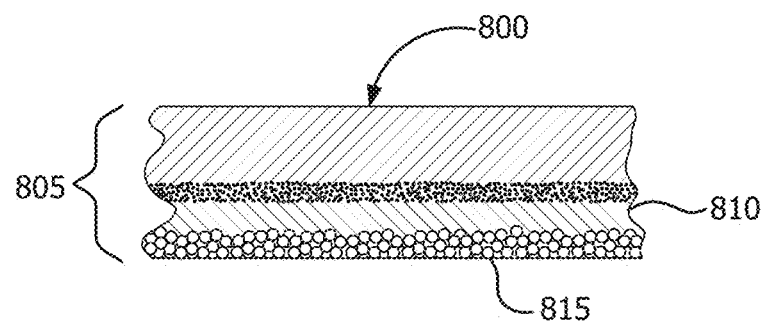

In yet other embodiments, the permeability of the porous polymeric material can be varied across the thickness of the polymeric material with an additional layer of porous polymeric material and a further layer of hydrogel material. FIG. 8 is a cross-sectional view of a porous polymeric material 800 useful in a containment tube described herein, where the selective permeability of the polymeric material 800 is varied across the thickness 805 of the polymeric material 800 with an additional layer of porous polymeric material 810 and a further layer of a hydrogel material 815. An advantage of this embodiment is the additional protection provided an implant patient against contamination with cells from a failed containment tube or cell containment member described herein. In addition, this configuration will provide a strong cell and humoral immunoisolation barrier.

Figure 9:
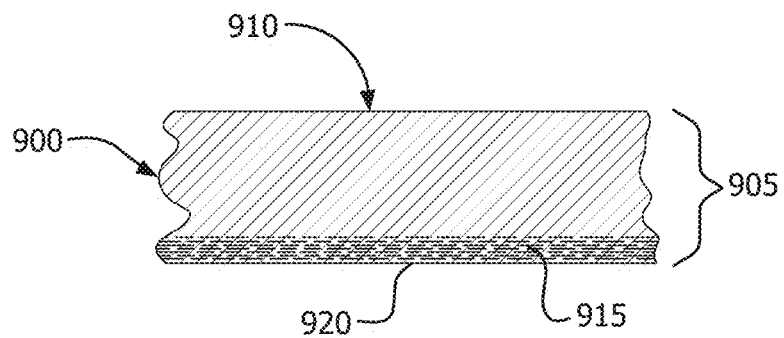

In some embodiments, the permeability of the porous polymeric material is selected to permit growth of cells from a patient into, but not through, the polymeric material. In one or more embodiment, a cell permeable zone is formed in the void spaces of a porous polymeric material starting at the exterior surface of the polymeric material and continuing to a point within the polymeric material adjacent to the interior surface of the cell containment tube where the permeability of the porous polymeric material to cells is decreased so that cells that have migrated into the void spaces of the polymeric material cannot migrate further and penetrate the interior surface of the polymeric material. FIG. 9 depicts a cross-sectional view of a porous polymeric material 900 useful in a containment tube described herein, where the polymeric material 900 includes a cell permeable zone 905 beginning at the exterior surface 910 of the polymeric material 900 and continuing across the thickness of the polymeric material 900 to a cell exclusion zone 915 within the polymeric material 900 adjacent to and continuous with the interior surface 920 of the polymeric material 900.

The region of the porous polymeric material in which cells cannot migrate or grow is referred to as a cell exclusion zone and is impervious to cellular ingrowth. A cell exclusion zone prevents or minimizes invasive cells from entering the lumen of the containment tube and contacting, adhering to, fouling, ingrowing, overgrowing, or otherwise interfering with a therapeutic device or cells contained within the containment tube. To exclude invading host cells from growing through to the interior surface of the containment tube, the pore size of the cell exclusion zone may be less than about 5 microns, less than about 1 micron, or less than about 0.5 microns, as measured by porometry. In some embodiments, the permeability of the polymeric material may be adjusted with a hydrogel material.

In some embodiments, the permeable membrane is a composite material or laminate that includes an outer porous polymeric layer and an inner porous polymeric layer disposed adjacent to the outer porous polymeric layer. The inner and outer porous polymeric layers have different porosities, and may include or be formed of the same material or different materials. In some embodiments, the inner porous layer has a porosity that is less than the porosity of the outer porous layer. Portions of the inner porous polymeric layer form the interior surface of the containment tube.

The inner porous polymeric layer is impervious to cellular or vascular ingrowth, and is sometimes referred to as a cell retentive layer or a tight layer. In some embodiments, the inner porous layer has an average pore size that is less than about 5 microns, less than about 1 micron, or less than about 0.5 microns, as measured by porometry. In some embodiments, the pores resist cellular ingrowth but are selectively permeable to macromolecules.

The outer porous layer has an average pore size that is large enough to permit growth of vascular tissue from a patient into the pores of the outer porous polymeric layer. This layer may be referred to as a vascularizing or an open layer. In some embodiments, the pore size of the outer porous polymeric layer is greater than about 5.0 microns, as measured by porometry. Ingrowth of vascular tissues through the outer porous layer facilitates nutrient and other biomolecule transfer from the body to the cells encapsulated in the containment tube.

Optionally, the containment tube may include only the outer porous polymeric material, or a laminate formed of multiple porous polymeric materials, where each porous polymeric material has sufficient porosity to permit growth of vascular tissue from a patient into the pores of the polymeric material. As such, growth of vascular tissue is permitted through the entire thickness of the polymeric material(s) forming the containment tube.

Various cell types can grow into the cell permeable zone vascularizing (open) layer of a porous polymeric material of a containment tube as described herein. The predominant cell type that grows into a particular porous polymeric material depends primarily on the implantation site, the composition and permeability of the material, and any biological factors, such as cytokines and/or cell adhesion molecules, for example, that may be incorporated in the material or introduced through the containment tube. In some embodiments, vascular endothelium is the predominant cell type that grows into a porous polymeric material for use in a containment tube. Vascularization of the porous polymeric material by a well-established population of vascular endothelial cells in the form of a capillary network is encouraged to occur as a result of neovascularization of the material from tissues of a patient into and across the thickness of the material very close to the interior surface of the apparatus, but not across the cell exclusion zone or cell retentive (or tight) layer.

Figure 10:
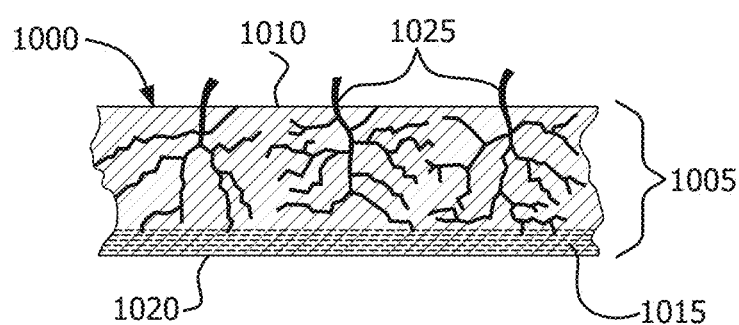

FIG. 10 is a cross-sectional view of a porous polymeric material 1000 useful in a containment tube described herein, where the polymeric material 1000 includes a cell permeable zone 1005 beginning at the exterior surface 1010 of the polymeric material 1000 and continuing across the thickness of the polymeric material 1000 to a cell exclusion zone 1015 within the polymeric material 1000 adjacent to and continuous with the interior surface 1020 of the polymeric material 1000. The cell permeable zone 1005 is populated with vascular structures 1025. Vascularization can occur without the addition of biological factors and/or, angiogenic factors, which can be used to enhance vascularization of the containment tube. In addition, angiogenesis can be stimulated by conditions, such as hypoxia. The neovascularization of a containment tube improves mass transport of therapeutic drugs or biochemical substances between the interior surface of the containment tube and tissues of a patient, thereby enhancing the quantity and rate of transport of therapeutic drugs or biochemical substances between the contents of a therapeutic device housed in the containment tube and tissues of the patient.

In some embodiments, the encapsulation device is implanted into a patient in a configuration similar to or dissimilar to its final configuration, but for the encapsulation device to assume its final shape, some migration of the implanted encapsulation device may occur. Vascularization and other tissue ingrowth of the cell permeable zones of the containment tubes as described herein can anchor the encapsulation device at the implantation site. This anchoring, however, does not prevent the transformation of the encapsulation device into its primary shape because shape changes of the device occur shortly after implantation and before significant vascularization and other tissue growth occurs. The shape transformation may be a result of significant forces exerted by a shape memory element or by the manifold joining the ends of the containment tubes. The anchoring minimizes or prevents the encapsulation device from moving from the implantation site over time and once sufficient anchoring has occurred, can assist the encapsulation device in maintaining its shape. Maintaining the shape of a containment tube as described herein is often necessary for easy placement, replacement, and proper functioning of the cells contain contained in the cell containment tube(s) within the encapsulation device.

In some embodiments, the containment tube includes a shaping element. The shaping element can be configured to induce the containment tube into a more compliant structure such as a curved or wavy shape, such as a generally toroidal configuration, in a tissue bed. In some embodiments, the shaping element may also hold the containment tube in a desired shape during implantation and subsequent use. Non-limiting examples of useful shaping elements include windings, strips, spline, stents, and combinations thereof. The shaping elements may be on the exterior surface of the conduit of the containment tube, between the layers of the conduit or along the interior surface of the conduit. In one embodiment, the shaping element provides the ability to insert the containment tube in any configuration convenient for insertion, and once inserted the containment tube independently assumes a preferred in-use configuration. In another embodiment, a shaping element holds the containment tube in a preferred configuration in use such that therapeutic devices can easily be removed from and inserted into the containment tube.

In some embodiments, the shaping element includes a shape memory material or structure made therefrom. Non-limiting examples of useful shape memory materials include shape memory alloys, such as nitinol, and shape memory polymers such as polyetheretherketone, polymethyl methacrylate, polyethyl methacrylate, polyacrylate, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, polyurethanes with ionic or mesogenic components made by a pre-polymer method, and copolymers or polymer blends thereof. Other block copolymers also show the shape-memory effect, such as, for example, a block copolymer of polyethylene terephthalate (PET) and polyethyleneoxide (PEO), block copolymers containing polystyrene and poly(1,4-butadiene), and an ABA triblock copolymer made from poly(2-methyl-2-oxazoline) and polytetrahydrofuran. Non-limiting shape memory alloys include, but are not limited to, copper-aluminum-nickel, copper-zinc-aluminum, and iron-manganese-silicon alloys. In addition to inducing the containment tube into a desired (pre-determined) configuration in use, the shape memory element facilitates implantation, including facilitating any change in profile of the containment tube during implantation.

Many of the materials used to construct a containment tube as described herein are inherently radio-opaque. Those materials that are not inherently radio-opaque can be modified to be radio-opaque by impregnation of the material with barium, for example. Other useful methods for rendering a material radio-opaque are known to those skilled in the art. The radio-opacity of materials used to construct a containment tube as described herein is mainly used to facilitate surgical placement of the containment tube or to locate the containment tube in a patient following implantation.

In some embodiments, a containment tube as described herein maintains a consistent cylindrical cross-section for containing cells or a generally cylindrically shaped therapeutic device (e.g., a cell containment member). In some tubular embodiments, open ends of the tube can be prevented from collapsing with a stent. The stent can be in any shape and made of any biocompatible material useful for keeping all or part of tubular containment tube in an opened, or expanded, tubular form during storage and/or following implantation. Useful materials for a stent include, but are not limited to, stainless steel, titanium, and hydrogels. To maintain the containment tube in an expanded configuration when a therapeutic device (e.g., cell containment member) is not inserted or no cells are present, an inert core simulating the shape and resilience of a therapeutic device may be placed in the containment tube. A cell encapsulation device as described herein may be implanted into a patient prior to or after insertion of a therapeutic device or cells into one or more of the containment tubes. For example, an encapsulation device may be inserted into a patient and allowed to vascularize such that vascular tissue grows into a vascularizing layer of the cell containment tube. The cells or therapeutic device may then be added to the containment tubes in vivo. Alternatively, a therapeutic device or cells may be placed within the containment tubes prior to insertion of the encapsulation device into a tissue bed of a patient.

III. Encapsulation Device with One Containment Tube

Figure 11A:
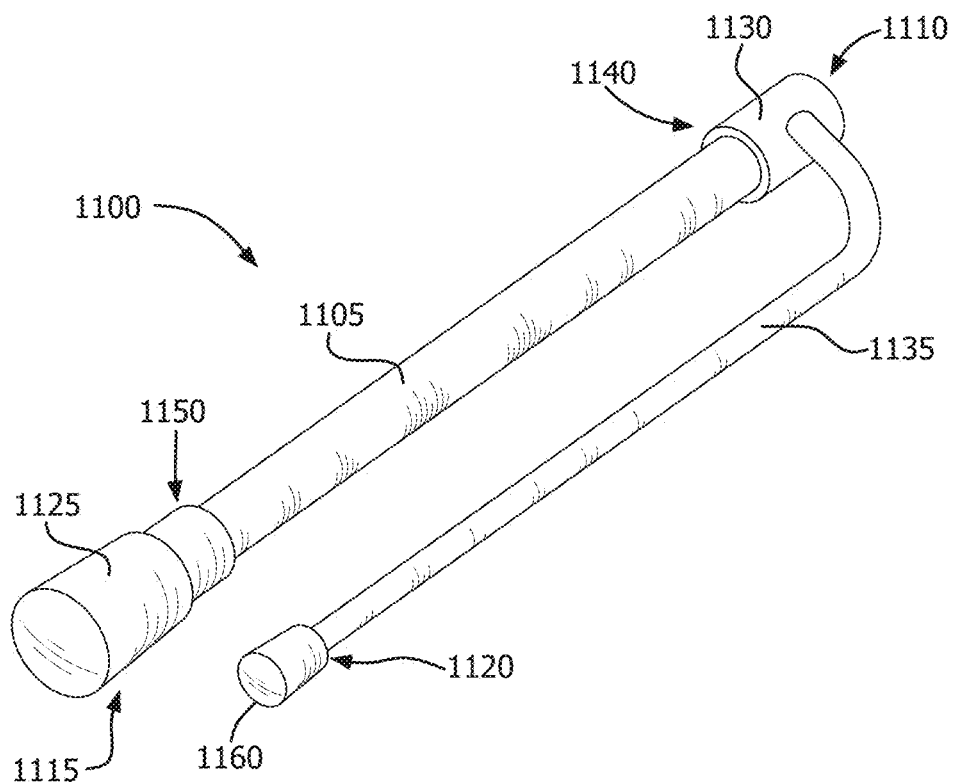
FIG. 11A is a schematic illustration of a containment tube having two access ports and a flush port in accordance with some embodiments.

FIG. 11A depicts an encapsulation device 1100 containing a single containment tube 1105 in accordance with at least one embodiment. The encapsulation device 1100 may include a containment tube 1105, a first access port 1150 at a proximal end 1115, a second access port 1140 at a distal end 1110, a flush port 1120 fluidly connected to the second access port 1140 port via a tube 1135 and a connection member 1130. A resealable cap 1125 may be attached to the proximal end 1115 of the containment tube 1105. The flush port 1120 may also include a resealable cap 1160. Although resealable caps are described herein as a means to close off and/or seal the access ports, any resealable device may be used. In alternative embodiments, the encapsulation device 1100 may have a resealable cap 1125 at the distal end 1110 and a connection member 1130 at the proximal end 1115 (not illustrated). In other embodiments, the encapsulation device 1100 may have a resealable cap 1125 at both the proximal end 1115 and the distal end 1110 (not illustrated). In yet other embodiments, the encapsulation device 1100 has a flush port 1120 at both the proximal end 1115 and the distal end 1110 (not illustrated).

The second access port 1150 provides an access point through which cells and/or one or more therapeutic device may be moved in and out of the luminal region of the containment tube 1105. The flush port 1120 provides an access point through which a fluid stream can be delivered to the luminal region of the containment tube 1105 to fill and/or flush the luminal region of the containment tube 1105. In some embodiments, the fluid stream can be used to fill the luminal region with cells. In other embodiments, the fluid stream can be used to push the one or more therapeutic devices or cells from the luminal region of the containment tube 1105 through the second access port 1150 to an area external to the containment tube 1105.

As discussed above, the flush port 1120 is in fluid communication with the containment tube 1105 via the tube 1135. In some embodiments, the tube 1135 is constructed of a biocompatible material having a length that is substantially equal, such as within 1 cm, to a length of the containment tube 1105 such that a proximal end of the tube 1135 with the resealable cap 1160 resides near or adjacent to the proximal end 1115 of the containment tube 1105 (and/or near to the proximal end of the encapsulation device 1100) when the encapsulation device 1100 is implanted in a patient. In embodiments in which the encapsulation device 1100 has a flush port at both the proximal end 1115 and the distal end 1110 of the containment tube 1105, the access port on either the proximal end or the distal end of the containment tube can be used to provide an access point through which cells and/or one or more therapeutic device may be moved in and out of the luminal region of the containment tube (not illustrated). The containment tube 1105 may be constructed with a composite material having a cell retention layer and vascularizing layer as described herein.

The resealable caps 1125, 1160 and the connection fitting 1130 are secured to the porous polymeric material forming the containment tube 1105. Commercially available fittings, such as Luer-lok connectors can also be used as a resealable cap 1125, 1160. In some embodiments, one or more of resealable caps 1125,1160 and/or connection fitting 1130 is a hollow cylindrically shaped fitting having a first portion that fits snugly inside an end of the containment tube 1105 and a second portion that extends beyond the end of the containment tube 1105 to receive and retain a sealing element. In some embodiments, the resealable caps 1125, 1160 and connection fitting 1130 may be fabricated by injection molding a fitting onto the end of the containment tube 1105 using techniques known to those skilled in the art. In some embodiments, the resealable cap 1125 is a hole in the containment tube 1105 with one or more flexible pieces, or flaps, of porous polymeric material positioned to cover and close the hole. The flaps may be formed as part of the encapsulation device 1100 or may be attached to the encapsulation device 1100 subsequent to its construction.

The resealable caps 1125, 1160 and connection fitting 1130 can be repeatedly opened and closed with a seal. As used herein, a seal includes, but is not limited to, caps, plugs, clamps, compression rings, or valves. The seal may be attached to the resealable caps 1125, 1160 and connection fitting 1130 with friction, by clamping, or with a screw comprised of threads and grooves. Depending on the intended use of the encapsulation device 1100, the caps 1125, 1160 and connection fitting 1130 are sealed to create a hermetical seal, a fluid-tight seal, or a non-fluid-tight seal. An encapsulation device 1100 intended for life-time or long term (e.g., at least about three weeks) implantation in a patient, may be sealed with a hermetical or a fluid-tight seal.

The flush port 1120 and tube 1135 may have any shape suitable for facilitating filing and flushing of the luminal region of the containment tube 1105. In some embodiments, the flush port 1120 and tube 1135 are aligned in a same horizontal plane as the cell containment tube 1105 (as shown in FIG. 11A). In some embodiments, the tube 1135 may have an elbow or angle (e.g., 30°, 45°, or 90°) such that the tube 1135 and flush port 1120 extend through the horizontal plane of the cell containment tube 1105 (not shown).

In accordance with some embodiments, a therapeutic device (e.g., cell containment member) may be housed within the containment tube 1105. In some embodiments, the therapeutic device is designed to seal with an interface of the resealable cap 1125 or the connection fitting 1130. In some embodiments, the therapeutic device includes a grasping structure (e.g., a tab) such that a clinician can hold the grasping structure to hold or manipulate (e.g., insert or remove) the therapeutic device from within the containment tube. Additionally, the therapeutic device can be repeatedly attached and detached with a seal to the resealable cap 1125 or connection fitting 1130 such that the therapeutic device can be inserted and retrieved from the containment tube 1105. In some embodiments, the therapeutic device is removed and a new therapeutic device inserted. It is to be appreciated that not only is the therapeutic device removable, but also the encapsulation device 1100.

Figure 11B:
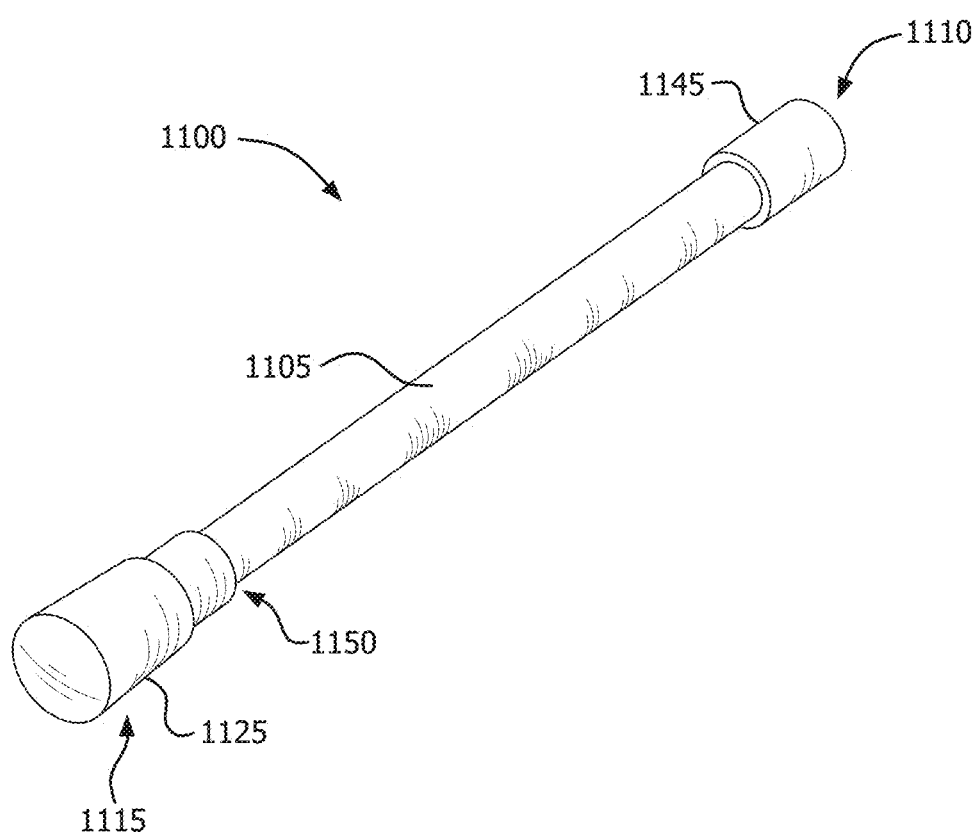
FIG. 11B is a schematic illustration of a containment tube having a single access port in accordance with some embodiments.

FIG. 11B illustrates a containment tube 1105 that has a single access port 1150 at a proximal end 1115 and a permanent cap 1145 (or seal) at the distal end 1110. In the embodiment depicted in FIG. 11B, a resealable cap 1125 is used to close or seal the access port 1150 when not in use. In some embodiments, the distal end 1110 of the containment tube 1105 is simply the closed end of the containment tube (and therefore no cap is needed to seal the end). As with the embodiment described above, a therapeutic device can be housed within the containment tube 1105 and may be inserted into the tube 1105 through the access port 1150. In addition, the therapeutic device can be accessed and/or retrieved from the containment tube 1105 via the access port 1150.

IV. Encapsulation Device with Multiple Containment Tubes

Figure 12A:
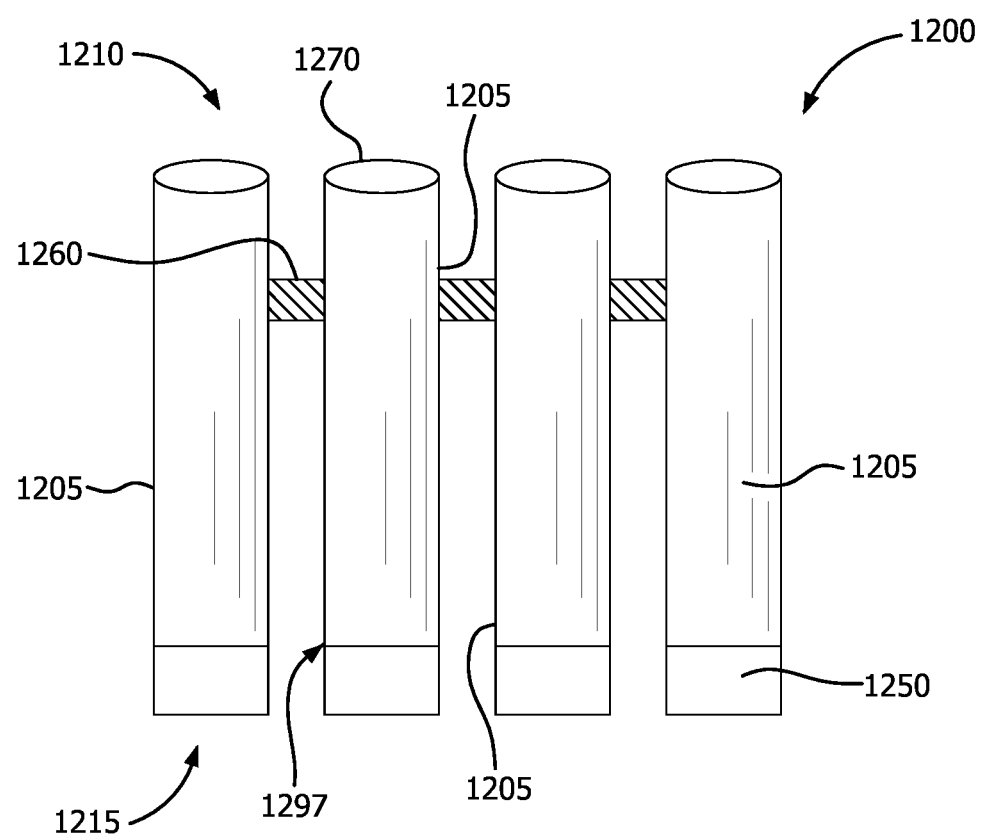
FIG. 12A is a schematic illustration of an encapsulation device having a plurality of interconnected containment tubes in accordance with some embodiments.

FIG. 12A depicts an encapsulation device containing multiple containment tubes in accordance with at least one embodiment. As shown, the encapsulation device 1200 includes a plurality of interconnected containment tubes 1205 that are substantially parallel to each other along a length of the device 1200. Each containment tube 1205 has a first access port 1270 at a proximal end 1210 and a second access port 1297 at a distal end 1215. The second access ports 1297 may have thereon resealable caps 1250 to seal the distal ends of the containment tubes 1205. Although not depicted, resealable caps may also be affixed to the first access ports 1270 to seal the proximal ends of containment tubes 1205. The containment tubes 1205 may be interconnected at connection members 1260 at their proximal ends. The connection members 1260 may be made of the porous polymeric material(s) forming the containment tubes 1205 or be made of a different polymeric and/or other biocompatible material. Although not depicted, a flush port may be fluidly connected to one or more containment tube(s) 1205 to fill and/or flush the luminal region of the containment tube(s) 1205 in a manner such as described above with reference to FIG. 11A. In some embodiments, the therapeutic device(s) is removed from the containment tube(s) 1205 and a new therapeutic device inserted. It is to be appreciated that not only are the therapeutic devices removable, but also the encapsulation device 1200.

Figure 12B:
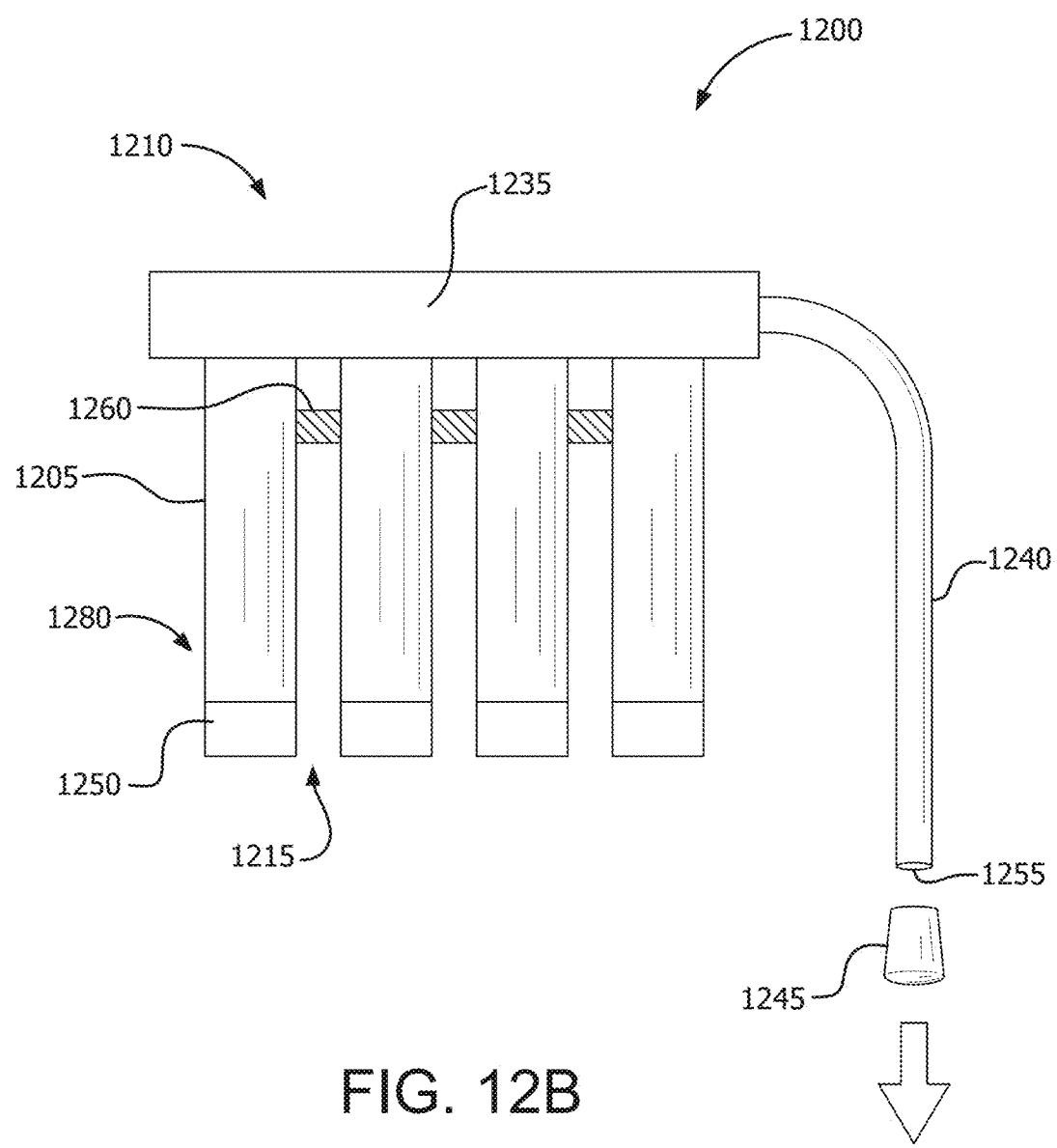
FIG. 12B is a schematic illustration of the encapsulation device of FIG. 12A including a flush port and a manifold in accordance with some embodiments.

In the embodiment depicted in FIG. 12A, the containment tubes 1205 are independently movable from each other, thus making the device 1200 flexible and/or compliant with tissue and/or tissue movement. The containment tubes 1205 may be configured to house at least one therapeutic device. Alternatively, the containment tubes 1205 may be configured to house cells (or other biological moieties) directly. In some embodiments, the containment tubes 1205 may be fluidly connected, such as by the connection members 1260 and/or by a flush port 1255 connected to a manifold 1235 via a tube 1240 (see FIG. 12B) so that insertion of cells into one containment tube may flow into another containment tube or so that a fluid stream may be applied to the containment tubes 1205 to remove a therapeutic device from a containment tube. In some embodiments, a new therapeutic device is inserted into the containment tube. Once filled, the manifold 1235 may be removed and the containment tubes sealed. As discussed above, a seal includes, but is not limited to, caps, plugs, clamps, compression rings, or valves. It is to be noted that the embodiment depicted in FIG. 12B is less compliant (more stiff) than the embodiment of FIG. 12A due to the inclusion of the manifold 1235.

Figure 12C:
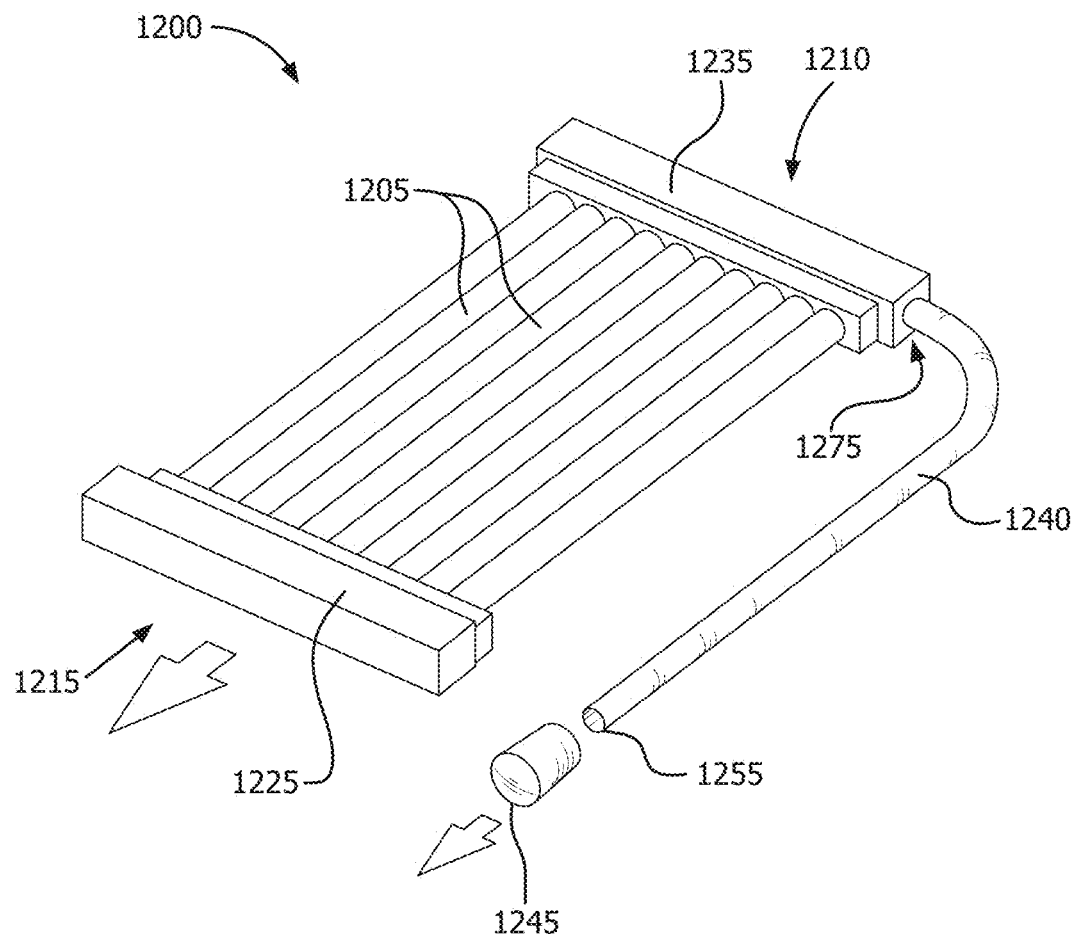
FIG. 12C is a schematic illustration of an encapsulation device having a plurality of containment tubes and a manifold (with a flush port) located at a distal end thereof in accordance with some embodiments.

Turning to FIG. 12C, an encapsulation device 1200 may include a plurality of containment tubes 1205 having first access ports (not illustrated) at a distal end 1210, second access ports (not illustrated) at a proximal end 1215, a resealable port 1225 sealing the second access ports, and a manifold 1235 fluidly connecting the first access ports at the distal end 1210. A flush port 1255 may be fluidly connected to the manifold 1235 via a tube 1240. When not in use, a resealable cap 1245 may cover and seal the flush port 1255.

Figure 31A:
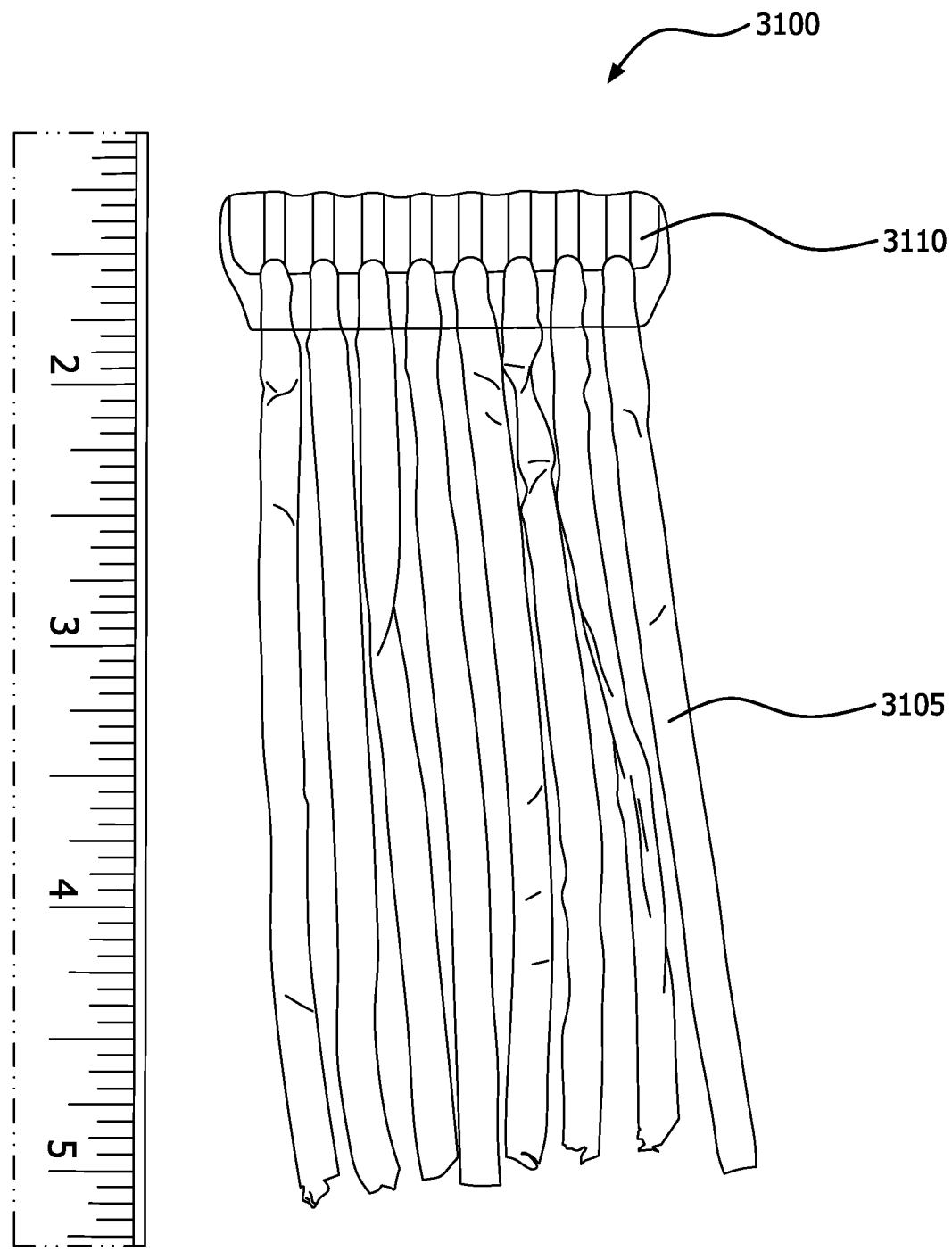
FIGS. 31A and B are schematic illustrations depicting containment tubes connected by an access port on one end in accordance with some embodiments.
Figure 31B:
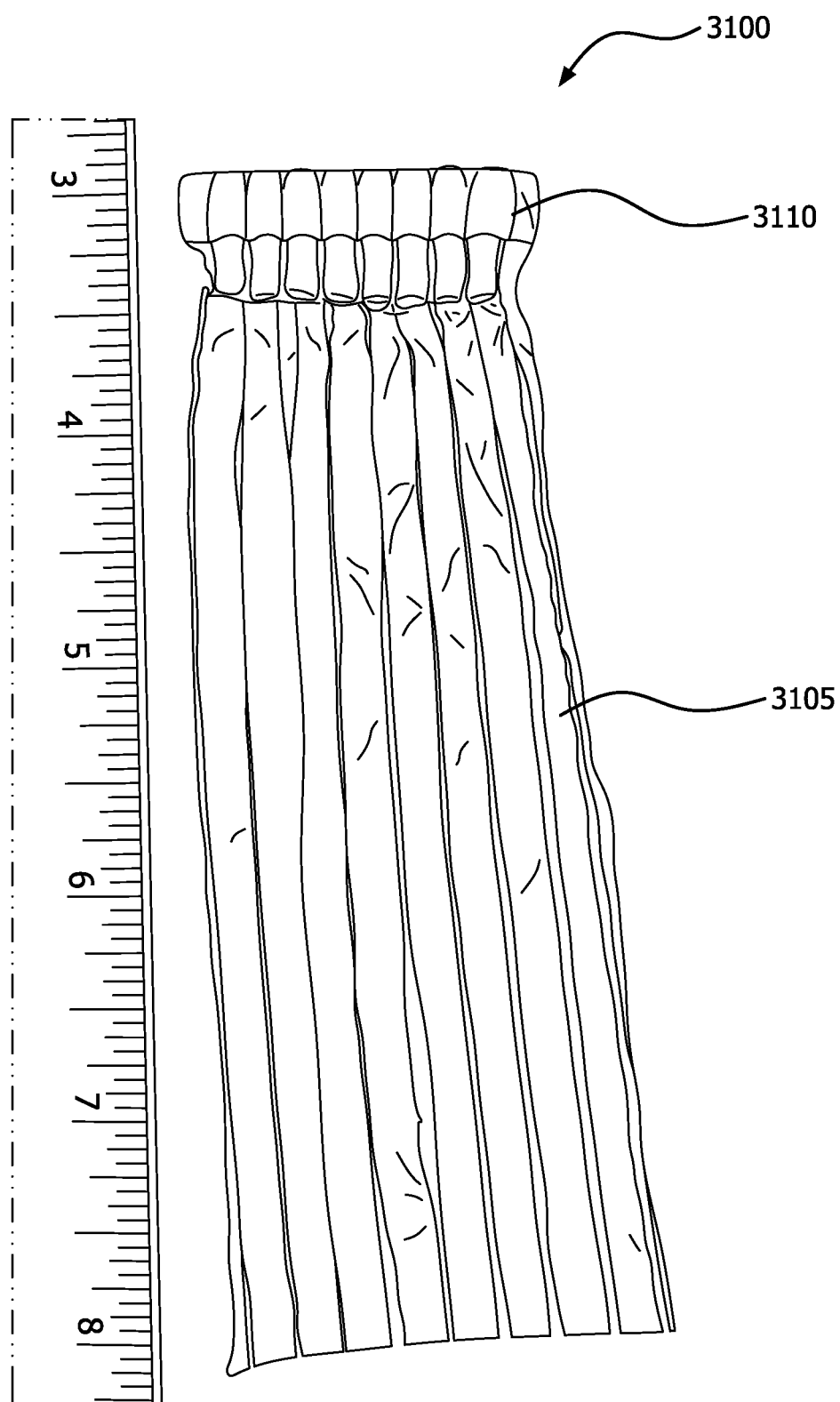
Figure 32A:
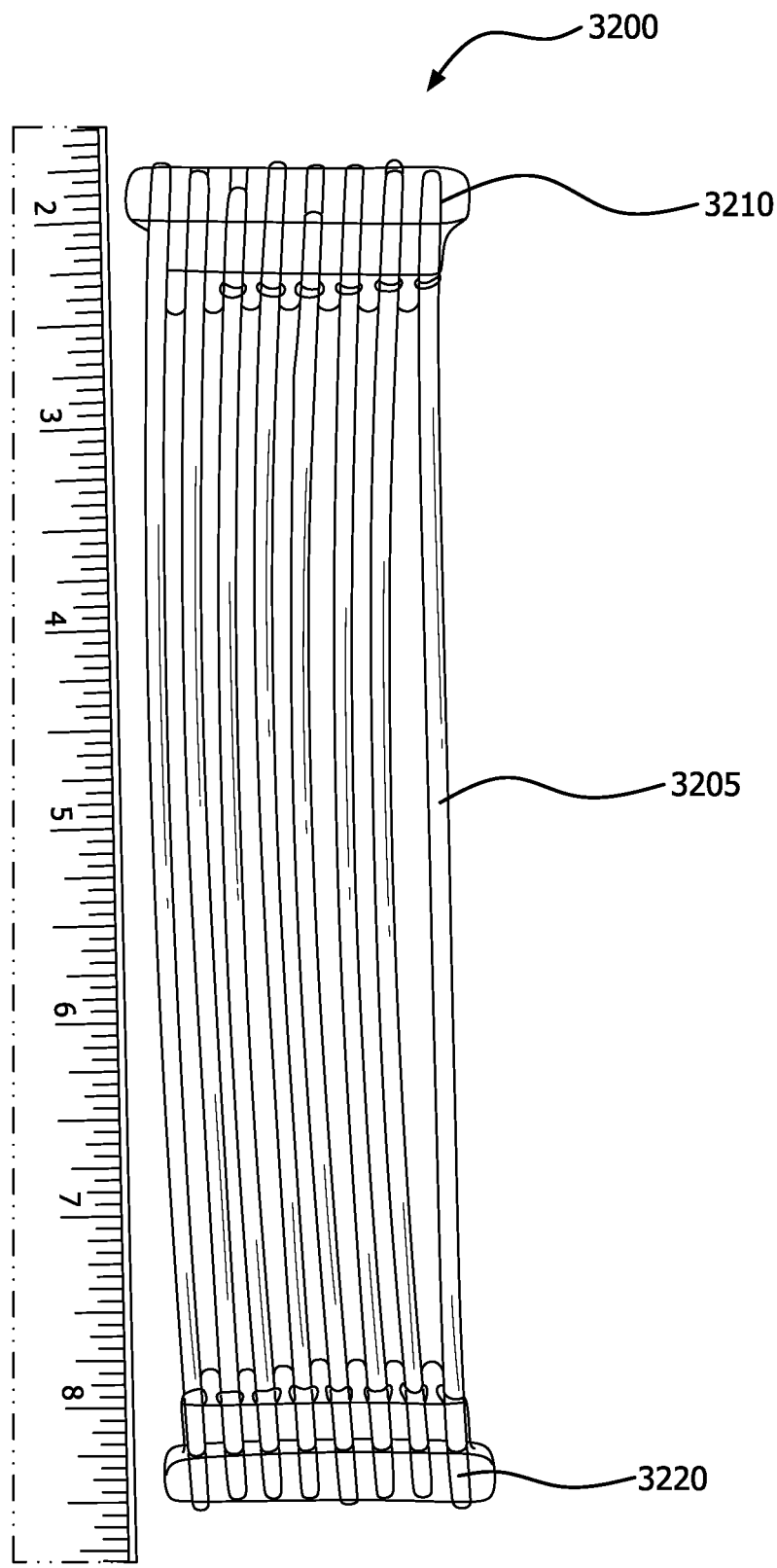
FIGS. 32A and B are schematic illustrations containment tubes connected by an access port on both ends in accordance with some embodiments.
Figure 32B:
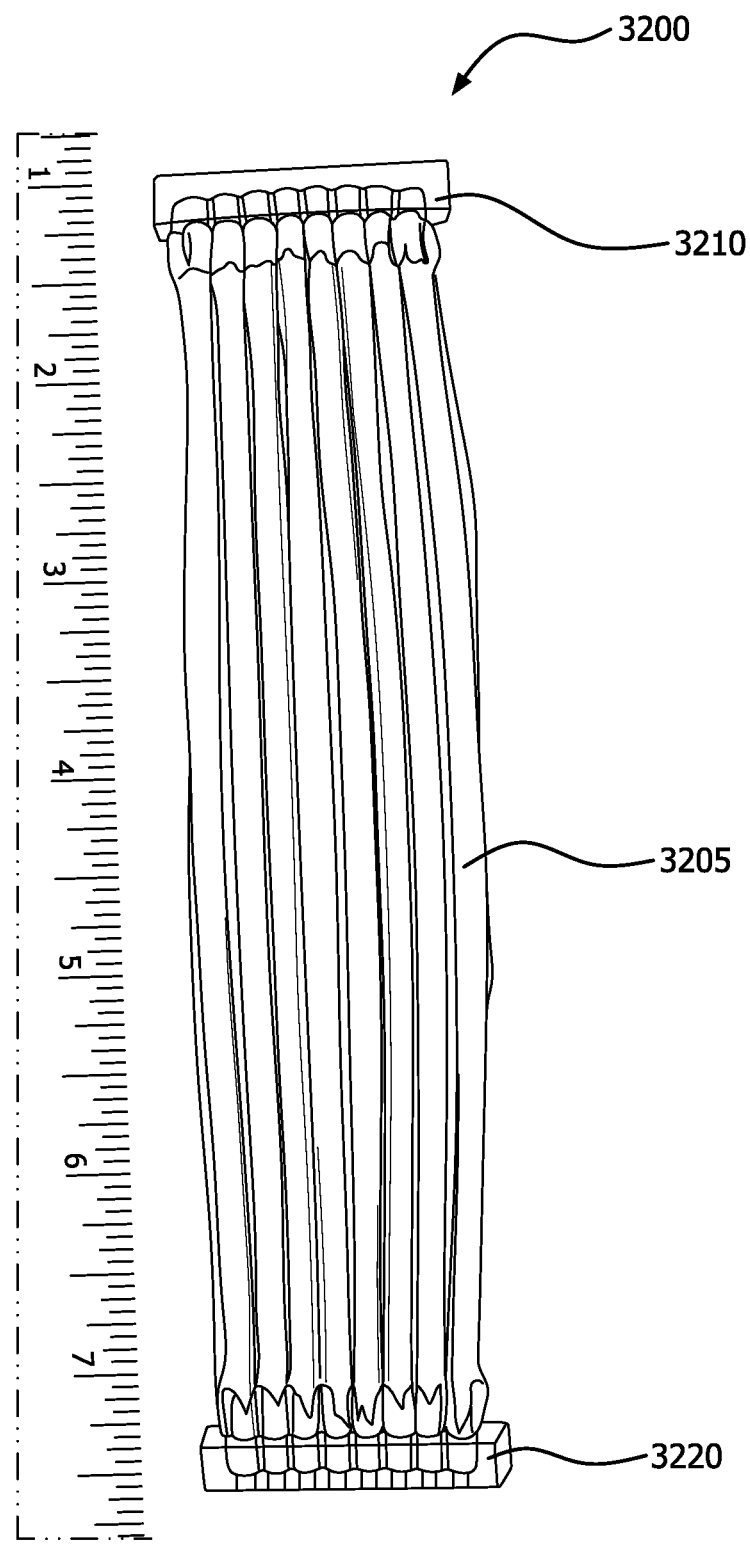

The second access ports provide access points through which one or more therapeutic device (e.g., cell containment member) may be moved in and out of the luminal regions of the containment tubes 1205. The first access ports provide access points through which a fluid stream can be delivered to the luminal region of the containment tubes 1205 to fill and/or flush the luminal region of the plurality of containment tubes 1205. In some embodiments, the fluid stream can be used to fill the luminal region of the containment tubes 1205 with cells, or remove cells from the luminal region. In other embodiments, the fluid stream can be used to push the one or more therapeutic device (e.g., cell containment member) from the luminal regions of the containment tubes 1205 through unsealed first access ports to an area external to the containment tubes 1205. It is to be appreciated that a plurality of containment tubes 3105 may be fluidly connected to each other by a single access port 3110 at one end of the encapsulation device 3100, such as is shown in FIGS. 31A and B, or by an access port 3210, 3220 at both ends of the containment tubes 3205 of the encapsulation device 3200 shown in FIGS. 32A and B.

Turning back to FIG. 12C, the manifold 1235 is constructed of a biocompatible material and includes at least one connection port 1275 in fluid communication with the tube 1240 and flush port 1255. The manifold 1235 further includes a chamber (not depicted) having one or more openings therein such that the manifold 1235 is in fluid communication with the second access ports and with the luminal region of each of the containment tubes 1205. In embodiments in which the chamber includes a plurality of openings, each of the openings of the manifold 1235 is aligned with the access port of each of the containment tubes 1205.

In some embodiments, the flush port 1255 and tube 1240 may be aligned in a same horizontal plane as the containment tubes 1205 (as shown in FIG. 12C). In other embodiments, the tube 1240 may have an elbow or angle (e.g., 30°, 45°, or 90°) such that the tube 1240 extends through the horizontal plane of the containment tubes 1205 (not shown). The plurality of containment tubes 1205 may be individually affixed (e.g., permanently bonded or resealable) to an end of the manifold 1235 and movable as a group.

In some embodiments, the containment tube 1240 is constructed of a biocompatible material having a length that is substantially equal to a length of the containment tubes 1205 such that a proximal end of the containment tube 1240 with the resealable cap 1245 resides near or adjacent to the proximal end of the containment tubes 1205 (and/or at or near the proximal end 1215 of the encapsulation device 1200), particularly when the encapsulation device is implanted in a patient. In some embodiments, the containment tubes 1205 may be constructed with a composite material having a cell retention layer and vascularizing layer as described herein.

The resealable port 1225 can have any shape suitable for facilitating placement, retrieval, and replacement of one or more cell containment member in the luminal regions of the containment tubes 1205. In some embodiments, the resealable port 1225 is a hollow fitting (e.g., made of PTFE) having a first portion that fits snugly inside ends of the containment tubes 1205 and a second portion that extends beyond the ends of the containment tubes 1205 to receive and retain a sealing element. In some embodiments, the resealable port 1225 can be fabricated by injection molding of a fitting onto the ends of the containment tubes 1205 using techniques known to those skilled in the art.

Additionally, the resealable port 1225 and flush port 1255 can be repeatedly opened and closed with a seal. As discussed above, the seal includes, but is not limited to, caps, plugs, clamps, compression rings, or valves. The seal may be attached to the resealable port 1225 with friction, by clamping, or with a screw comprised of threads and grooves. Depending on the intended use of the encapsulation device 1200, the resealable port 1225 and/or flush port 1255 is sealed to create a hermetical seal, a fluid-tight seal, or a non-fluid-tight seal. An encapsulation device 1200 intended for permanent or long term (e.g., at least about three weeks) implantation in a patient, may be sealed with a hermetical or a fluid-tight seal.

Figure 12D:
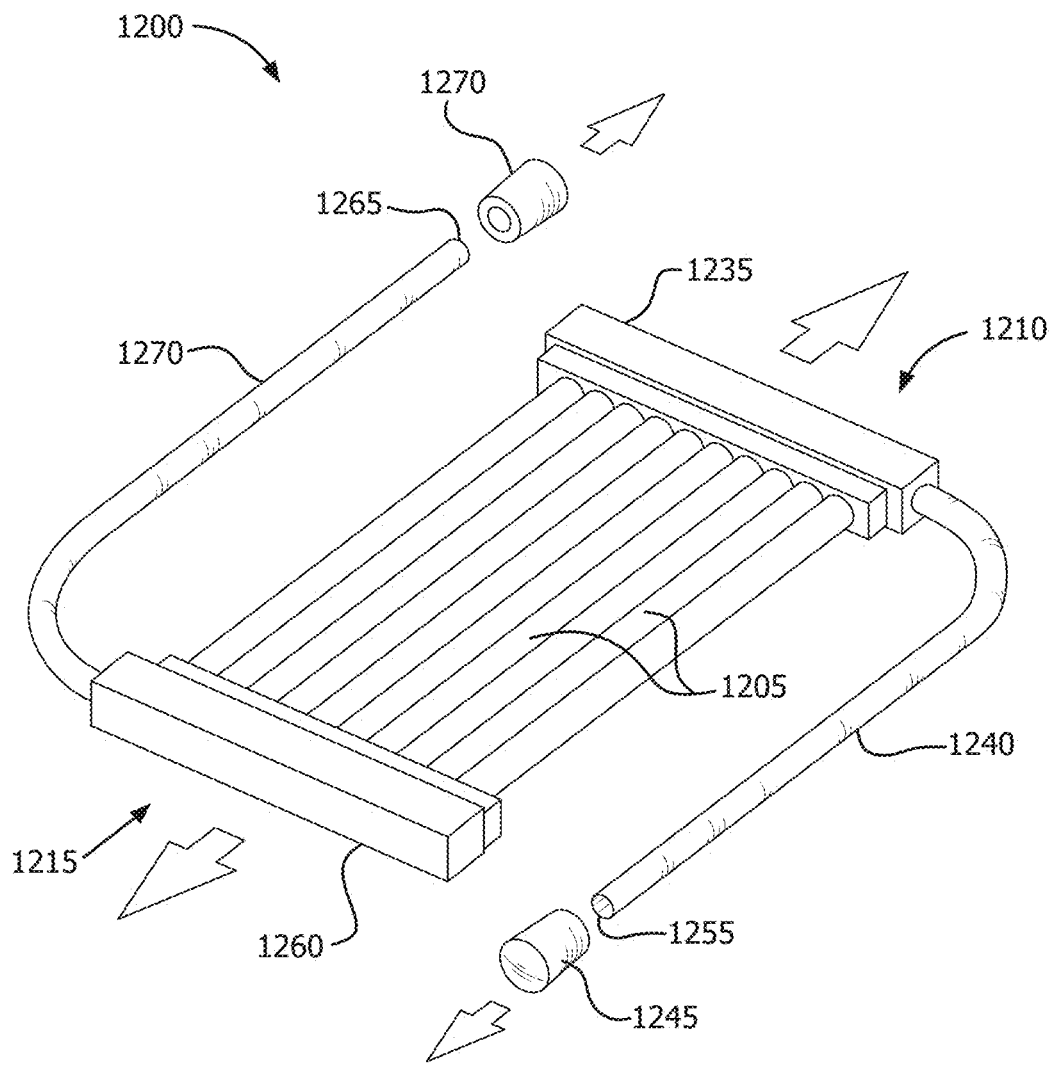
FIG. 12D is a schematic illustration of an encapsulation device having a plurality of containment tubes and a manifold (with a flush port) located at both the distal and proximal ends thereof in accordance with some embodiments.

In an alternate embodiment depicted in FIG. 12D, the encapsulation device 1200 has first manifold 1235 fluidly connecting the first access ports at the distal end 1210 and a second manifold 1260 fluidly connecting the second access ports at the proximal end 1215. The first and second manifolds 1235, 1260 are fluidly connected to a first flush port 1255 and a second flush port 1265, respectively, by tube 1240 and tube 1270. When not in use, resealable caps 1245, 1270 may cover and seal the flush ports 1255, 1265. The access ports on either the proximal end 1215 or the distal end 1210 can be used to provide an access point through which one or more cell containment member (or other therapeutic device) or cells may be moved in and out of the luminal regions of the containment tubes 1205.

Figure 12E:
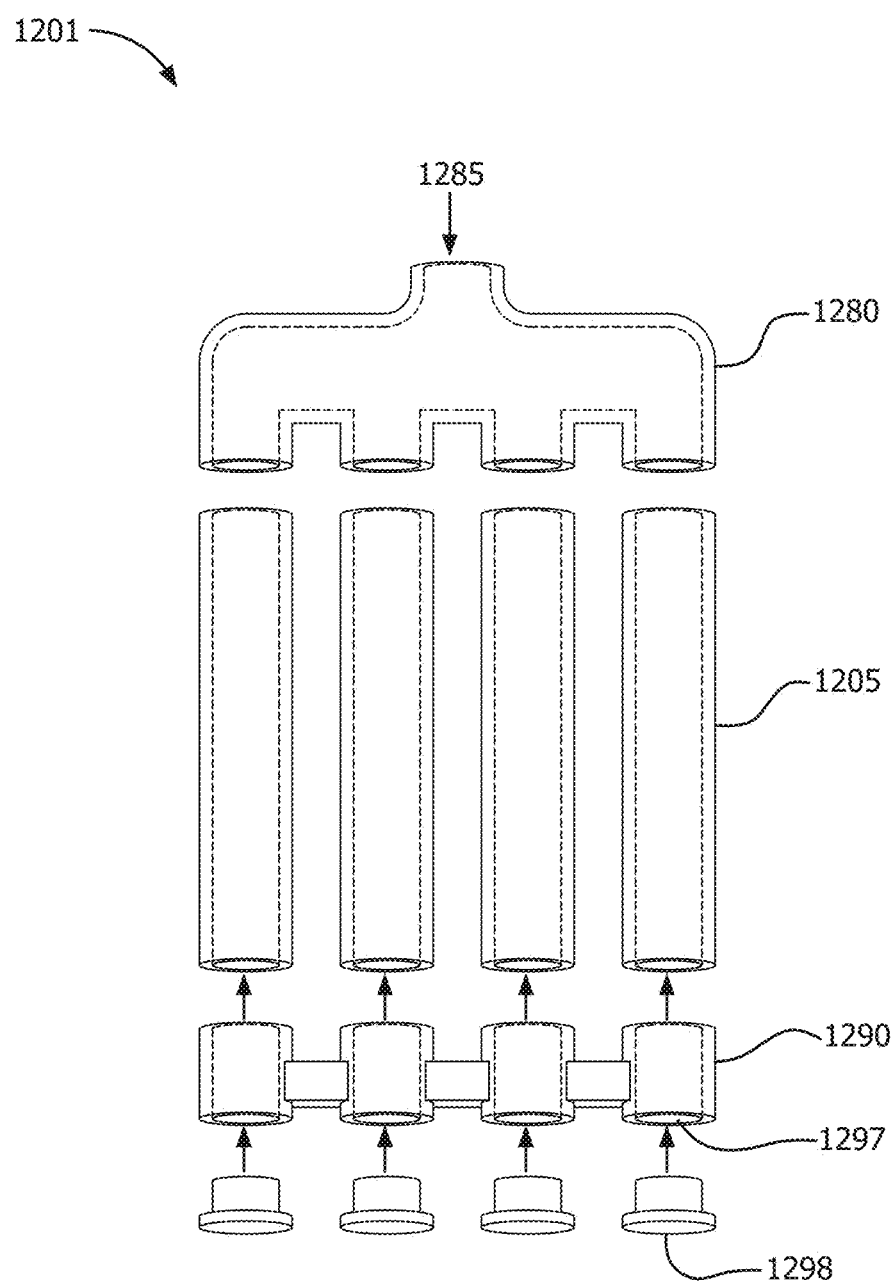
FIG. 12E is a schematic illustration of an encapsulation device that includes a manifold with a top access port on a first end and a resealable (or permanent) port on a second end in accordance with some embodiments.
Figure 12F:
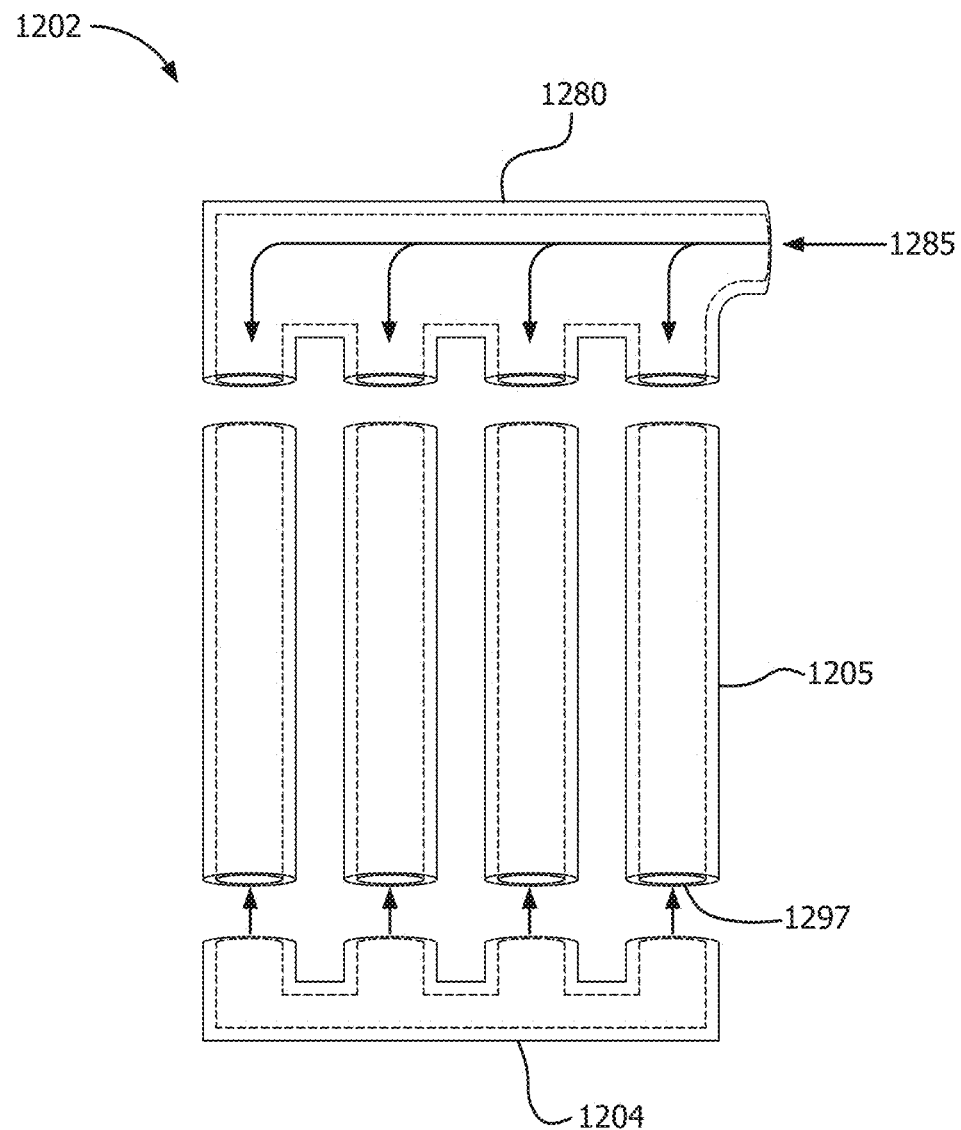
FIG. 12F is a schematic illustration of an encapsulation device that includes a manifold having a side access port on a first end and a resealable (or permanent) port on a second end in accordance with some embodiments.
Figure 12G:
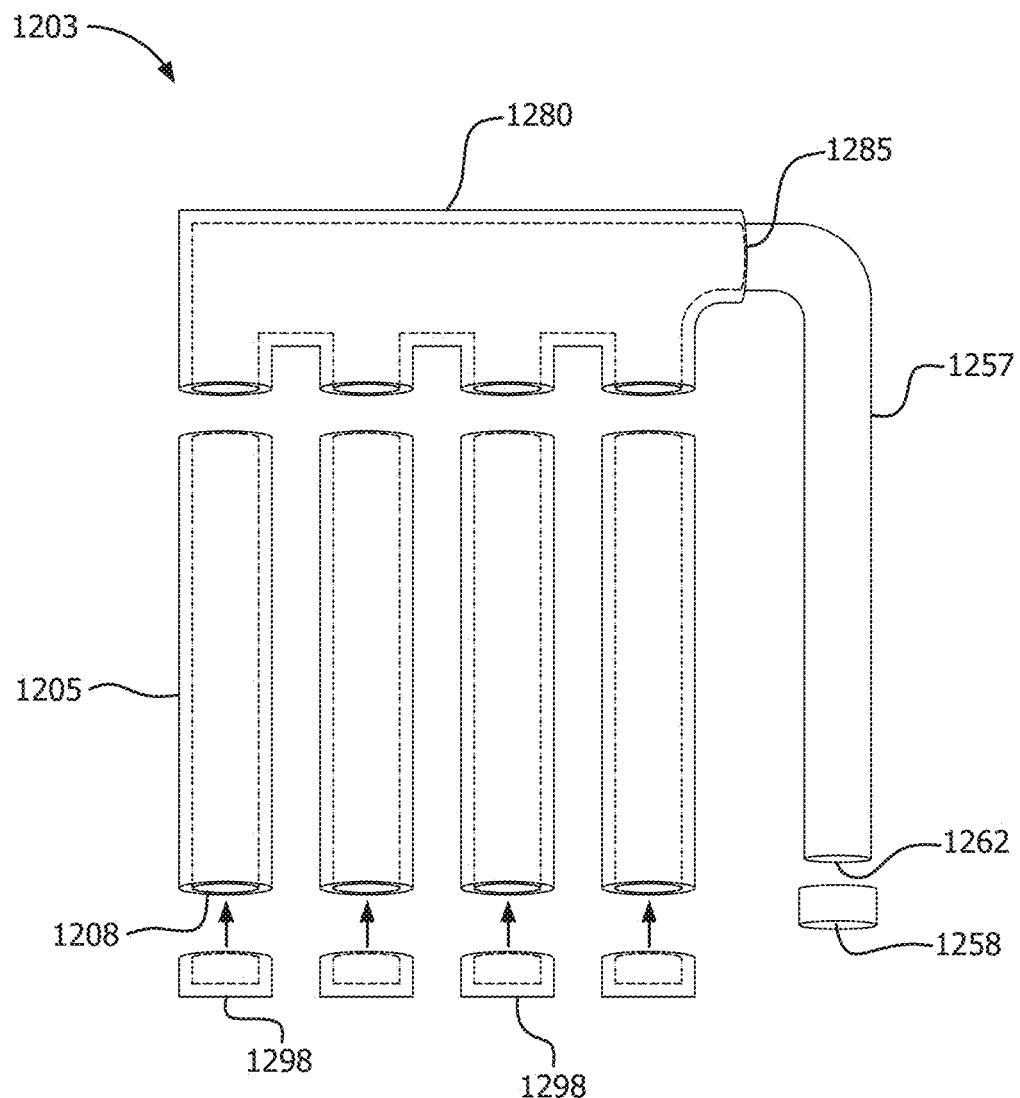
FIG. 12G is a schematic illustration of an encapsulation device that includes a manifold having a side access port at a first end, a flush port fluidly connected to the side access port, and resealable (or permanent) caps at a second end in accordance with some embodiments.

FIG. 12E-12G depict various manifolds and seals that may be used in conjunction with encapsulation devices described herein. For instance, FIG. 12E depicts an encapsulation device 1201 that includes a manifold 1280 having a top connection port 1285, containment tubes 1205 configured so as to be fluidly connected to the manifold 1280, a resealable connector member 1290 containing access ports 1297, and resealable caps 1298 configured to seal the proximal end of the resealable connector member 1290. The connection port 1285 on either the manifold 1280 or the access ports 1297 on the resealable connector member 1290 can be used to provide an access point through which one or more cell containment member (therapeutic device) or cells may be moved in and out of the luminal regions of the containment tubes 1205.

FIG. 12F depicts an encapsulation device 1202 that includes a manifold 1280 having a side connection port 1285, containment tubes 1205 configured so as to be fluidly connected to the manifold 1280, and a resealable port 1204. The connection port 1285 on the manifold 1280 or access ports 1297 on the containment tubes 1205 can be used to provide an access point through which one or more cell containment member (or other therapeutic device) or cells may be moved in and out of the luminal regions of the containment tubes 1205.

FIG. 12G depicts an encapsulation device 1203 that includes a manifold 1280 having a side connection port 1285 and flush port 1262 attached thereto via a tube 1257, containment tubes 1205 configured so as to be fluidly connected to the manifold 1280, resealable caps 1298 for sealing the proximal end 1215 of the containment tubes 1205, and a resealable cap 1258 for sealing the flush port 1262. The flush port 1262 or access ports 1208 on the containment tubes 1205 can be used to provide an access point through which one or more cell containment member (or other therapeutic device) or cells may be moved in and out of the luminal regions of the containment tubes 1205. In some embodiments, a connector member may be positioned between the containment tubes and the resealable caps (not depicted).

Figure 12H:
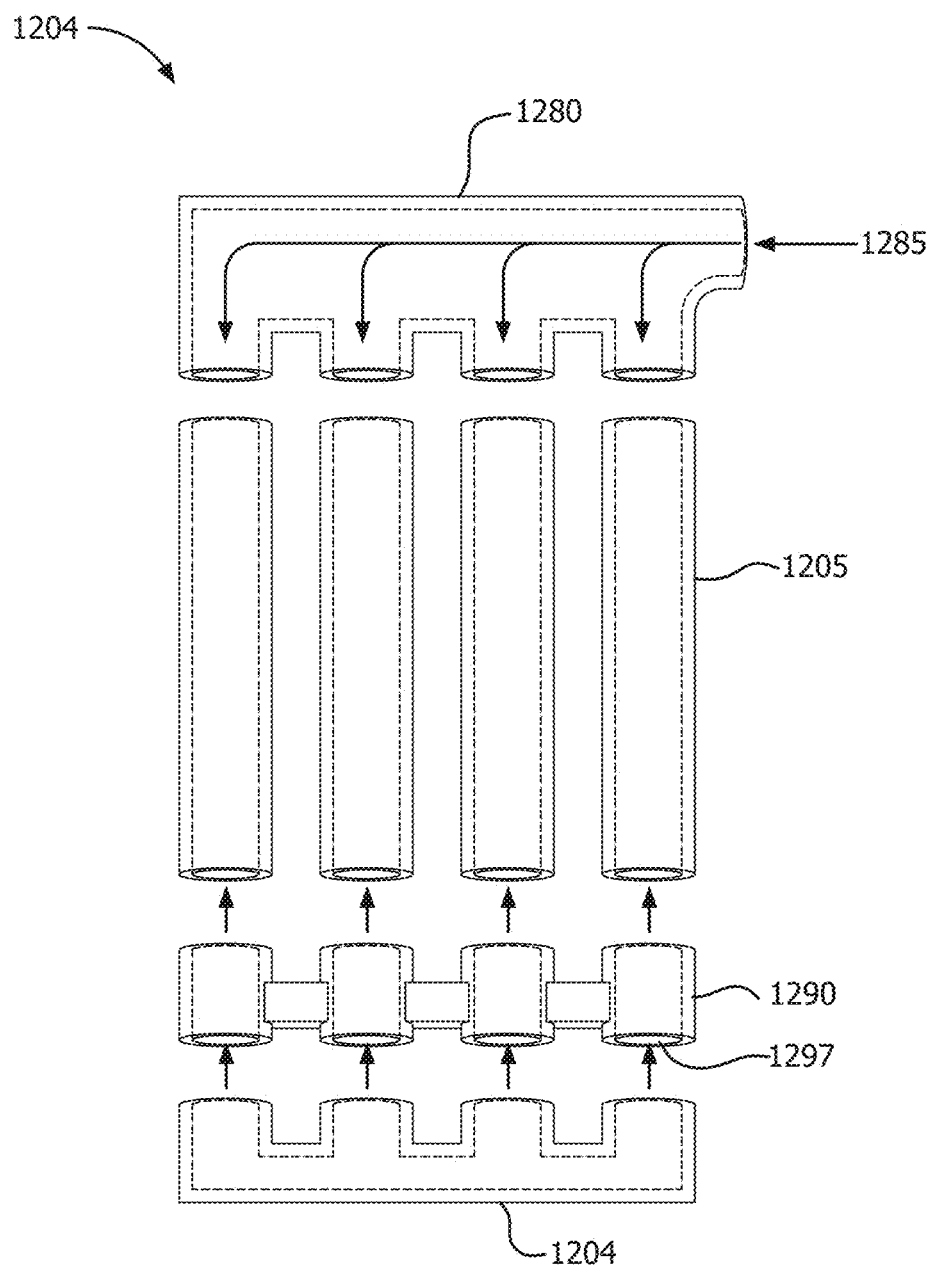
FIG. 12H is a schematic illustration of an encapsulation device that includes a manifold having a side access port on a first end and a connection member and a port (resealable or permanent) on a second end in accordance with some embodiments.

FIG. 12H depicts an encapsulation device 1204 that includes a manifold 1280 having a side connection port 1285, containment tubes 1205 configured so as to be fluidly connected to the manifold 1280, a connector member 1290 (resealable or permanent), and a resealable port 1204. The connection port 1285 on the manifold 1280 or access ports 1297 on the connector member 1290 can be used to provide an access point through which one or more cell containment member (or other therapeutic device) or cells may be moved in and out of the luminal regions of the containment tubes 1205. In such an embodiment, the manifold 1280 may be used to provide a fluid stream to flush the cell containment member(s) out of the containment tubes 1205.

Figure 13A:
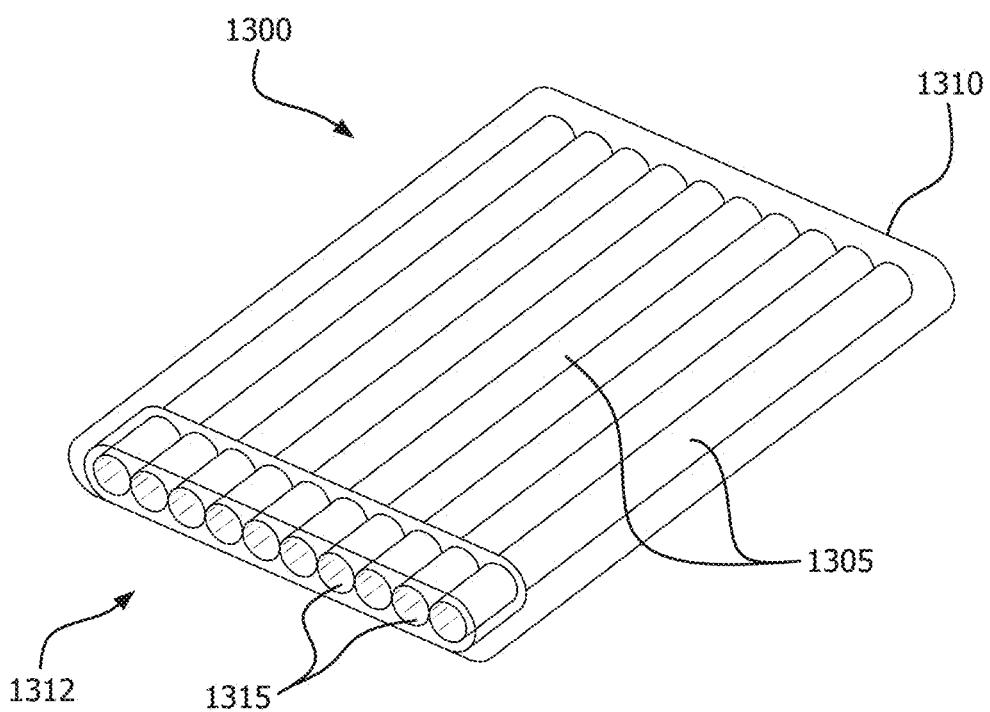
FIGS. 13A and B are schematic illustrations of encapsulation devices including several individual containment tubes grouped together as a single unit in accordance with some embodiments.

Turning to FIGS. 13A, B, and C, in some embodiments, an encapsulation device 1300 can be constructed from several individual containment tubes 1305 grouped together as a single unit. The individual containment tubes 1305 may or may not be fluidly or physically connected with one another. In some embodiments, the containment tubes are connected to each other through connection members. As pictorially shown in FIGS. 13C and D, the containment tubes 1305 may be connected to each other by connection members 1375 that are periodically spaced along the length of the containment tubes 1305 a distance 1320 from each other. The distance 1320 may be the same or different between the connection members 1375. Thus, the periodic spacing may have a regular pattern (e.g., same distance between connection members) or an irregular pattern (e.g., different distances between connection members). It is to be appreciated that FIGS. 13C and D are included herein to visualize the connection members 1375, and that with further preparation, a manifold(s), a resealable port(s), a flush port(s), resealable caps, etc. could be added to the containment tubes 1305.

The attachment of the containment tubes 1305 by the connection members 1375 permit the cell encapsulation device to have flexibility at least between the connection members 1375, while at the same time allowing for stability during implantation. In addition, the separation of containment tubes 1305 in between the connection members 1375 helps the host tissue to integrate fully around and in between the containment tubes 1305. Additionally, the space between the containment tubes 1305 maximizes surface area of tube available for vascularization. The terms "flexible" and "flexibility", as used herein, are meant to describe overall compliance or bending stiffness of the cell encapsulation device and compliance of the host interface/ingrowth layers in contact with the host tissue, such that those ingrowth layers match the compliance of the host tissue as well as the compliance of the cell encapsulation device relative to the host tissue such that the cell encapsulation device can flex and move with the host tissue without an excessive inflammatory response due to a significant mismatch in the compliance of the device and host interface/ingrowth layers with the host tissue.

In some embodiments, the connection members 1375 may be formed of, or include, a bio-absorbable material. The bio-absorbable material degrades and resorbs into the body after the cell encapsulation device 1300 is placed in the body. There should be little or no degradation prior to implantation. In some embodiments only a portion of the connection members 1374 is formed from the bio-absorbable material, such that when the bio-absorbable material resorbs, the cell encapsulation device 1300 retains some structure for housing the cells or therapeutic devices within the containment tubes 1305. In other embodiments, the bio-absorbable material makes up all, or substantially all, of the connection members 1375 such that no connection members 1375 remain after the bio-absorbable material resorbs. By re-absorbing the connection members 1375, the containment tubes 1305 are no longer restrained and are independently movable. As discussed above, the separation of the containment tubes 1305 helps the host tissue to integrate fully around and in between the containment tubes, and maximizes surface area of tube available for vascularization. Additionally, the lack of connection members 1375, either deliberately or through bio-absorption enables an easier removal of the cell encapsulation device. For instance, growth of tissue onto and/or into the connection members 1375 can act as a barb and hinder or restrict the ease of explant/removal of the cell encapsulation device.

The bio-absorbable material may fully resorb quickly (e.g., in only a few days or months) or may require significantly longer (e.g. years) to fully resorb. The resorption rate of the bio-absorbable material depends on the identity of the material and the biological environment and can be selected by a person skilled in the art as needed. The bio-absorbable material may be formed as a solid (molded, extruded, or crystals), a coating (e.g. on the containment tubes), a self-cohered web, a raised webbing, or a screen. Advantageously, certain bio-absorbable materials provide a slow bio-absorption profile that can be used to instruct vascularization and other tissue ingrowth into the connection members at the implantation site. For example, the bio-absorption profile may be slower than the rate of vascularization. In addition, a slow degradation profile may allow for ease of explant/removal of the cell encapsulation device.

Figure 13B:
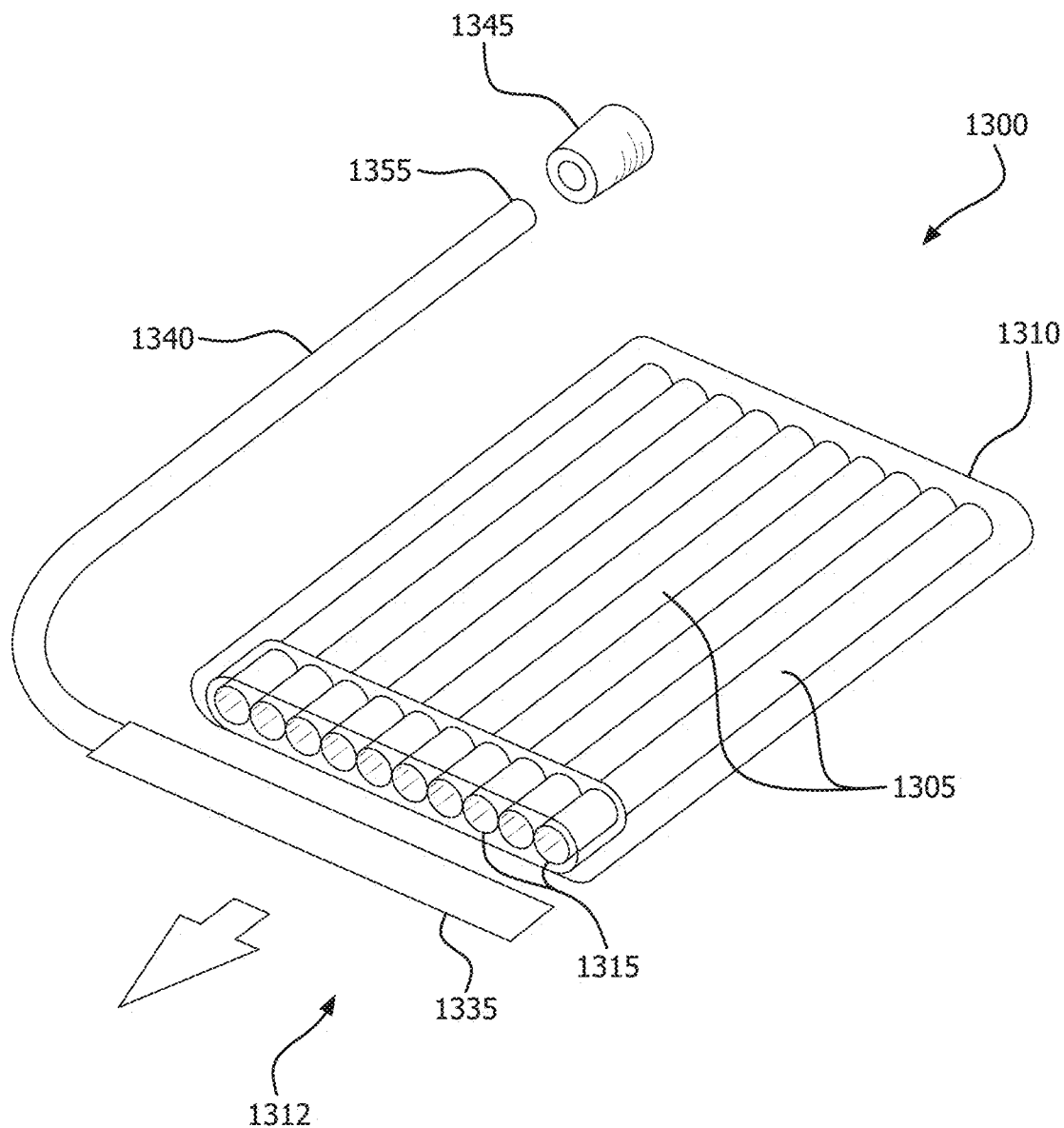
FIGS. 13C and D are schematic illustrations depicting containment tubes connected to each other at various points along their lengths in accordance with some embodiments.
FIG. 13E is a schematic illustration of an encapsulation device with a resealable port at one end thereof and containment tubes connected to each other a various points along their lengths.
FIG. 13F is a schematic illustration of an encapsulation device with a manifold and flush port at one end thereof and containment tubes connected to each other a various points along their lengths.
Figure 13C:
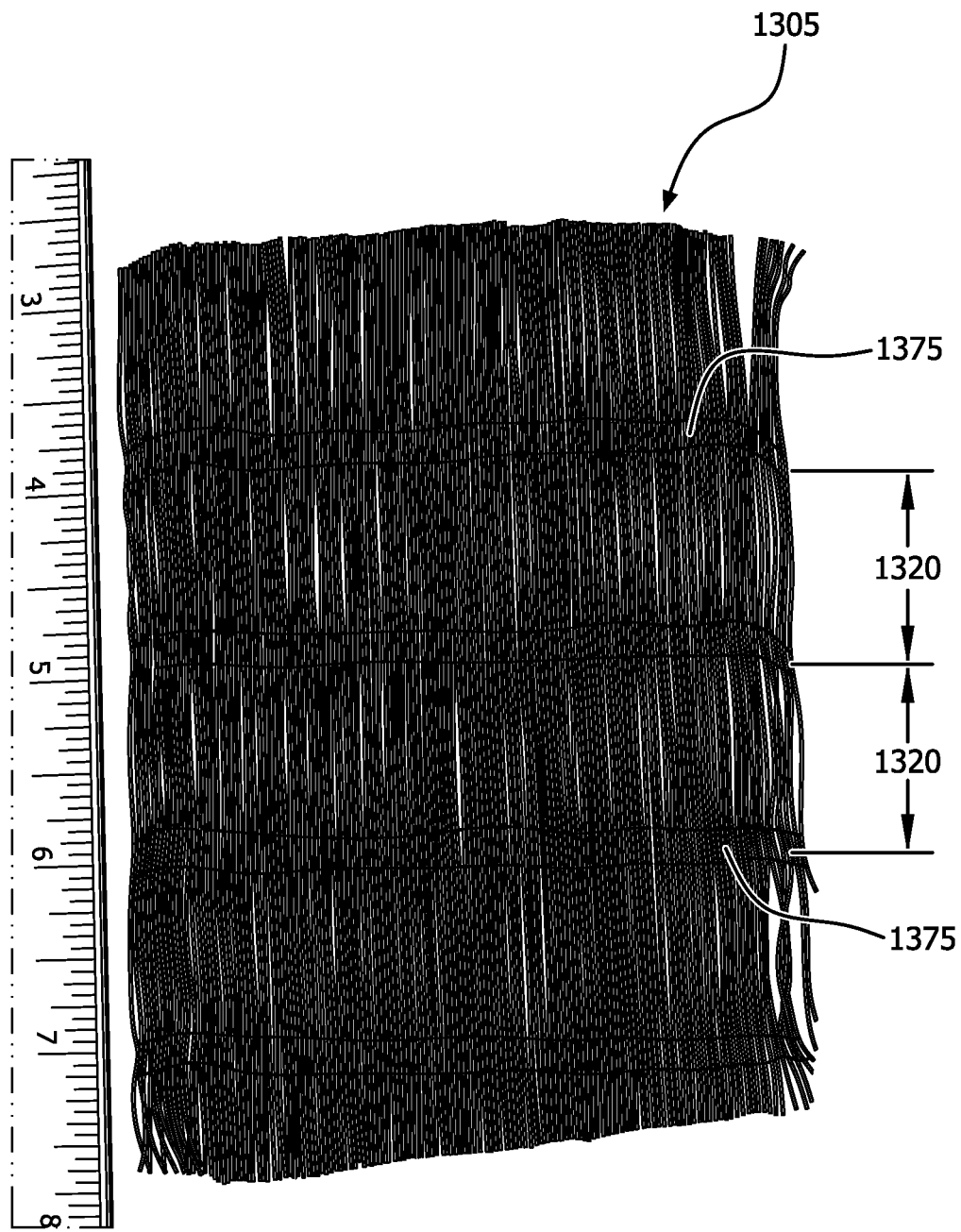
Figure 13D:
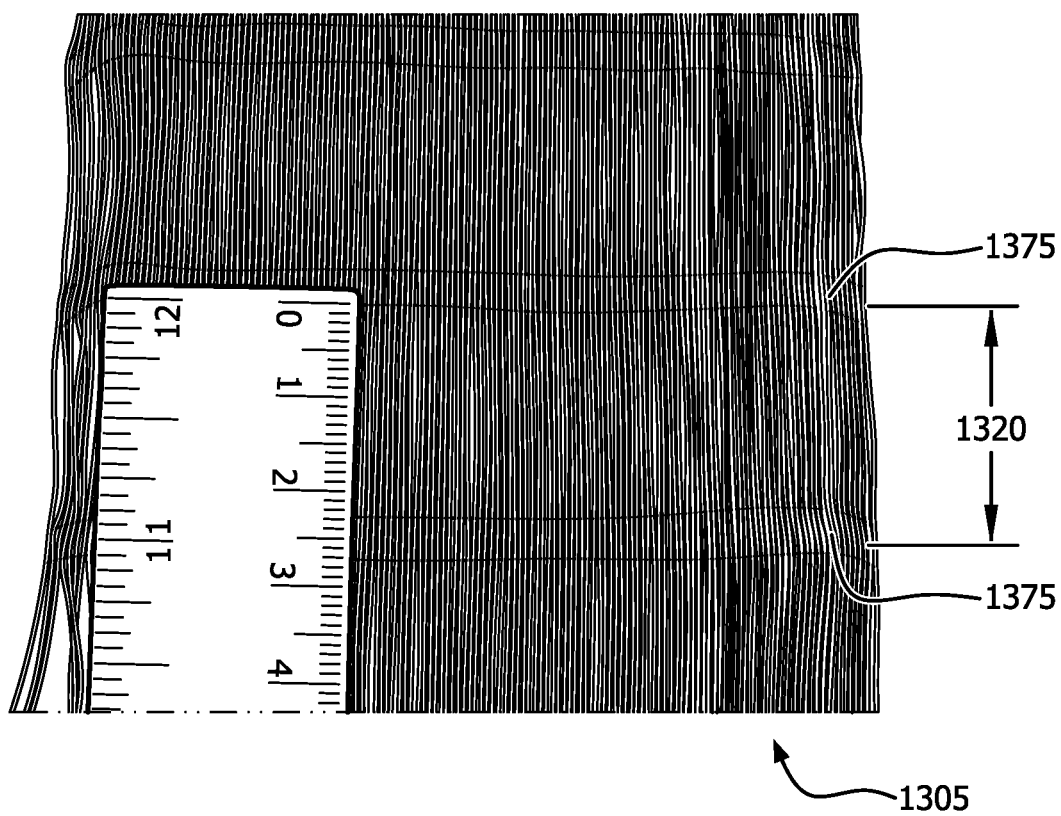
Figure 13E:
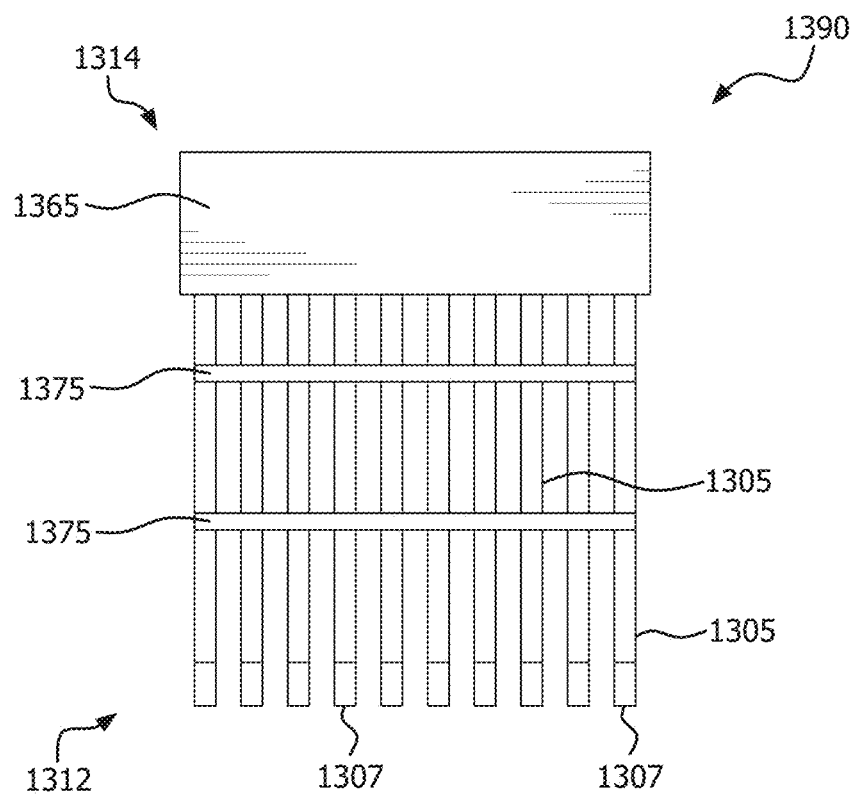
Figure 13F:
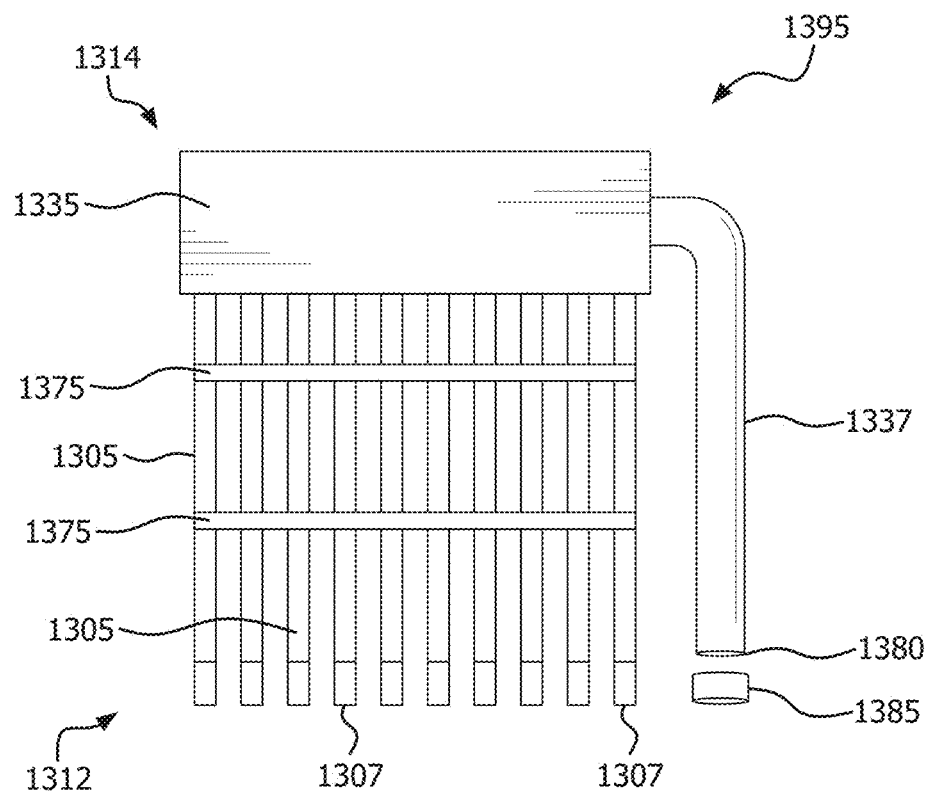

FIG. 13E schematically depicts a resealable port 1365 at a proximal end 1314 of the cell encapsulation device 1390. It is to be appreciated that a resealable port (not depicted) or resealable caps may be affixed to the distal end of the cell encapsulation device 1390 to seal the access ports of the containment tubes 1305 located at the distal end. FIG. 13E depicts the use of resealable caps 1307 for ease of illustration. FIG. 14F schematically depicts a removable manifold 1335 to fluidly connect the access ports of the containment tubes 1305 of the cell encapsulation device 1395. A flush port 1380 may be fluidly connected to the manifold 1335 via a tube 1337. When not in use, a resealable cap 1385 may cover and seal the flush port 1380. It is to be appreciated that a resealable port (not depicted) or resealable caps may be affixed to the distal end of the cell encapsulation device 1390 to seal the access ports of the containment tubes 1305 located at the distal end. FIG. 13F depicts the use of resealable caps 1307 for ease of illustration. The distance between connection members 1375 may be from 0.25 mm to about 10 cm, from about 0.50 mm to about 8 cm, from about 0.75 mm to about 5 cm, from about 1 mm to about 2 cm. It is to be noted that these distances are applicable to each of the embodiments described herein where containment tubes and/or channels are interconnected. In some embodiments, the individual containment tubes 1305 can be fully connected to each other along their entire lengths for a least compliant, or stiff, arrangement (not depicted). The access ports 1315 may be used to move one or more cell containment member (therapeutic device) or cells in and out of the luminal regions of the containment tubes 1305.

Turning to FIG. 13B, a removable manifold 1335 may be used to fluidly connect the access ports 1315 at the distal end 1312 of the encapsulation device 1300. A flush port 1355 may be fluidly connected to the manifold 1335 via a tube 1340. When not in use, a resealable cap 1345 may cover and seal the flush port 1355. The access ports 1315 provide access points through which a fluid stream can be delivered to the luminal region of the containment tubes 1305 to fill the luminal region of the containment tubes 1305. In some embodiments, the fluid stream can be used to fill the luminal region of the containment tubes 1305 with cells. In some embodiments, and as shown in FIGS. 13A and B, the containment tubes 1305 are encompassed or overmolded with a biocompatible material 1310 around their periphery to hold the containment tubes in a tight, permanent configuration. In some embodiments, the containment tubes 1305 may be constructed with a composite material having a cell retention layer and vascularizing layer as described herein. In some embodiments a woven or non-woven textile or knit may be overlayed on the cell encapsulation device 1300. In another embodiment, the woven or non-woven textile or knit may be periodically attached to the cell encapsulation device 1300. The woven or non-woven textile or knit may serve as a restraining layer and may aid in tissue ingrowth or attachment. In addition, the woven or non-woven textile or knit may provide mechanical support for handleability, implantation, and removal of the cell encapsulation device.

Figure 14A:
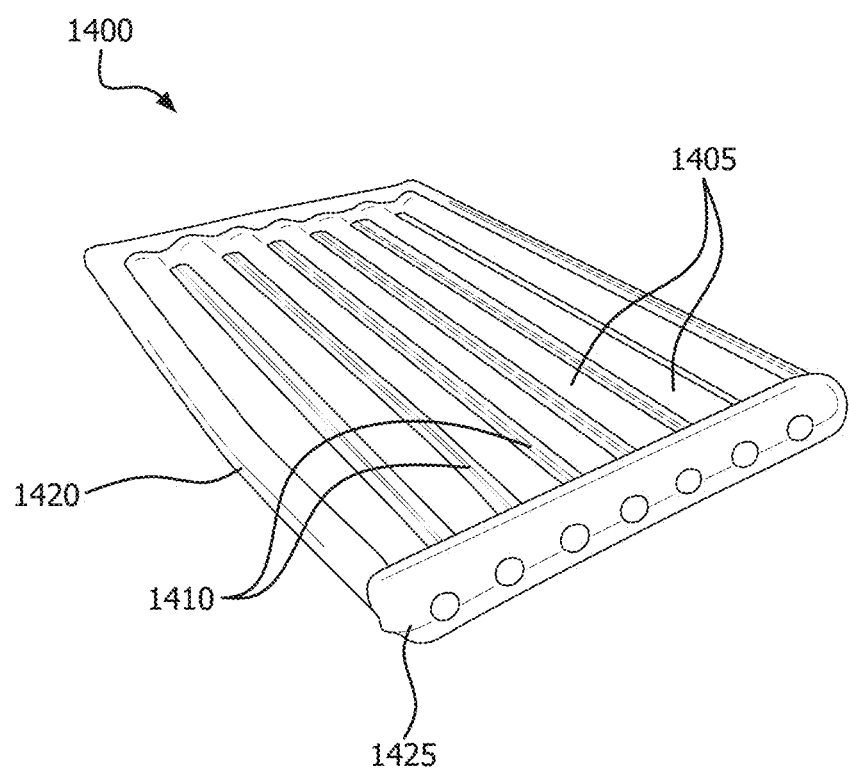
FIG. 14A is a schematic illustration of an encapsulation device constructed from several channels in accordance with some embodiments.
Figure 14B:
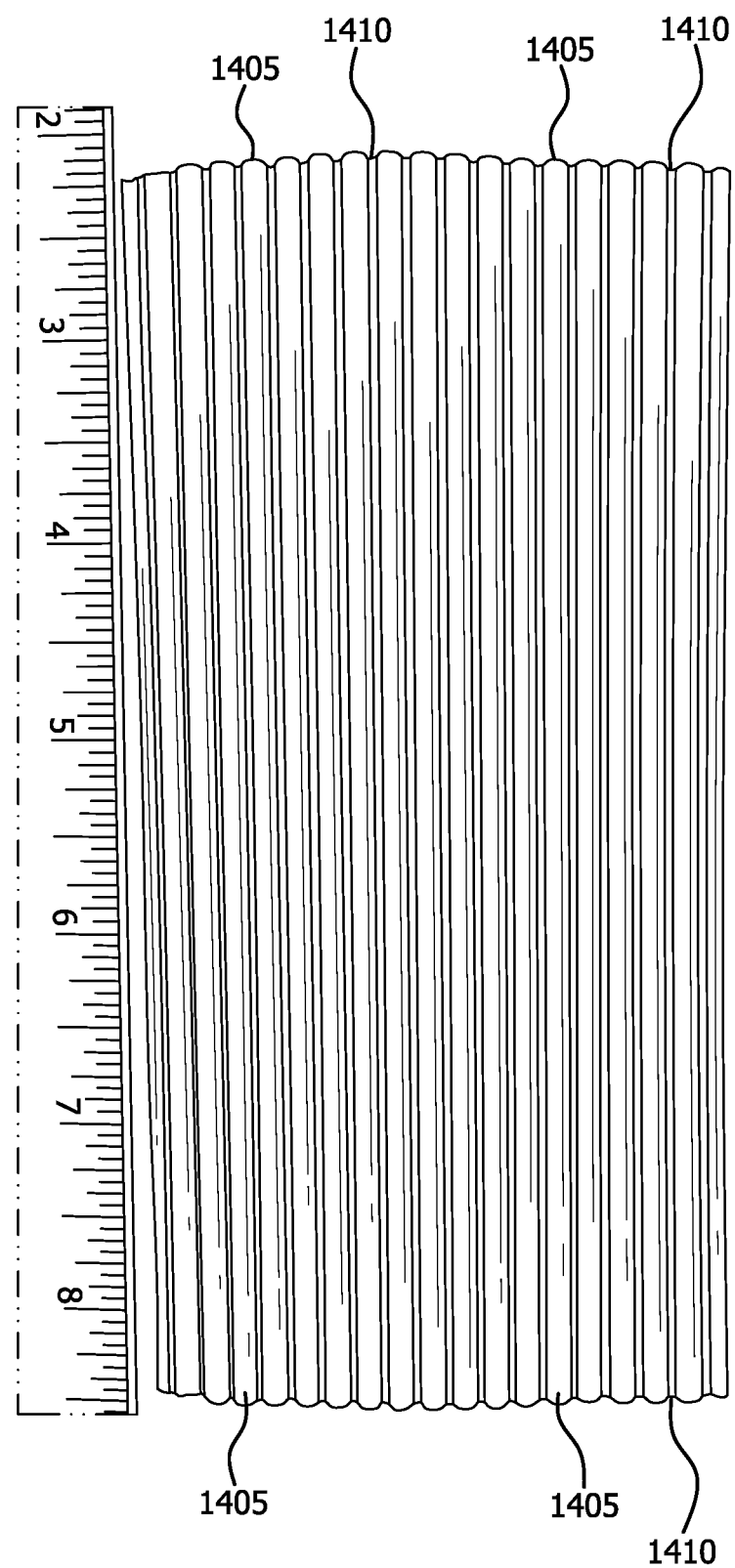
FIG. 14B is a schematic illustration depicting a containment channels having seams between each containment channel in accordance with some embodiments.

Turning now to FIGS. 14A and B, an encapsulation device 1400 may be constructed from a laminate formed by adhering several layers of a polymeric material(s) together. The layers of polymeric material used to form the laminate may be the same layers of polymeric material used to construct the containment tubes as described herein, and may be constructed with a composite layer that has a cell retention layer and vascularizing layer as described herein. The cell encapsulation device 1400 contains containment channels 1405 with seams 1410 interposed between each containment channel 1405. The containment channels 1405 may be connected with one another such that each containment channel is separate and fluidly isolated from the other containment channels, such as is pictorially depicted in FIG. 14B. Alternatively, or in addition to, the containment channels 1405 may be connected with one another such that the containment channels are in fluid communication with one another. For example, the channels 1405 can be connected to each other along their entire lengths to fluidly isolate each of the channels from one another, or the containment channels 1405 may be interconnected to each other at spaced (or varying) intervals along their lengths to provide interconnection channels to fluidly connect adjacent containment channels (not depicted). Some containment channels may be isolated from each other while some adjacent containment channels may be fluidly connected at one or more point along their lengths (not depicted). In some embodiments where the layers of material are adhered, porosity may be maintained to allow for tissue attachment and/or vascularization within the seams 1410.

In other embodiments, the seams 1410 may include unattached regions between the adjacent containment channels 1405 to allow for tissue attachment and/or vascularization. The containment channels 1405 may be sealed at one or both ends by adhering the layers of material at the one or both ends. In some embodiments, the layers of material are over-molded with silicone 1420 around the periphery. In one embodiment, a manifold 1425 may be fluidly connected to the containment channels 1405 to provide access to the lumens of the channels for the placement of cells or a cell containment member. In some embodiments, a woven or non-woven textile or knit may be built intrinsically into the laminate to provide enhanced mechanical support for handleability, implantation, and removal of the cell encapsulation device.

Figure 15:
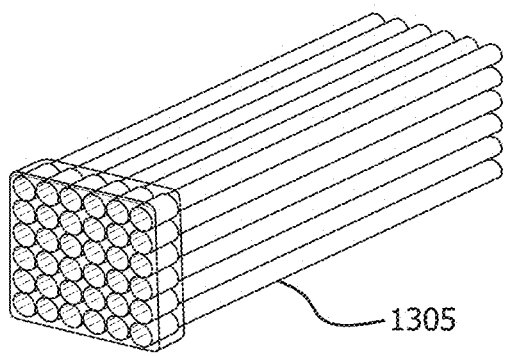
Figure 16:
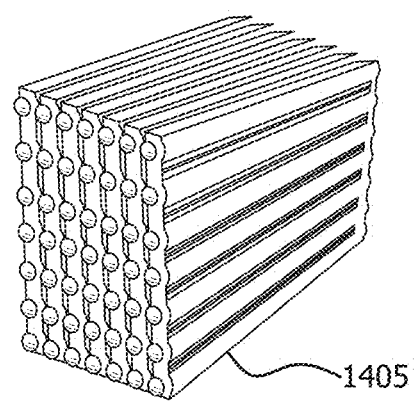
Figure 17A:
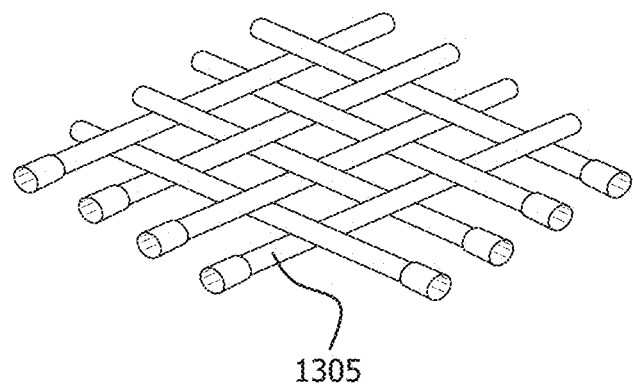

In either arrangement depicted in FIGS. 13A and B or FIGS. 14A and B, the containment tubes 1305 or containment channels 1405 may be layered such that the containment tubes 1305 or containment channels 1405 are parallel or substantially parallel to each other along a length of the implantable apparatus. In some embodiments, the containment tubes 1305 or containment channels 1405 are in a same horizontal plane. In embodiments in which the containment tubes 1305 or containment channels 1405 include a shaping element, the containment tubes 1305 or containment channels 1405 are non-planar (i.e., not planar, not lying in a single plane) or provided in various planes. Alternative to the two dimensional layering arrangements shown in FIGS. 13A and B or FIGS. 14A and B, the containment tubes 1305 or containment channels 1405 may be stacked in a three dimensional arrangement as shown in FIGS. 15 and 16, or staggered in a three dimensional arrangement, for example a woven mesh configuration, as shown in FIG. 17A. The three dimensional arrangements can be used to provide the containment tubes 1305 or channels 1405 in a stacked or a staggered (in the x, y, and/or z direction) orientation.

Figure 17B:
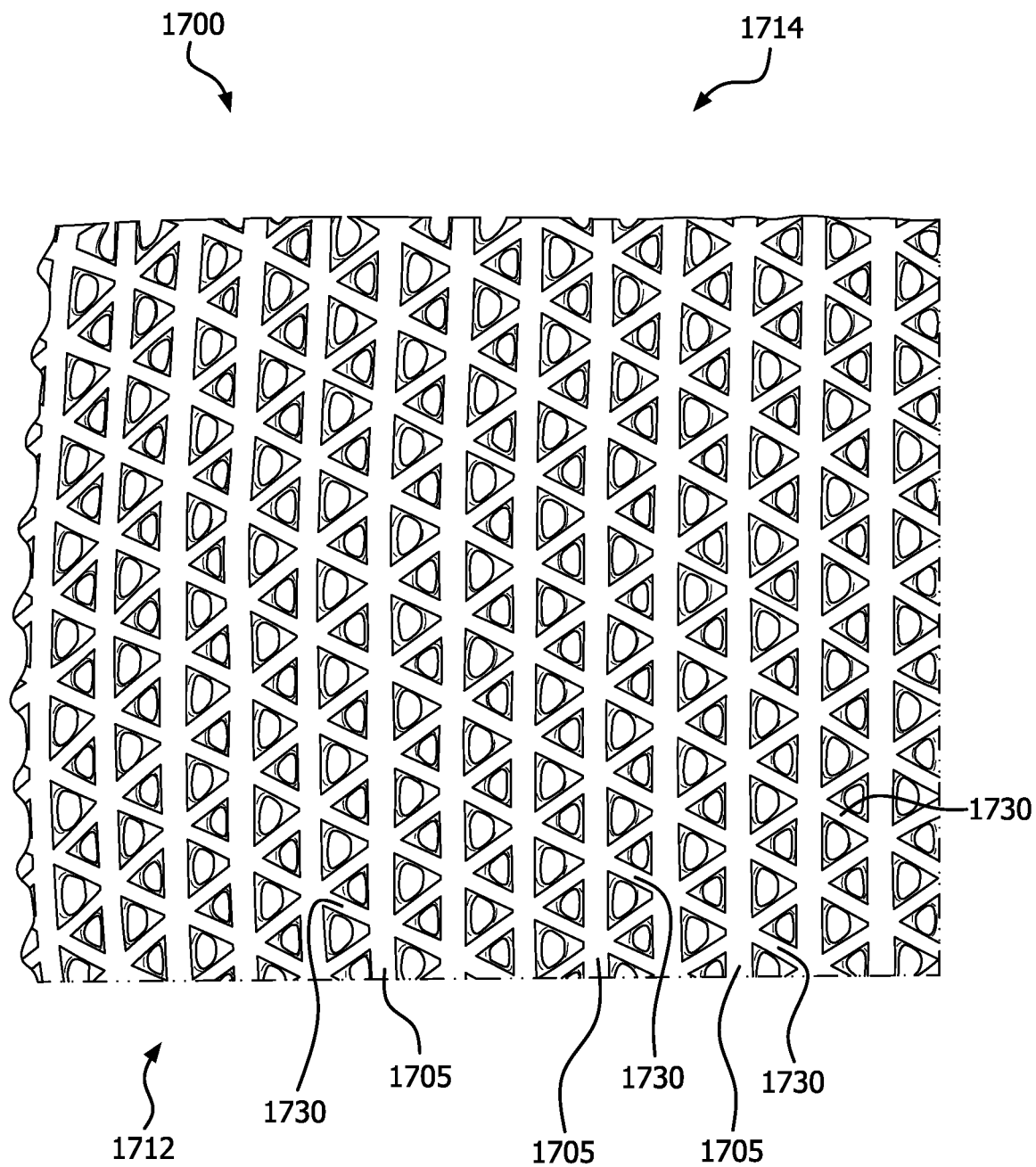
FIG. 17B is a schematic illustration of containment tubes having a substantially planar arrangement with off-axis interconnection members in accordance with some embodiments.

In a further embodiment depicted in FIG. 17B, the containment tubes 1705 (or channels (not depicted)) may have a substantially planar arrangement with off-axis interconnection members 1730 to form a lattice configuration. "Off-axis", as used herein, is meant to describe interconnection members 1730 that are connected to the containment tubes 1705 at an angle greater than zero degrees and less than 90 degrees. In the cell encapsulation device depicted in FIG. 17B, the interconnection members 1730 are oriented at an angle about 45 degrees with respect to the containment tubes 1705 to form the lattice configuration. The containment tubes 1705 are fluidly connected to each other through the interconnection members 1730. Thus, flow into one containment tube 1705 may pass through the interconnection members 1730 into an adjacent containment tube(s) 1705. In such a "'lattice" embodiment, the containment tubes 1705 contains cells directly, and do not typically contain a therapeutic device, although containing a therapeutic device is not prohibited. Although not depicted, a manifold(s), a resealable port(s), or resealable caps(s) may be positioned on the distal end 1712 or the proximal end 1714.

Figure 17C:
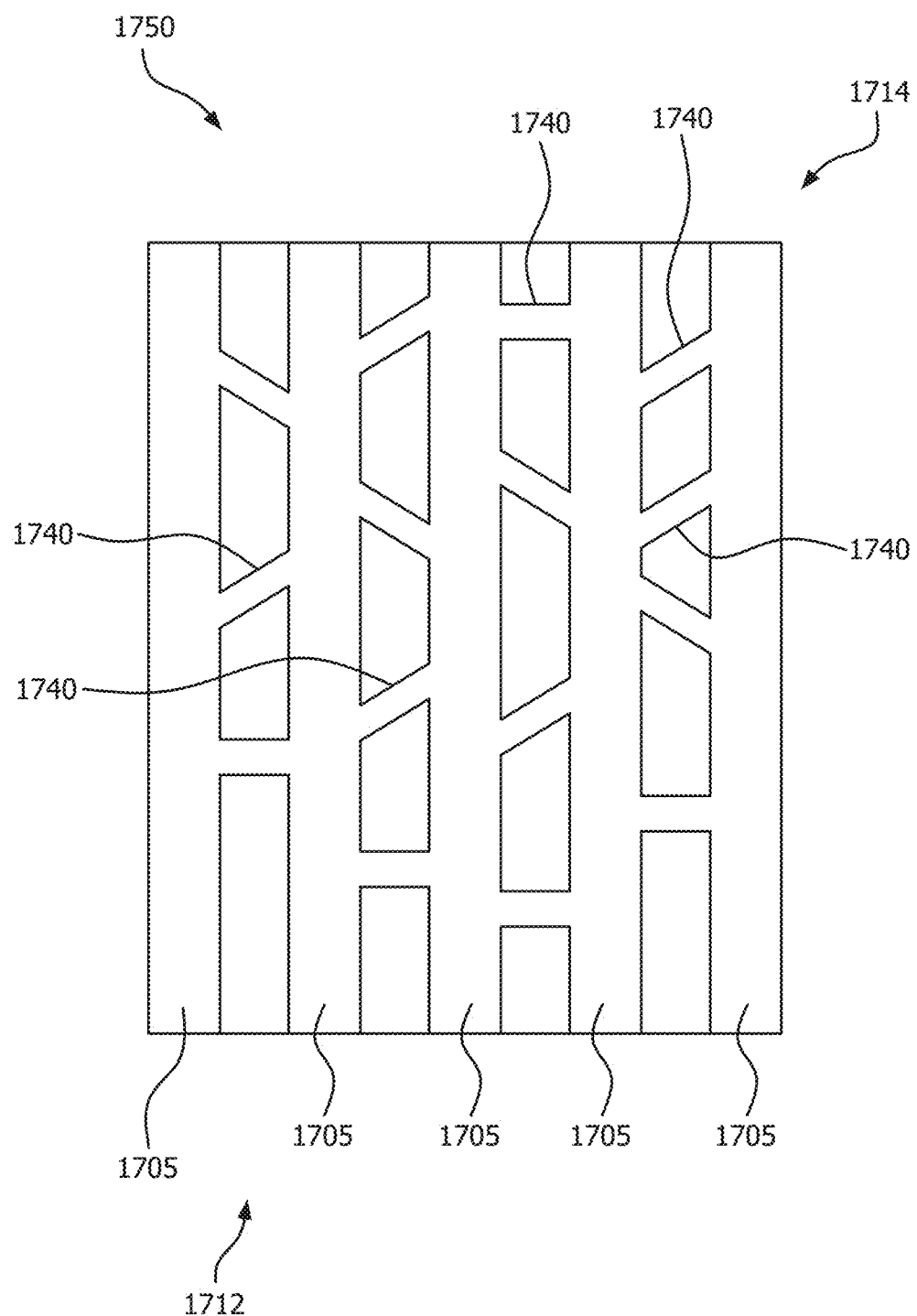
FIG. 17C is a schematic illustration depicting a cell encapsulation member having containment tubes fluidly connected by interconnection members.

In another embodiment, depicted generally in FIG. 17C, a cell encapsulation device 1750 may include containment tubes interconnected by interconnection members 1740 that have any orientation, e.g., off-axis or perpendicular with respect to the containment tubes 1705. As shown in FIG. 17C, the interconnection members 1740 connect the containment tubes 1705 at various angles as well as perpendicular to the containment tubes 1705, giving the cell encapsulation device 1750 a more random configuration of interconnection members 1740. The containment tubes 1705 are fluidly connected to each other through the interconnection members 1740. Thus, flow into one containment tube 1705 may pass through the interconnection members 1740 into an adjacent containment tube(s) 1705. Also, the cell encapsulation device 1750 generally contain cells, although the inclusion of one or more therapeutic device in the containment tubes 1705 is not prohibited. Although not depicted, a manifold(s), a resealable port(s), or resealable caps(s) may be positioned on the distal end 1712 or the proximal end 1714.

Figure 18A:
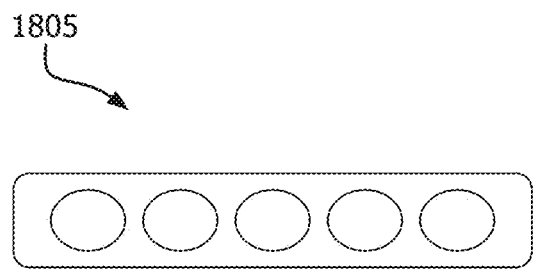
FIGS. 18A and 18B is a schematic illustration depicting the variable compliance of a resealable port or manifold in accordance with some embodiments.
Figure 18B:
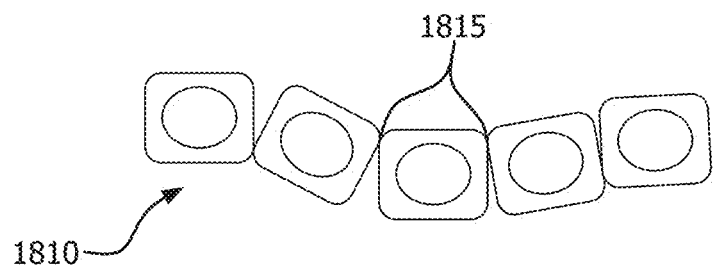

Looking at FIGS. 18A and 18B, a resealable port and/or a manifold can have a variable compliance. In some embodiments, the resealable port and/or the manifold may have a less compliant structure 1805 (shown in FIG. 18A) for an intended use of the encapsulation device that requires a more rigid structure, e.g., implantation on the surface of a metal plate or bone or within a metal plate or bone. For example, the resealable port and/or the manifold may be a singular integrated structure, as generally shown in FIG. 18A. In other embodiments, the resealable port and/or the manifold may have a more compliant structure 1810 (shown in FIG. 18B) for an intended use of the encapsulation device that requires a more flexible structure, e.g., implantation in a subcutaneous region or on a surface of an organ or within an organ. For example, the resealable port and/or the manifold may have hinge-like structures 1815 positioned between the various openings 1820. In some embodiments, the hinge-like structures 1815 may be formed of a material such as expanded PTFE or other flexible biocompatible material. Alternatively, a shaping element, as discussed in detail herein, which may include a shape memory material or structure made therefrom, may be used in the construction of the resealable port and/or the manifold to impart a more compliant structure.

Figure 19:
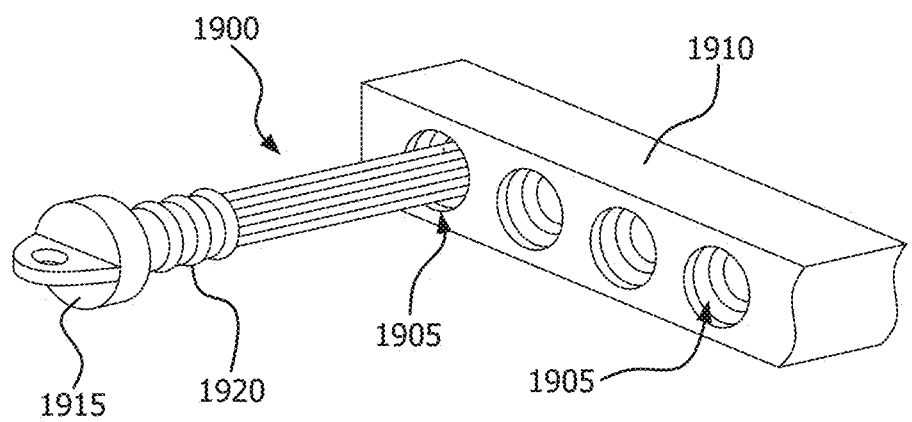
FIG. 19 is a schematic illustration of a cell containment member containing a sealing member partially positioned in an opening of a manifold in accordance with some embodiments.

In other embodiments, one or more cell containment member (or other therapeutic device) may be housed within the containment tubes. In some embodiments, a cell containment member can be designed to seal with an interface of the resealable port and/or the manifold such that the cell containment member is the sealing surface (i.e., the cell containment member is self-sealing). Turing to FIG. 19, a manifold 1910 is depicted with a cell containment member 1900 positioned partially in one of the openings 1905. The cell containment member 1900 contains a sealing member 1920 such that when the cell containment member 1900 is fully inserted into the opening 1905, it is sealed to the opening 1905 of the manifold. The cell containment member 1900 may also include a grasping structure 1915 (e.g., a tab) such that a clinician can hold the grasping structure 1915 to hold or manipulate (e.g., insert or remove) the cell containment member 1900. The cell containment member 1900 can be repeatedly sealed and unsealed via sealing member 1920 to the manifold 1910. It is to be appreciated that a similar or identical containment member 1900 may be used to seal and reseal to a resealable port. The sealing member 1920 may be attached to the manifold or resealable port such as, for example, with friction, by clamping, or with a screw comprised of threads and grooves.

V. Encapsulation Device with Central Manifold

Figure 20A:
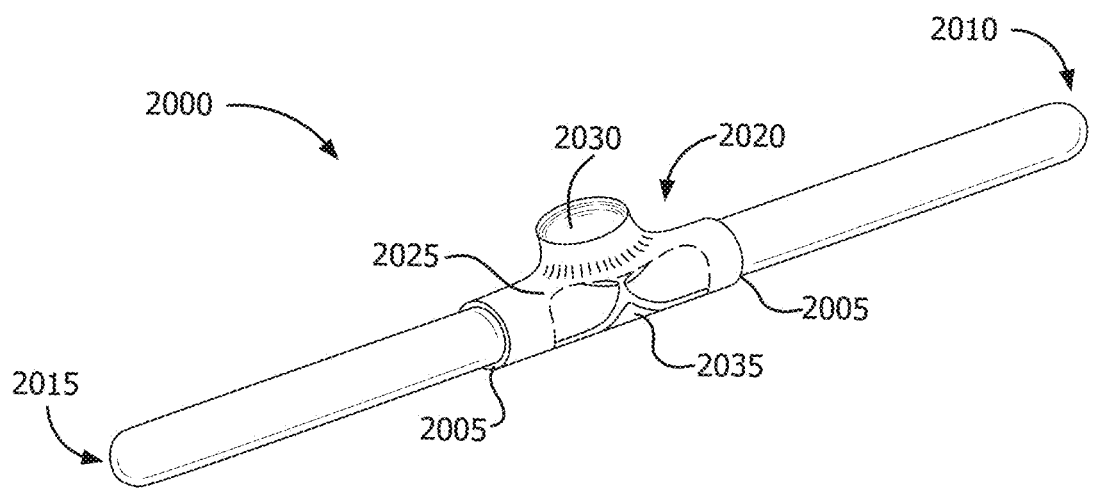
FIG. 20A shows an encapsulation device having a single containment tube with a centrally located manifold in accordance with some embodiments.

FIG. 20A shows an encapsulation device containing a single containment tube with a centrally located manifold in accordance with various embodiments of the present disclosure. It is to be appreciated that the term "centrally" as used herein is meant to include a distance surrounding the center point such that the manifold may not be perfectly centered. In other embodiments, the manifold may be positioned a distance off-center or nearer to the proximal or distal end. The encapsulation device 2000 may include a containment tube 2005, a distal end 2010, a proximal end 2015, a point 2020 between the distal end 2010 and the proximal end 2015 (e.g., center or off center by a predetermined distance), a divider element 2035, and a manifold 2025 having a single connection port 2030. The divider element 2035 enables the flow of a fluid containing cells (or other biologic moiety) to be divided such that a portion of the cells flow in a distal direction and a portion of the cells flow in a proximal direction. It is to be appreciated that a cell containment member (or other therapeutic device) may be placed inside the containment tube 2005 though the connection port 2030 in the manifold 2025.

Figure 20B:
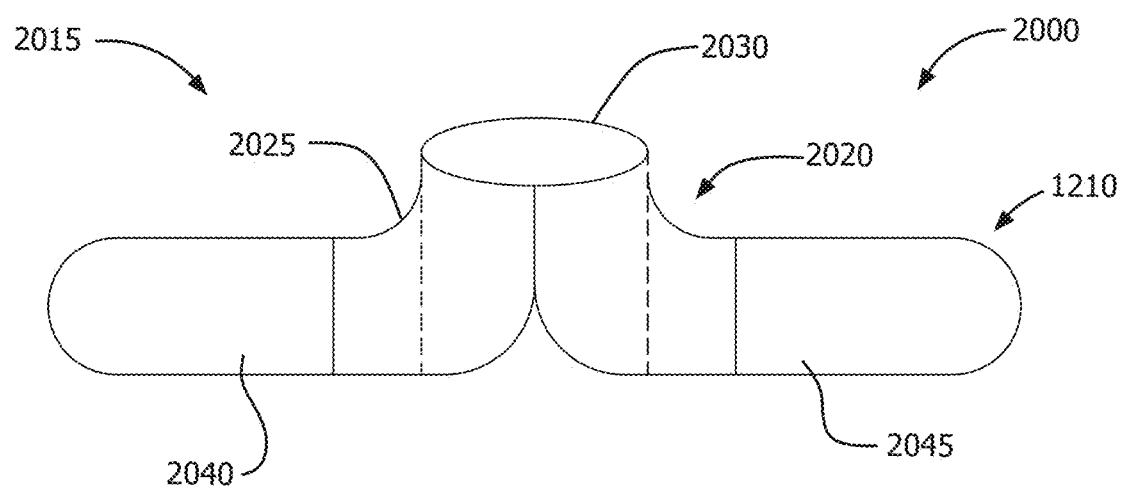
FIG. 20B is a schematic illustration of an encapsulation device having two containment tubes and a centrally located manifold in accordance with some embodiments.

FIG. 20B shows an encapsulation device containing two containment tubes with a centrally located manifold in accordance with various embodiments. The encapsulation device 2000 includes a first containment tube 2040 and a second containment tube 2045, and a manifold 2025 fluidly connecting the first and second containment tubes 2040, 2045 (e.g., at first access ports of the first and second containment tubes (not depicted)) and having a single connection port 2030. The manifold is positioned at a point 2020 between the distal end 2015 of the first containment tube 2040 and the distal end 2010 of the second containment tube 2045. It is to be appreciated that a cell containment member (or other therapeutic device) may be placed inside each of the containment tubes 2040, 2045 though the connection port 2030 in the manifold 2025.

Figure 21:
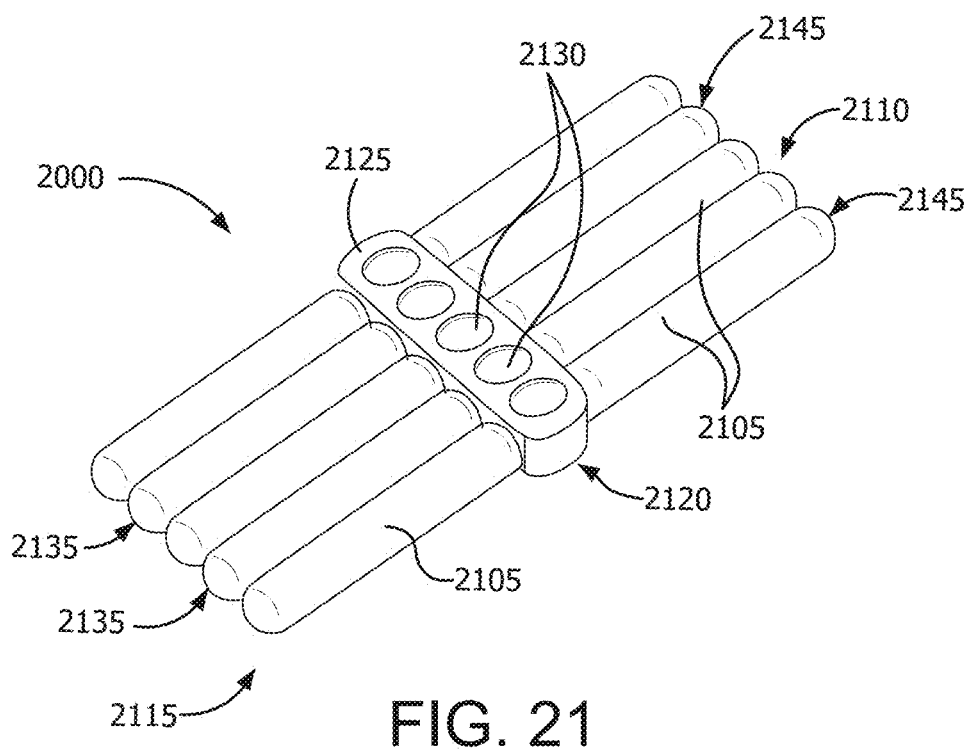
FIG. 21 is a schematic illustration of an encapsulation device having a plurality of containment tubes with a centrally located manifold.
Figure 33:
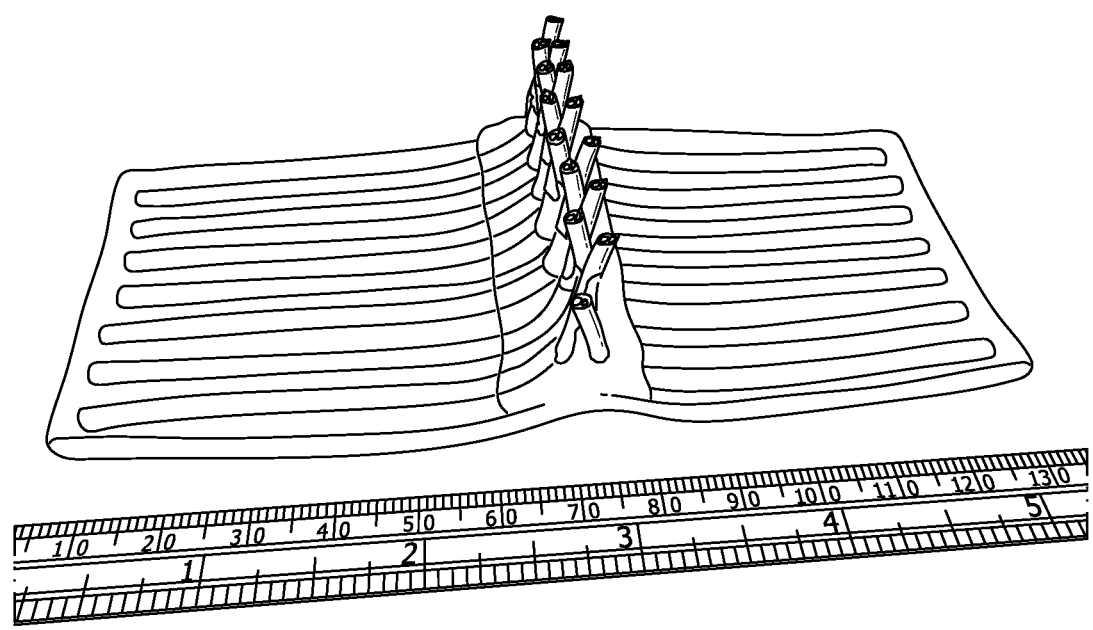
FIG. 33 is a schematic illustration depicting a cell containment device with a center manifold in accordance with some embodiments.

FIG. 21 depicts a cell encapsulation device 2100 that includes a plurality of containment tubes 2105 that have a distal end 2110 and a proximal end 2115, a point 2120 between the first access ports 2145 at the distal end 2110 and the second access ports 2135 at the proximal end 2115. The point 210 may be center or off center by a predetermined distance. In addition, the manifold 2125 has multiple connection ports 2130 that are fluidly connected to the first and second access ports 2135, 2145. In some embodiments, the manifold 2125 is centrally located between the first and second access ports 2135, 2145. as is exemplified in FIG. 33. In other embodiments, the manifold may be located off-center or more towards the proximal end 2115 or the distal and 2110, as is exemplified in FIG. 34. In some embodiments, the manifold 2125 includes divider elements (not shown) that enable the flow of a fluid containing cells (or other biologic moiety) to be divided such that a portion of the cells flow in a distal direction and a portion of the cells flow in a proximal direction. It is to be noted that cell containment members (or other therapeutic devices) may be placed inside the containment tubes 2105 though the connection ports 2130. In addition, although not depicted, the encapsulation device 2100 could be formed of a plurality of first containment tubes and second containment tubes such as is described with reference to FIG. 20B. In some embodiments, resealable ports (not shown) may be fluidly connected to the containment tubes at the proximal end 2115 and the distal end 2110. In other embodiments, resealable caps (not depicted) may be used to close off and seal the containment tubes 2105.

Figure 22:
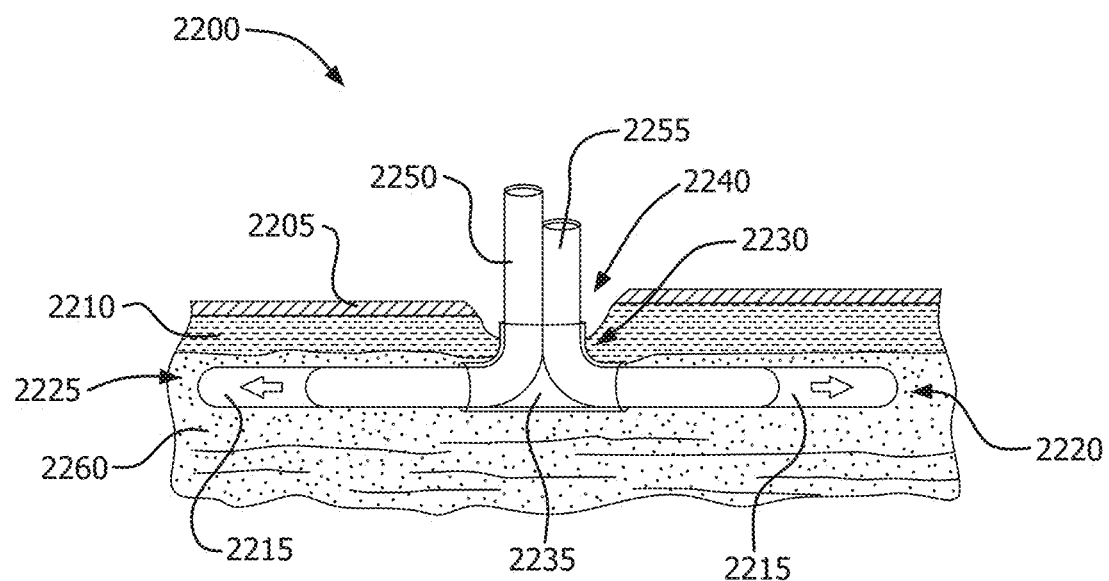
FIG. 22 is a schematic illustration depicting cell encapsulation members being inserted in an encapsulation device that has been implanted in tissue in accordance with some embodiments.

FIG. 22 depicts cell encapsulation members being inserted in an encapsulation device 2200 that has been implanted under skin 2205 and subcutaneous tissue 2210, and into tissue bed 2260 in accordance with some embodiments. The encapsulation device 2200 may include a point 2230 between the distal end 2220 and the proximal end 2225 (e.g., center or off center by a predetermined distance) of the containment tube 2215, and a manifold 2235 having an connection port 2240. In the embodiment depicted in FIG. 22, a first cell encapsulation device 2250 is being inserted into the containment tube 2215 proximally (towards the proximal end 2240 of the containment tube 2215) and a second encapsulation device 2255 is being inserted into the containment tube 2015 distally (towards the distal end 2245 of the containment tube 2015). It is to be appreciated that an encapsulation device having two containment tubes as depicted in FIG. 20B may be implanted as shown with reference to FIG. 22 and a cell containment member may be inserted into each containment tube. Advantageously, in the embodiments shown in FIGS. 20A-22, the connection port of the manifold is close to the skin while the containment tube(s) is at an appropriate depth within the tissue bed, and, as a result, the shear force required to remove the cells or cell containment member (therapeutic device) is reduced.

As discussed with respect to the encapsulation devices shown in FIGS. 11-19, the encapsulation devices depicted in FIGS. 20A-22 may further include one or more resealable ports that provides an access point through which cells or one or more cell containment member (or other therapeutic device) may be moved in and out of the luminal region of the containment tubes, one or more flush ports that provide an access point through which a fluid stream can be delivered to the luminal region of the containment tubes to flush the luminal region of the containment tubes and/or one or more cell containment member housed within the containment tubes. The cell containment member can be designed to seal with an interface of the resealable port, the manifold, and/or the access port.

VI. Bio-Absorbable Materials

FIGS. 23-30 depict various embodiments that include an amount of a bio-absorbable material distributed on one or more components of an implantable encapsulation device. The bio-absorbable material may be formed as a solid (molded, extruded, or crystals), a self-cohered web, a raised webbing, or a screen. In some embodiments, one or more layers of a bio-absorbable material(s) are attached to a non-bio-absorbable material having macroscopic porosity to allow for cell permeation to form a composite. In other embodiments, a non-bio-absorbable having microscopic porosity to decrease or prevent cell permeation is releasably attached to a porous self-cohered web to permit atraumatic removal of the containment tube from the body of a patient days following implantation. Resorbing into the body can promote favorable type 1 collagen deposition, neovascularization, and a reduction of infection. In other examples, a bio-absorbable material may be incorporated onto the cell encapsulation device as a powder. Non-limiting examples of suitable bio-absorbable materials include, but are not limited to, polyglycolide:trimethylene carbonate (PGA:TMC), polyalphahydroxy acid such as polylactic acid, polyglycolic acid poly (glycolide), and poly(lactide-co-caprolactone), poly(caprolactone), poly(carbonates), poly(dioxanone), poly (hydroxybutyrates), poly(hydroxyvalerates), poly (hydroxybutyrates-co-valerates), and copolymers and blends thereof.

Figure 23:
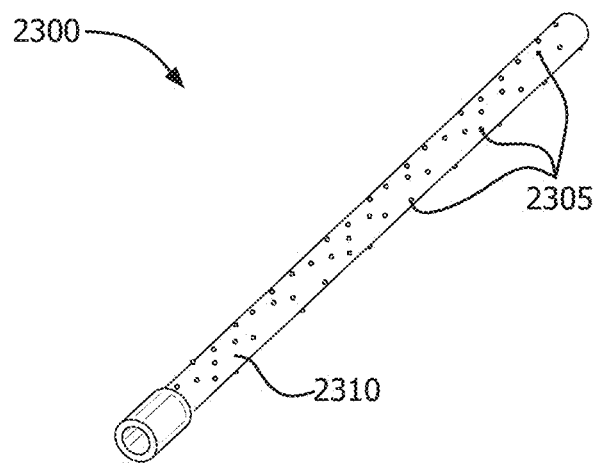
FIGS. 23-30 are schematic illustrations of encapsulation devices containing or having thereon a bio-absorbable material in accordance with some embodiments.
Figure 24:
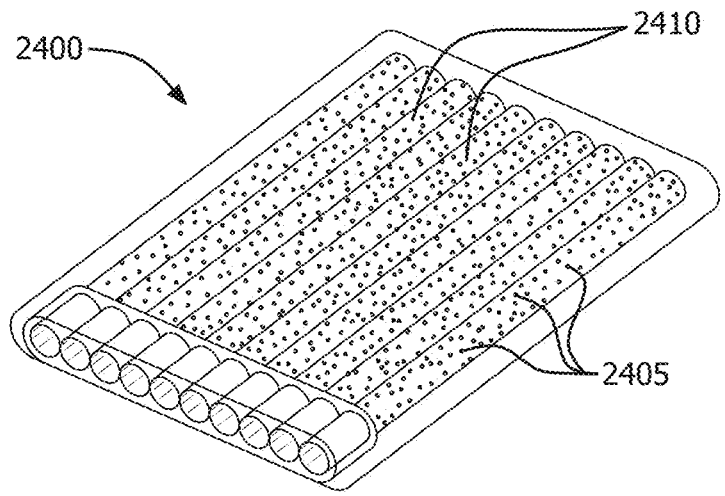
Figure 25:
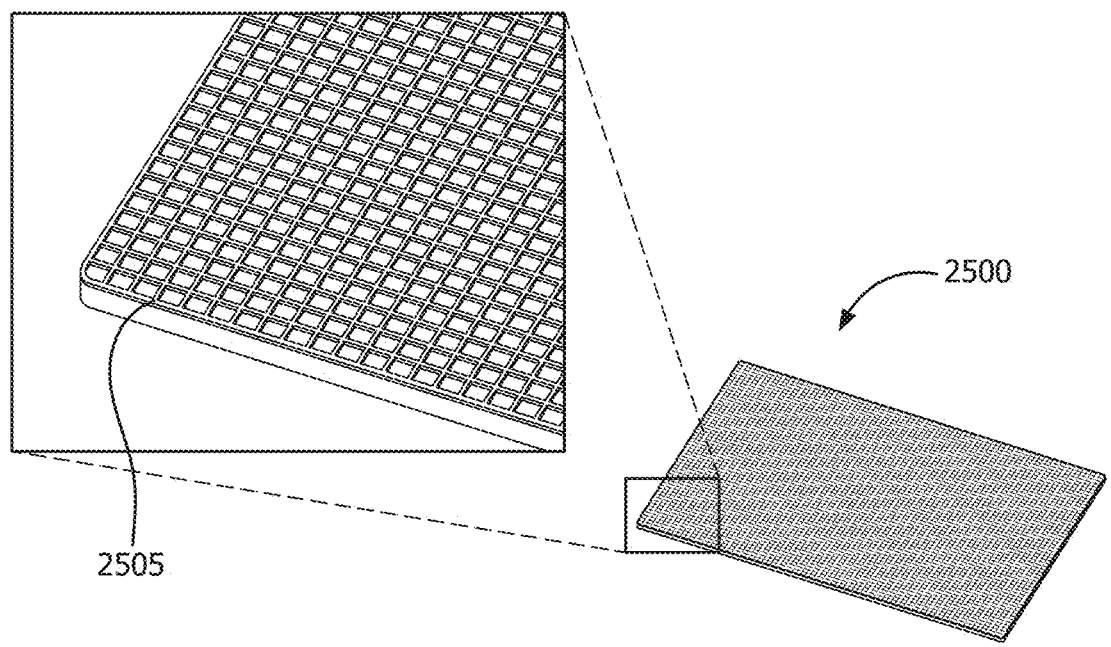

FIG. 23 shows an encapsulation device 2300 that includes an amount of a bio-absorbable material interspersed as a powder or bump like structures 2305 on a surface of a containment tube 2310. FIG. 24 depicts an encapsulation device 2400 that includes an amount of a bio-absorbable material(s) interspersed as a powder or bump like structures 2405 on the surface of the containment tubes 2410. FIG. 25 shows an amount of a bio-absorbable material(s) I on a surface of a film 2500 in a screen or raised webbing configuration 2505. The bio-absorbable material(s) can be used to support the film 2500 to minimize, or even prevent, pillowing of the film 2500 once captive cells begin to multiply and grow on the bio-absorbable material and surface of the film 2500. In some embodiments, the bio-absorbable material can be a temporary bio-absorbable material such as a polymer or metal (e.g., magnesium). The film 2500 may be used to form various components of a single containment tube and multiple containment tube encapsulation devices.

Figure 26:
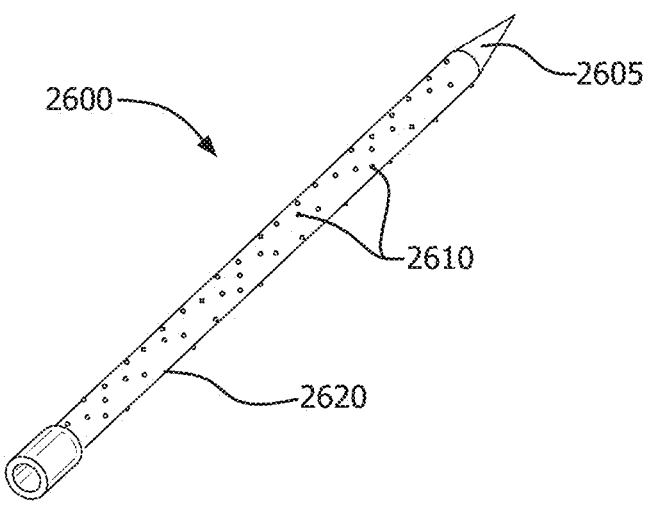
Figure 27:
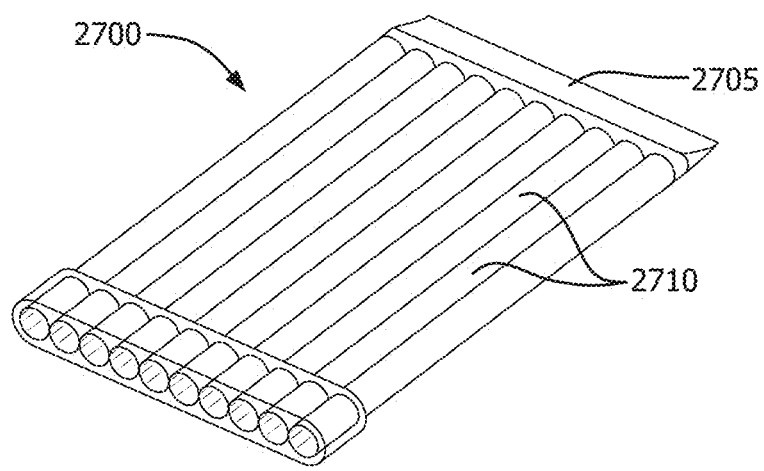
Figure 28:
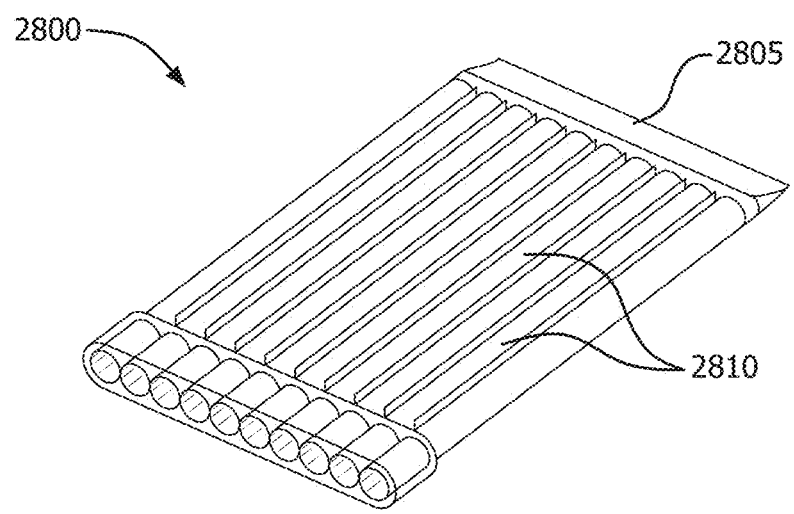

FIG. 26 shows an encapsulation device 2600 that includes an amount of a bio-absorbable material(s) interspersed as a bump-like structures 2610 and a bio-absorbable material having a tapered leading edge 2605 at an end of a containment tube 2620. FIG. 27 shows an encapsulation device 2700 that includes a bio-absorbable material as a solid structure 2705 with a tapered leading edge at an end of the containment tubes 2710. FIG. 28 depicts an encapsulation device 2800 that includes a bio-absorbable material 2805 as a solid structure having a tapered leading edge at an end of the channels 2810. The bio-absorbable material may also be interspersed as a self-cohered web structure between the containment channels 2810 to provide additional longitudinal support to the containment channels. Incorporating bio-absorbable components into an encapsulation device helps to facilitate ease of implantation. For example, the bio-absorbable material may be temperature sensitive. In particular, the bio-absorbable material is much stiffer at colder temperatures and softens at higher temperatures (e.g., body temperature once implanted) so that the bio-absorbable material becomes more conformable and compliant after implantation. As a result, the longitudinal strength, as well as tapered leading edges formed of a bio-absorbable material may allow a clinician to place the implantable apparatus in a patient with less effort and trauma to the host, and upon implantation, the bio-absorbable material becomes more conformable and compliant.

Figure 29:
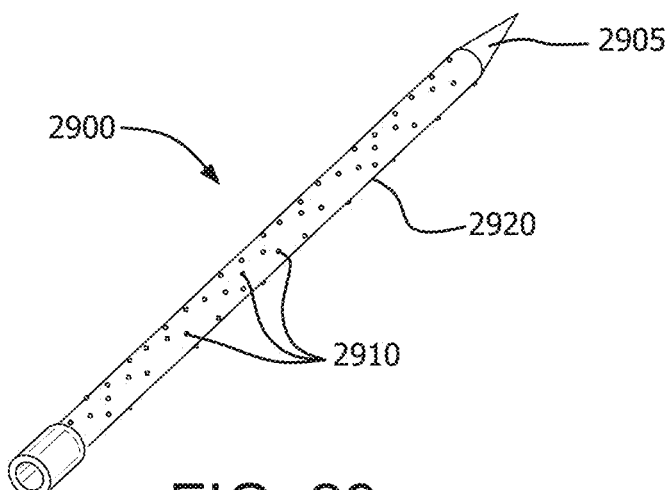
Figure 30:
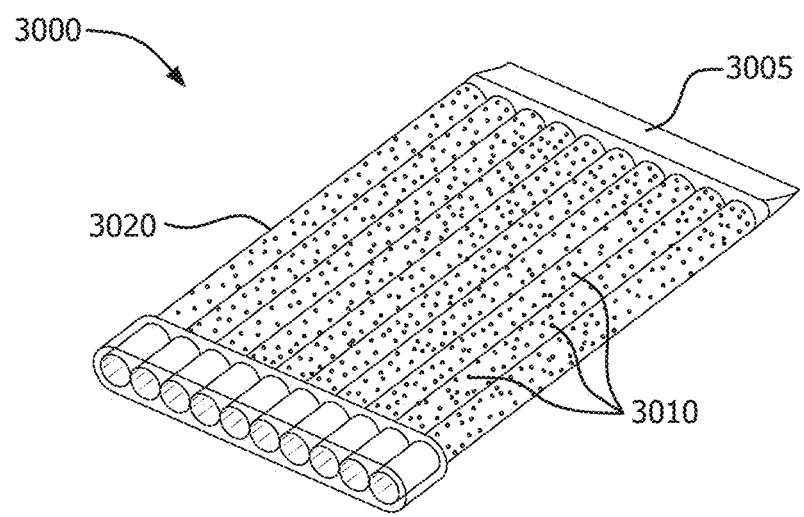

FIG. 29 shows an encapsulation device 2900 that includes a combination of a bio-absorbable material 2905 in a solid, tapered structure with a tapered leading edge as well as an amount of a bio-absorbable material distributed over the surface of the containment tube 2920 as bump like structures 2910. FIG. 30 depicts an encapsulation device 3000 that includes a combination of a bio-absorbable material 3005 in a solid, tapered structure with a tapered leading edge and as a distribution of bump like structures 3010 on a surface of the containment tubes 3020.

VII. Facilitated Nutrient Transport

Certain materials are known to have high oxygen permeability, such as, for example, perfluorocarbon emulsions, fluorohydrogels, silicone oils, silicone hydrogels, soybean oils, silicone rubbers, polyvinyl chloride, and combinations thereof. Such high oxygen permeable materials can be utilized in the material construction of the implantable apparatus, such as in one or more of the containment tubes, caps, manifolds, access ports, grasping structures, or therapeutic devices. In one embodiment, one or more of the therapeutic devices and/or cell containment tubes includes a highly oxygen permeable material. High oxygen permeable materials may be utilized in the form of a coating onto one or more of the porous polymeric membrane(s) or laminate forming the containment tube, onto one or more of the seams or seals interposed between each containment channel, or onto one or more of the containment channels with a bump structure. Alternatively, high oxygen permeable materials may be used in the form of a filling agent that may be filled partially or filled completely into the void spaces of the porous polymeric membrane or laminate forming, for example, a containment tube. In some embodiments, high oxygen permeable materials may be utilized in the form of a filling agent filled partially or completely into the lumen of the containment tube.

EXAMPLES

Example 1

A first porous expanded polytetrafluoroethylene (ePTFE) film was prepared according to the teachings of U.S. Pat. No. 3,953,566 to Gore. The film had a mass per unit area of about 2.43 g/m2, a thickness of about 8.9 µm, a density of about 0.27 g/cc, a longitudinal matrix tensile strength of about 663 MPa, a transverse matrix tensile strength of about 14.3 MPa, and an IPA bubble of about 4.83 kPA.

A second porous expanded polytetrafluoroethylene (ePTFE) film was prepared according to the teachings of U.S. Pat. No. 5,476,589 to Bacino. The film had a mass per unit area of about 1.46 g/m2, a thickness of about 0.00012 inches [~3.05 µm], a density of about 0.48 g/cc, a longitudinal matrix tensile strength of about 101,321 psi (approximately 699 MPa), a transverse matrix tensile strength of about 9288 psi (approximately 64.04 MPa), and an IPA bubble of about 35.27 psi (approximately 243.2 kPa).

A third porous expanded polytetrafluoroethylene (ePTFE) film was prepared according the teachings of U.S. Pat. No. 5,814,405 to Branca. The film had a mass per unit area of 6.23 grams/m$^2$, a thickness of 0.0017 inches (approximately 43.2 µm), an IPA bubble point of 0.41 psi (approximately 2.83 kPA), a longitudinal tensile strength of about 27974 psi (approximately 192.87 MPa), and a transverse matrix tensile strength of about 5792 psi (approximately 39.93 MPa).

A multi tube cell containing structure was manufactured by making a continuous length of the first ePTFE into a tube with an inside diameter of 0.089" (approximately 2.26 mm) generally in accordance with U.S. Pat. No. 6,617,151 to Newman, et al. (FIG. 9, steps 902 through 910 and corresponding text). The cell containment tubes were formed with one (1) longitudinal wrap of the first ePTFE membrane, six (6) overlapping helical wraps of the second ePTFE membrane, and one (1) overlapping wrap of the third ePTFE membrane. The cell containment tube was cut in to eight sections, each section having a length of approximately 7" (approximately 17.8 cm). Into one end of each tube, a 0.089" (approximately 2.26 mm) mandrel was inserted.

A compression mold to form a resealable connection member was fabricated in two halves (a top half and a bottom half), each half having a smooth cornered rectangular cavity (approximately ¼×0.164×1.7" (approximately 6.4 mm×4.2 mm×43 mm) crossed by 8 cylindrical channels having a diameter of 0.094" (approximately 2.4 mm). The connection member was constructed by forming one half of the connection member in the mold by placing a sufficient quantity of a thermoplastic polymer (THV500 from Dyneon America, Orangeburg, N.Y.) into the lower half of the compression mold and heating to a temperature sufficient to melt the thermoplastic polymer. Eight cylindrical mandrels were then pressed into the melted polymer. The mold was then cooled and the half piece was removed. This process was repeated to obtain the second half of the connection member.

The halves of the connection member were placed into each half of the compression mold and the 8 ePTFE tubes with the mandrels inserted therein were laid across the mold with the end of the ePTFE tubes located approximately halfway across the rectangular cavity. The mold was closed and placed in a hot press (Wabash model C30H-15-CPX manufactured by Wabash MPI, Wabash, Ind.). The press was set to a temperature of 400° F. (approximately 204° C.), preheated for 5 minutes, and then closed at a pressure of 0.3 tons (approximately 272 kg) for 2 minutes The mold was removed from the hot press and cooled. This process was repeated on the opposing end of the ePTFE tubes with the first manifold not heated by the hot press.

Each tube could be filled with a cell displacing core and therapeutic cells as described in U.S. Pat. No. 6,617,151 to Newman, et al. or an appropriate length cell rod such as is described in U.S. Pat. No. 5,787,900 to Butler, et al. The ends may then be closed with a suitable cap.

Example 2

An EFEP thermoplastic film (NEOFLON™ RP-4020 available from Daikin America, Orangeburg, N.Y.)) having a thickness of 1 mil (approximately 0.025 mm) was cut by a laser programed to create 8 parallel rectangular openings 0.150"×5" (approximately 3.81 mm×127 mm) with a space between openings of 0.1" (approximately 2.5 mm) (7 places of film) with an excess of thermoplastic film on each side and ends.

A multi-layer expanded PTFE (ePTFE) membrane was produced by combining layers of different membranes bonded together with a discontinuous fluoropolymer layer of fluorinated ethylene propylene (FEP). The first layer (tight layer) consists of a membrane with a smaller pore size and material properties listed in Table 3, processed based on the teachings of U.S. Pat. No. 3,953,566 to Gore. The second layer (open layer) consists of a larger pore size membrane produced based on the teachings of U.S. Pat. No. 5,814,405 to Branca, et al., where a discontinuous layer of FEP has been incorporated on the surface of this membrane based on the process teachings of International Patent Application Publication WO 94/13469 to Bacino while allowing this substrate to still be air permeable. The attributes of this open layer is listed in Table 1. The first layer (tight layer) was then put in contact with the second layer (open layer). The discontinuous FEP surface was located between the two PTFE layers as they were heated above the melting temperature of the FEP to create a bonded multilayer composite membrane with the final properties identified in Table 1. The ePTFE composite membrane was hydrophilically treated.

TABLE 1

| Layer | Mass/area (g/m²) | Non-Contact Thickness (μm) | Bubble Point Pressure (psi) [~kPA] | Airflow (L/hr@12 mbar) | MD Force to Break (lbf/in) [~N/M] | TD Force to Break (lbf/in) [~N/M] |
| --- | --- | --- | --- | --- | --- | --- |
| First Layer Membrane | 13.20 | 34.1 | 51.80 [357.1] | 12.5 | 7.02 [1229] | 11.58 [2028] |
| Second layer membrane with discontinuous FEP | 5 (1.3 from FEP) | 34.1 | 1.70 [11.7] | | 3.87 [678] | 0.48 [84.1] |
| Final Multi-layer Membrane | 17.90 | 73.4 | 52.10 [359.2] | 13.3 | 8.07 [1413] | 11.45 [2005] |

A stack consisting of a stainless steel plate 8"×8"×1/16" thick (approximately 20.3 cm×20.3 cm×1.6 mm thick), a silicone pad 6"×6" ¼" thick (approximately 15.2 cm×15.2 cm×1.6 mm thick), and the hydrophilic treated ePTFE membrane The ePTFE membrane was positioned with the 0.2 μm side facing upwards (i.e., the 7.5 μm was positioned so that it faced downwards). The precut EFEP thermoplastic film was laid on the ePTFE membrane. A second layer of an ePTFE membrane identical to the first ePTFE membrane was placed on the EFEP thermoplastic film with the 0.2 μm side facing downwards. A stainless steel sheet 6"×6"×1/16" thick (approximately 15.2 cm×15.2 cm×1.6 mm thick) was placed on top of the second ePTFE layer.

The stack was placed in a hot press (Wabash C30H-15-CPX from Wabash MPI, Wabash Ind.) that was preheated to 437° F. (approximately 225° C.) and closed to a set point pressure of 0.2 tons (approximately 181 kg) for 5 minutes. The stack was then removed from the hot press and cooled on a steel table with an aluminum weight of approximately 2 kg on top of the stack until the stack was cool to the touch.

After cooling, the thus-formed laminated sheet was removed and trimmed to have an edge seam of approximately 0.1" (approximately 0.25 cm). The ends were trimmed to be even with the end of the openings. Thermoplastic ends (THV500 available from Dyneon America, Orangeburg, N.Y.) molded as described in Example 1 were attached to the ends.

Example 3

A simulated cell rod having a diameter of 0.084" (approximately 0.21 cm) was formed as generally described in U.S. Pat. No. 6,617,151 to Newman et al. in the section entitled "Method of Making Devices", column 11, line 18 to column 12, line 29. A multi tube cell containing structure with the end sealed without loading the device with cells was inserted into a connection member (as described in Example 1). The manifold was affixed using a fibrin/thrombin surgical glue.

A syringe filled with saline was connected to a 13 gauge blunt needle. The blunt needle was compression fit into one opening in the manifold connected to the cell containment tube into which the simulated cell rod had been inserted. The plunger rod of the syringe was then lightly tapped with a mallet to create a pressure wave in the saline which served to push the simulated cell rod out of the device.

Example 4

A first porous expanded polytetrafluoroethylene (ePTFE) film was prepared according to the teachings of U.S. Pat. No. 3,953,566 to Gore. The film had a mass per unit area of about 2.43 g/m2, a thickness of about 8.9 μm, a density of about 0.27 g/cc, a longitudinal matrix tensile strength of about 663 MPa, a transverse matrix tensile strength of about 14.3 MPa, and an IPA bubble of about 4.83 kPA.

A second porous expanded polytetrafluoroethylene (ePTFE) film was prepared according to the teachings of U.S. Pat. No. 5,476,589 to Bacino. The film had a mass per unit area of about 1.46 g/m2, a thickness of about 0.00012 inches [~3.05 μm], a density of about 0.48 g/cc, a longitudinal matrix tensile strength of about 101,321 psi (approximately 699 MPa), a transverse matrix tensile strength of about 9288 psi (approximately 64.04 MPa), and an IPA bubble of about 35.27 psi (approximately 243.2 kPa).

A third porous expanded polytetrafluoroethylene (ePTFE) film was prepared according the teachings of U.S. Pat. No. 5,814,405 to Branca. The film had a mass per unit area of 6.23 grams/m$^2$, a thickness of 0.0017 inches (approximately 43.2 μm), an IPA bubble point of 0.41 psi (approximately 2.83 kPA), a longitudinal tensile strength of about 27974 psi (approximately 192.87 MPa), and a transverse matrix tensile strength of about 5792 psi (approximately 39.93 MPa).

A single tube cell containing structure was formed by making a continuous length of the first ePTFE into a tube with an inside diameter of 0.089" (approximately 2.26 cm) generally in accordance with teaching set forth in U.S. Pat. No. 6,617,151 to Newman, et al. (FIG. 9, steps 902 through 910 and corresponding text). The cell containment tube was formed with one (1) longitudinal wrap of the first ePTFE membrane, six (6) overlapping helical wraps of the second ePTFE membrane, and one (1) overlapping wrap of the third ePTFE membrane. The cell containment tube was cut to obtain a section approximately 6 cm in length.

Into one end (distal) of the shortened tube, a fluorinated ethylene propylene (FEP) plug was inserted and sealed in place by use of HOTweezers thermal wire strippers Model M10 with a handpiece 4C modified with a 2.25 mm wire hole in the jaws (Meisei Corporation, Westlake Village, Calif.) to melt the outer surface of the plug to the interior of the ePTFE cell containment tube. Into the open end of the cell containment tube a spline approximately 5 cm long fabricated out of silicone with ribbed protrusions was inserted. The spline was similar to that described in U.S. Pat. No. 5,980,889, to Butler et al. at FIG. 2, item 7.

A filling assembly was constructed by taking a Bionate 80A PCU (polycarbonate polyurethane) (available from DSM Inc) tube with a dimension of 0.89 mm inner diameter (ID) and 1.6 mm outer diameter (OD) and approximately 5 cm long and attaching an adaptor to one end. The adaptor was molded out of Bionate 80A PCU and had dimension of 1.6 mm ID and 2.25 mm OD. The adaptor was cut to a length of 3 mm. A mandrel was inserted into the PCU tube with approximately 1 mm protruding from the end. The adaptor was then placed over the Bionate 80A PCU tube so the ends of the Bionate 80A PCU tube and adaptor were flush. The adaptor and Bionate 80A PCU tube subassembly was inserted into the ePTFE cell containment tube so that the mandrel just touched the internal spline. The adaptor, Bionate 80A PCU tube, and ePTFE cell containment tube were sealed together by the use of HOTweezers thermal wire strippers Model M10 with a handpiece 4C modified with a 2.25 mm wire hole in the jaws (Meisei Corporation, Westlake Village, Calif.) with a cylindrical opening measuring approximately 2.25 mm in diameter.

The entire assembly was leak checked by submersing in isopropyl alcohol (IPA) and pressurizing the internals of the assembly plugs with air to 5 psig (approximately 0.34 bar). No bubbles were observed escaping from the device.

Example 5

A tube assembly was created by generally following the procedure described in U.S. Pat. No. 5,565,166 to Witzko. The size of the tube was 3 mm in diameter and the space between tubes was 1 mm. The starting membrane had a mass per unit area of 42.4 grams/square meter and a thickness of 0.07 mm. The tube assembly was trimmed so as to be 8 tubes wide and 16.5 cm long.

A compression mold to form a resealable connection member was fabricated in two halves (a top half and a bottom half), each half having a smooth cornered rectangular cavity (approximately ¼×0.164×1.7" (approximately 6.4 mm×4.2 mm×43 mm) crossed by 8 cylindrical channels having a diameter of 3 mm). The connection member was constructed by forming one half of the connection member in the mold by placing a sufficient quantity of a thermoplastic polymer (THV500 from Dyneon America, Orangeburg, N.Y.) into the lower half of the compression mold and heating to a temperature sufficient to melt the thermoplastic polymer. Eight cylindrical mandrels were then pressed into the melted polymer. The mold was then cooled and the half piece was removed. This process was repeated to obtain the second half of the connection member.

The half pieces were placed into each half of the mold and 8 ePTFE tubes with 1.0 mm mandrels inserted into the end of each tube were laid across the mold with the end of the ePTFE tube approximately halfway across the rectangular cavity. The top half of the mold was assembled and the mold placed in a hot press above the melt temperature of the thermoplastic polymer. The mold was held in the hot press for a sufficient time to melt the thermoplastic polymer then fully closed. The mold was removed from the hot press and cooled. This was repeated on the opposing end of the ePTFE tubes with the first manifold not heated by the hot press.

The thermoplastic polymer used for this example was THV500 from Dyneon (Dyneon America, Orangeburg, N.Y.) and the press was set to a temperature of 400° F. (approximately 204° C.), preheated for 5 minutes, and then closed at 0.3 tons (approximately 272.2 kg) for 2 minutes.

Each tube could be filled with a cell displacing core and therapeutic cells as described in U.S. Pat. No. 6,617,151 to Newman or an appropriate length cell rod as described in U.S. Pat. No. 5,787,900 to Butler, et al. The ends would then be closed with a suitable cap. Each tube could also be filled with cells without a cell displacing core. The diameter of each tube may be 0.5 mm or less, 0.25 mm or less, or 0.13 mm or less.

Example 6

Three layers of an open (porous) microstructure ePTFE membrane as taught in U.S. Pat. No. 5,814,405 to Branca, et al. was wrapped on a 40 mm OD SST mandrel. The membrane has a discontinuous coating of fluorinated ethylene propylene(FEP) thermoplastic on one surface which was used as an adhesive in the construct. The discontinuous FEP coating maintained porosity while also providing a method of adhering the ePTFE layers together. The discontinuous FEP coating was applied according to the methods taught in U.S. Pat. No. 6,159,565, to Campbell et al. The ePTFE layers were wrapped onto the mandrel in a "cigarette roll" fashion with the FEP side away from the mandrel to prevent the ePTFE membrane from adhering to the mandrel.

Next, 2 layers of a tight microstructure ePTFE membrane as taught in U.S. Pat. No. 5,476,589 to Bacino were wrapped onto the ePTFE construct. This ePTFE membrane was also provided with a discontinuous coating of FEP as described previously The FEP was also positioned away from the mandrel.

The mandrel and ePTFE construct were then placed in a convection air furnace (Grieve, Model NT-1000 available from The Grieve Corporation, Round Lake, Ill.) at a temperature above the melt temperature of the FEP (320° C.). After a 10 minute dwell at 320° C., the mandrel and ePTFE construct were removed and allowed to air-cool to ambient temperature. Once cool, the construct was slit longitudinally and removed from the mandrel.

The ePTFE construct at this point was a planar multi-layer laminate of ePTFE with a very open microstructure with no FEP on one side and a very tight microstructure ePTFE with discontinuous FEP on the opposing side. Next, the construct was folded in half so that the tight microstructure side was positioned against itself.

Using a template manufactured from aluminum sheet, localized heat was applied through the use of a Weller soldering iron Model PU-120T, available from McMaster Carr. The localized heat re-melted the FEP, causing local adherence of the construct. The adhered pattern resulted in a planar construct with 7 channels of un-adhered material and a channel at one end that allowed all of the channels to communicate.

The flat pattern of the template was designed to form flat channels having a length that approximated the circumference of a 4 mm diameter. After trimming excess material with scissors, a quantity of 7, 4 mm outside diameter plastic tubings were placed into the un-adhered channels. The construct was then placed in a rudimentary aluminum mold, shown in FIG. 33.

Figure 34:
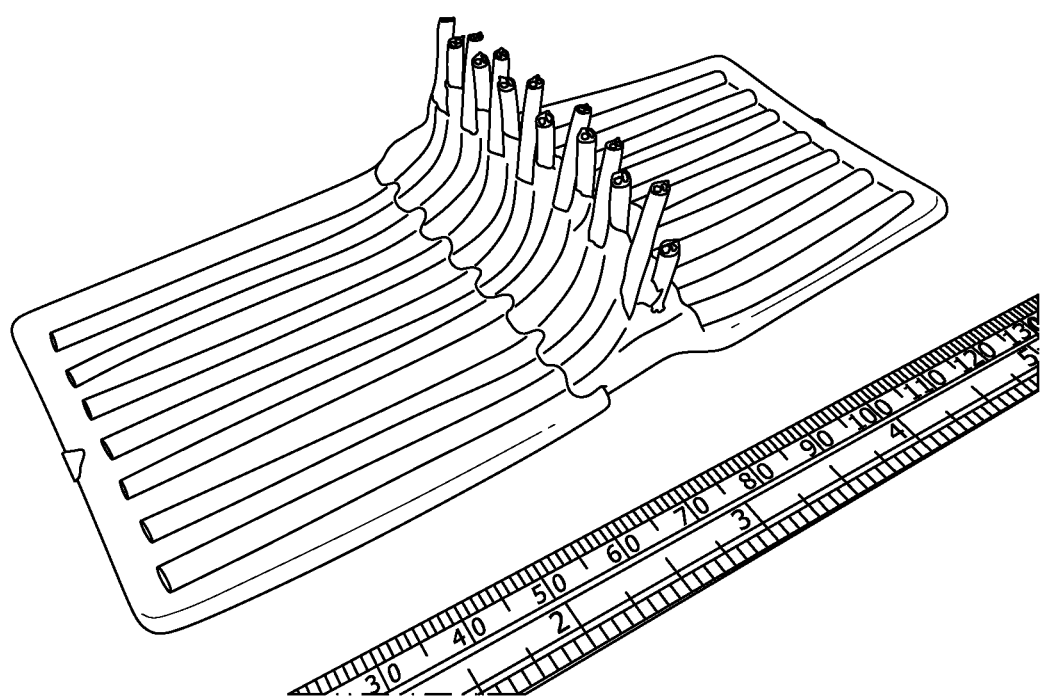
FIG. 34 is a schematic illustration depicting a cell containment device with an off-center manifold in accordance with some embodiments.

The mold was clamped in the closed position and silicone, part number NuSil MED-1137, available from NuSil Corporation, Cupertibo, Calif., was forced into the mold using a 20 CC syringe. The mold and indwelling construct were placed in an air convection oven (Yamatomo, Mod& DKN600, available from Yamatomo Scientific, Tokyo, Japan) at 60° C. After a dwell time of approximately 12 hours, the mold and construct were allowed to air cool to ambient temperature. Upon cooling, the mold was opened and the part was removed. The silicone required slight trimming of the flash. This process resulted in a construct measuring approximately 54 mm×85 mm of laminated ePTFE with an open (porous) microstructure exterior layer which will promote vascular ingrowth, 7 channels running from a silicone manifold at one end to a communication channel at the opposing end. A silicone bead around the periphery added sufficient stiffness for handling purposes. The interior surface of the channels was of a very tight microstructure to contain cells yet allow transport of nutrients and other biomolecules. This construct, as shown in FIG. 34, could be used to house cell rods, or if sized appropriately, used to house cells alone.

Example 7

Three layers of a very open (porous) microstructure ePTFE membrane as taught in U.S. Pat. No. 5,814,405 to Branca, et al. was wrapped on a 40 mm OD SST mandrel. The ePTFE membrane had a discontinuous coating of fluorinated ethylene propylene (FEP) thermoplastic on one surface which was used as an adhesive in forming the construct. The discontinuous coating maintained porosity while also providing a method of adhering the ePTFE layers together. The discontinuous FEP coating was applied according to U.S. Pat. No. 6,159,565, to Campbell et al. The ePTFE layers were wrapped onto the mandrel in a "cigarette roll" fashion with the FEP side positioned away from the mandrel to prevent the ePTFE membranes from adhering to the mandrel.

Next, 2 layers of a tight microstructure membrane as taught in U.S. Pat. No. 5,476,589 to Bacino were wrapped onto the ePTFE construct. This ePTFE membrane was also provided with a discontinuous coating of FEP as described previously. The FEP was also positioned away from the mandrel.

The mandrel and ePTFE construct were then placed in a convection air furnace (Grieve, Model NT-1000 available from The Grieve Corporation, Round Lake, Ill.) at a temperature above the melt temperature of the FEP (320° C.). After a 10 minute dwell at 320° C., the mandrel and ePTFE construct were removed and allowed to air-cool to ambient temperature. Once cool, the construct was slit longitudinally and removed from the mandrel.

The ePTFE construct at this point was a planar multi-layer laminate of ePTFE with a very open microstructure with no FEP on one side and a very tight microstructure ePTFE with discontinuous FEP on the opposing side. Next, the construct was folded in half so that the tight microstructure side was positioned against itself.

The layered construct was then placed on a vacuum plate and covered with a piece of Zinc Selenide (available from Thor Labs, Newton, N.J.) in a 25 Watt CO2 laser. As vacuum was applied, the Zinc Selenide "laser window" applied pressure to the ePTFE laminate. Zinc Selenide allowed the CO2 laser beam to pass without coupling to its energy. The laser beam was reduced in power and defocused purposely so that it created heat, but not cut the ePTFE/FEP laminate. By altering the power and speed settings and altering the focal point, the beam was used to create focal heating of the ePTFE/FEP laminate, thereby melting and re-flowing the FEP layer and causing adhesion. Heating of the chamber containing the laminates allowed further reduction of the laser power since the laser beam only needed to raise the local temperature enough to flow the FEP (approximately 285° C.). For instance, if the chamber was operating at 250° C., the laser only needs to raise the local temperature at the point of adherence by 35° C. to facilitate adhesion.

The adhered pattern resulted in a planar construct similar to the ribbon-tube example, with 7 channels of un-adhered material and a channel at one end that allowed all channels to communicate. This assembly could then be over-molded with silicone as in the previous example if desired. Additionally, this "laser heating" method of assembly can be especially advantageous since hard tooling is not necessary and device pattern alterations can be made by programming.

Example 8

Three layers of an open (porous) microstructure ePTFE membrane as taught in U.S. Pat. No. 5,814,405 to Branca, et al. was wrapped on a 40 mm OD SST mandrel. The membrane has a discontinuous coating of fluorinated ethylene propylene(FEP) thermoplastic on one surface which was used as an adhesive in the construct. The discontinuous FEP coating maintained porosity while also providing a method of adhering the ePTFE layers together. The discontinuous FEP coating was applied according to the methods taught in U.S. Pat. No. 6,159,565, to Campbell et al. The ePTFE layers were wrapped onto the mandrel in a "cigarette roll" fashion with the FEP side away from the mandrel to prevent the ePTFE membrane from adhering to the mandrel.

Next, 2 layers of a tight microstructure membrane as taught in U.S. Pat. No. 5,476,589 to Bacino were wrapped onto the ePTFE construct. This ePTFE membrane was also provided with a discontinuous coating of FEP as described previously. The FEP was also positioned away from the mandrel.

The mandrel and ePTFE construct were then placed in a convection air furnace (Grieve, Model NT-1000 available from The Grieve Corporation, Round Lake, Ill.) at a temperature above the melt temperature of the FEP (320° C.). After a 10 minute dwell at 320° C., the mandrel and ePTFE construct were removed and allowed to air-cool to ambient temperature. Once cool, the construct was slit longitudinally and removed from the mandrel.

The ePTFE construct at this point is a planar multi-layer laminate of ePTFE with a very open microstructure with no FEP on one side and a very tight microstructure ePTFE with discontinuous FEP on the opposing side. Next, the construct was folded in half so that the tight microstructure side was positioned against itself.

Figure 35:
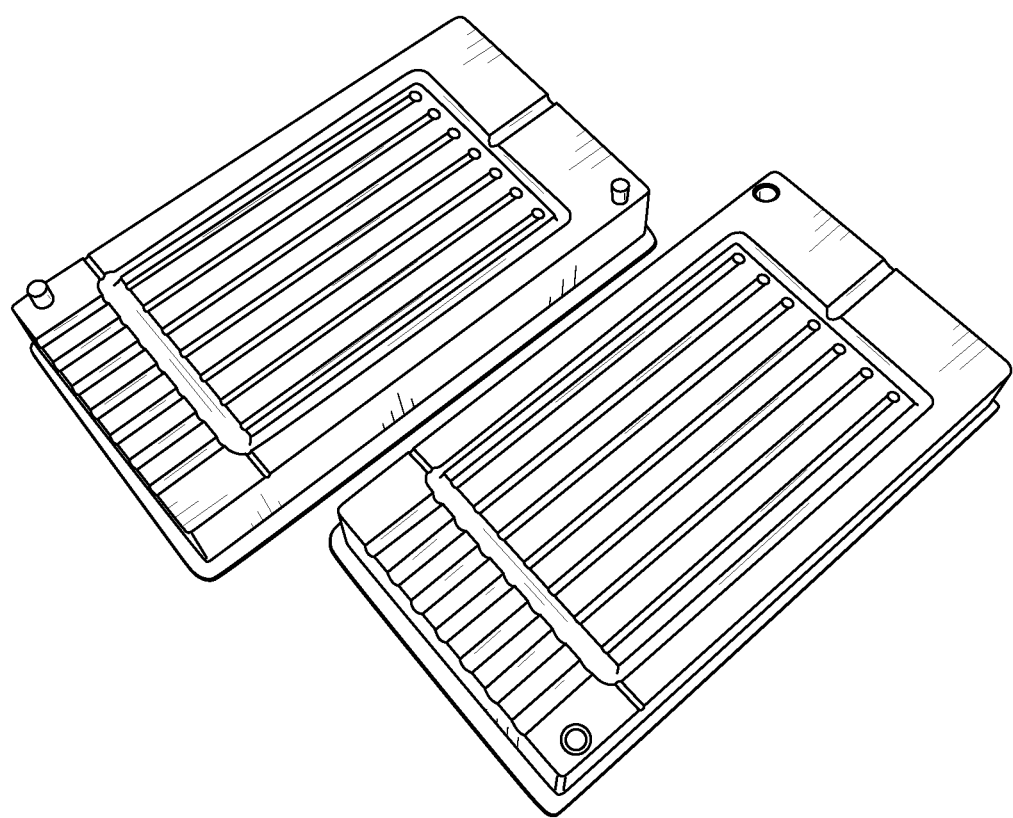
FIG. 35 is a schematic illustration depicting an aluminum mold utilized in Examples 6 and 9 in accordance with some embodiments.
Figure 36:
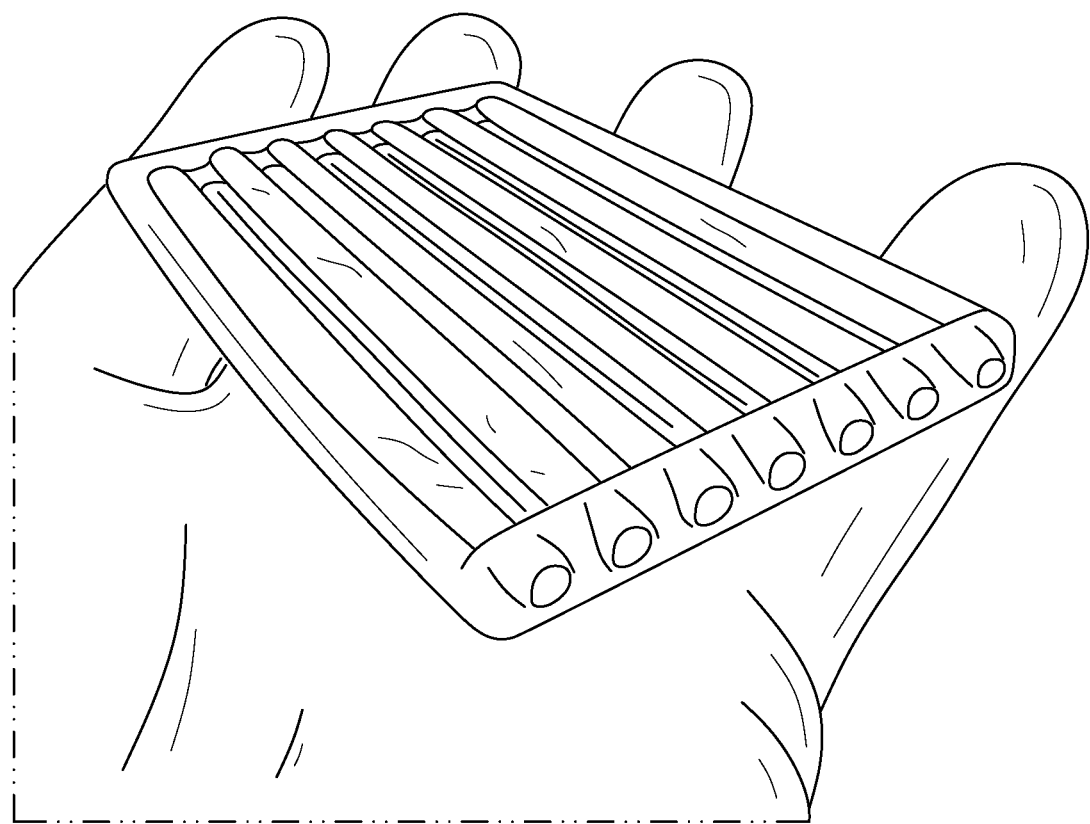
FIG. 36 is a schematic illustration depicting the cell encapsulation device formed by the method described in Example 6 in accordance with some embodiments.
Figure 37:
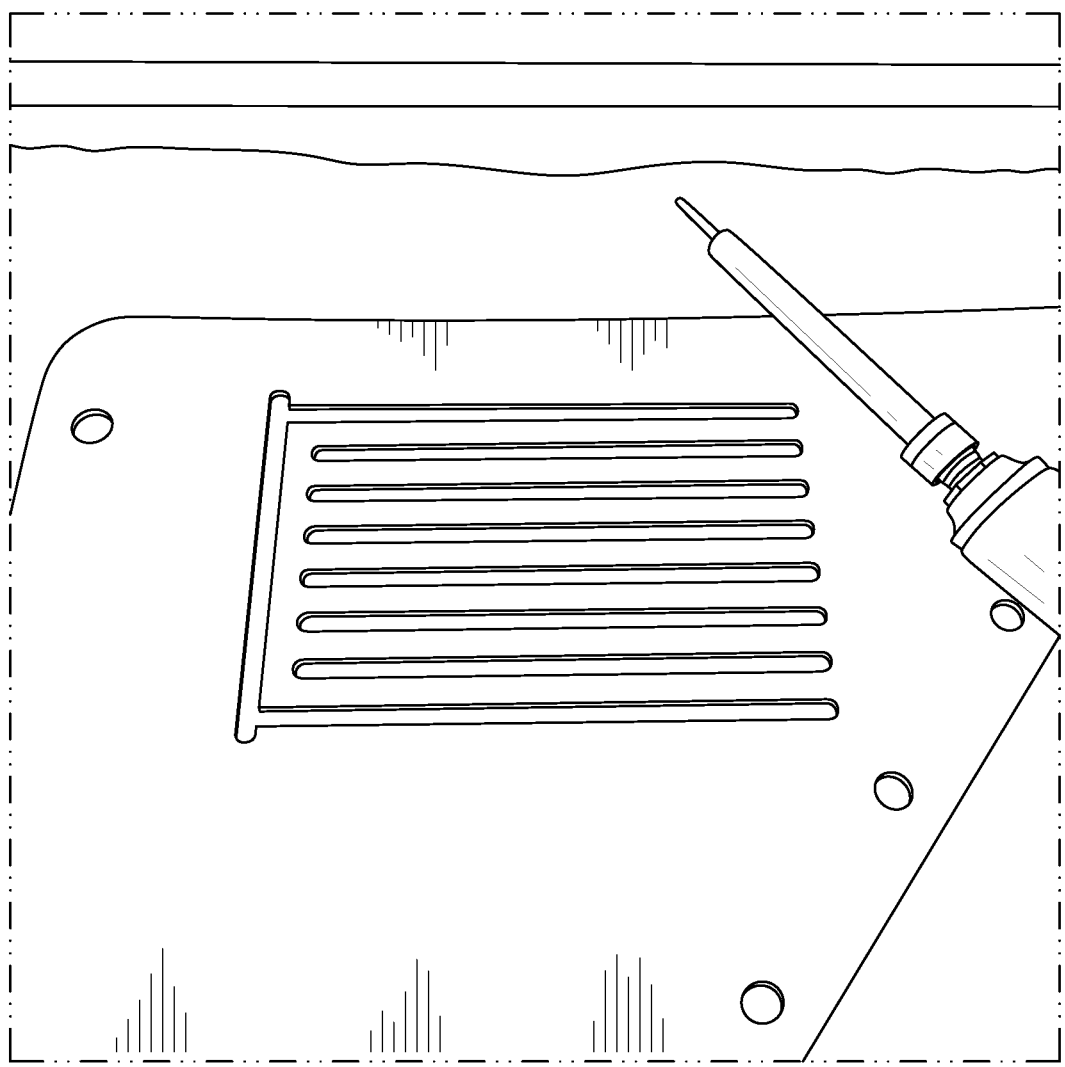
FIG. 37 is a schematic illustration of an aluminum template utilized in Examples 8, 9, and 10 in accordance with some embodiments.

Using a template manufactured from aluminum sheet and shown in FIG. 35, localized heat was applied through the use of a Weller soldering iron Model PU-120T available from McMaster Carr. The localized heat re-melted the FEP, causing local adherence of the construct. The adhered pattern resulted in a planar construct with 7 channels of un-adhered material and a channel at one end that allowed all channels to communicate. The flat pattern of the template was designed to form flat channels having a length that approximated the circumference of a 4 mm diameter. The excess material was trimmed away and one of the channels was partially separated and designated as the flush port.

The construct may then be over-molded and/or have manifolds installed as in Example 6 as appropriate. This description will yield a cell containment device with multiple channels and a flush port which will facilitate removal of cell rods from within.

Example 9

Three layers of an open (porous) microstructure ePTFE membrane as taught in U.S. Pat. No. 5,814,405 to Branca, et al. was wrapped on a 40 mm OD SST mandrel. The membrane has a discontinuous coating of fluorinated ethylene propylene(FEP) thermoplastic on one surface which was used as an adhesive in the construct. The discontinuous FEP coating maintained porosity while also providing a method of adhering the ePTFE layers together. The discontinuous FEP coating was applied according to the methods taught in U.S. Pat. No. 6,159,565, to Campbell et al. The ePTFE layers were wrapped onto the mandrel in a "cigarette roll" fashion with the FEP side away from the mandrel to prevent the ePTFE membrane from adhering to the mandrel.

Next, 2 layers of a tight microstructure membrane as taught in U.S. Pat. No. 5,476,589 to Bacino were wrapped onto the ePTFE construct. This ePTFE membrane was also provided with a discontinuous coating of FEP as described previously. The FEP was also positioned away from the mandrel.

The mandrel and ePTFE construct were then placed in a convection air furnace (Grieve, Model NT-1000 available from The Grieve Corporation, Round Lake, Ill.) at a temperature above the melt temperature of the FEP (320° C.). After a 10 minute dwell at 320° C., the mandrel and ePTFE construct were removed and allowed to air-cool to ambient temperature. Once cool, the construct was slit longitudinally and removed from the mandrel.

The ePTFE construct at this point is a planar multi-layer laminate, of ePTFE with a very open microstructure with no FEP on one side and a very tight microstructure ePTFE with discontinuous FEP on the opposing side. Next, the construct was folded in half so that the tight microstructure side was positioned against itself.

Using a template manufactured from aluminum sheet and shown in FIG. 35, localized heat was applied through the use of a Weller soldering iron Model PU-120T available from McMaster Carr. The localized heat re-melted the FEP, causing local adherence of the construct. The adhered pattern resulted in a planar construct with 7 channels of un-adhered material and a channel at one end that allowed all channels to communicate. The flat pattern of the template was designed to form flat channels having a length that approximated the circumference of a 4 mm diameter. After trimming excess material with scissors, a quantity of 7, 4 mm outside diameter plastic tubings were placed into the un-adhered channels. The construct was then placed in a rudimentary aluminum mold shown in FIG. 33.

The mold was clamped in the closed position and preheated to approximately 200° C.). After preheating, a molten blend of polyglycolic acid and trimethylene carbonate (PGA:TMC) as taught in U.S. Pat. No. 6,165,217 to Hayes, was injected into the mold. Once the mold channels were full, the mold was quenched in room temperature water to facilitate rapid cooling. Upon cooling, the mold was separated and the part was removed. The resultant device resembles that from Example 6 except that the molded stiffener bead around the periphery was made of a bio-absorbable polymer. The bead may be shaped in order to provide rigidity and even may be tapered or pointed to facilitate insertion into a patient.

Although PGA:TMC is described, other bio-absorbable polymers may be utilized. Choices may be affected by desired needs (such as stiffness) and/or degradation profiles. Since many of bio-absorbable polymers are melt processable, manufacturing processes may include extrusion, injection molding and additive manufacturing techniques (such as, for example, 3-D printing).

The biodegradable portion of this device may also include metals (such as magnesium). In this case, the metals may be machined or formed as separate components and adhered in the final assemble through the use of adhesives (such as previously mentioned FEP).

Example 10

Three layers of an open (porous) microstructure ePTFE membrane as taught in U.S. Pat. No. 5,814,405 to Branca, et al. was wrapped on a 40 mm OD SST mandrel. The membrane has a discontinuous coating of fluorinated ethylene propylene(FEP) thermoplastic on one surface which was used as an adhesive in the construct. The discontinuous FEP coating maintained porosity while also providing a method of adhering the ePTFE layers together. The discontinuous FEP coating was applied according to the methods taught in U.S. Pat. No. 6,159,565, to Campbell et al. The ePTFE layers were wrapped onto the mandrel in a "cigarette roll" fashion with the FEP side away from the mandrel to prevent the ePTFE membrane from adhering to the mandrel.

Next, 2 layers of a tight microstructure membrane as taught in U.S. Pat. No. 5,476,589 to Bacino were wrapped onto the ePTFE construct. This ePTFE membrane was also provided with a discontinuous coating of FEP as described previously. The FEP was also positioned away from the mandrel.

The mandrel and ePTFE construct were then placed in a convection air furnace (Grieve, Model NT-1000 available from The Grieve Corporation, Round Lake, Ill.) at a temperature above the melt temperature of the FEP (320° C.). After a 10 minute dwell at 320° C., the mandrel and ePTFE construct were removed and allowed to air-cool to ambient temperature. Once cool, the construct was slit longitudinally and removed from the mandrel.

The ePTFE construct at this point is a planar multi-layer laminate, of ePTFE with a very open microstructure with no FEP on one side and a very tight microstructure ePTFE with discontinuous FEP on the opposing side. Next, the construct was folded in half so that the tight microstructure side was positioned against itself.

Using a template manufactured from aluminum sheet and shown in FIG. 35, localized heat was applied through the use of a Weller soldering iron Model PU-120T available from McMaster Carr. The localized heat re-melted the FEP, causing local adherence of the construct. The adhered pattern resulted in a planar construct with 7 channels of un-adhered material and a channel at one end that allowed all channels to communicate. The flat pattern of the template was designed to form flat channels having a length that approximated the circumference of a 4 mm diameter. After trimming excess material with scissors, a quantity of 7, 4 mm outside diameter silicone beads were inserted into the un-adhered channels.

This procedure was repeated so as to acquire 2 identical ePTFE constructs. Each ePTFE construct had a silicone bead filling each channel. Next, each ePTFE construct was placed in an aluminum mold that oriented the construct in a configuration in which the majority of the construct is planar and the open ends of the channels were bent at an approximately 90 degrees up, out of plane orientation. The other construct placed in the mold was a mirror image to the first. Each device was configured "back-to-back", with all channel open-ends held in close proximity and in a bent up, out of plane orientation.

The mold was clamped in the closed position and silicone, part number NuSil MED-1137, available from NuSil Corporation, Cupertibo, Calif., was forced into the mold using a 20 CC syringe. The mold and indwelling construct were placed in an air convection oven (Yamatomo, Model DKN600 available from Yamatomo Scientific, Tokyo, Japan) at 60° C. After a dwell time of approximately 12 hours, the mold and construct were allowed to air cool to ambient temperature. Upon cooling, the mold was opened and the part was removed from the mold. The silicone beading (qty=14) were removed from the channels.

This process resulted in a construct measuring approximately 54 mm×120 mm of laminated ePTFE with an open (porous) microstructure exterior layer which will promote vascular ingrowth with 14 channels running from a silicone manifold at the center to 2 communication channels (one at each end). A silicone bead placed around the periphery added sufficient stiffness for handling purposes. The interior surface of the channels were of a tight microstructure to contain cells yet avow transport of nutrients and other biomolecules. This construct could be used to house cell rods, or if sized appropriately, used to house cells alone.

This center manifold configuration allows the ports to be accessed approximately perpendicular to the surface of the patient's skin, thereby reducing trauma caused during replacement of cell rods. Also, by inserting the cell rods from the center of the device, the shear forces required to remove them will be reduce by approximately one half.

The invention may also be described by the following:

1. An implantable encapsulation device comprising:
   a plurality of containment tubes interconnected by connection members, each said containment tube having a first access port at a first end thereof and a second access port at a second end thereof,
   wherein said containment tubes are substantially parallel to each other along a length of said device.

2. The device of claim 1,
   wherein said connection members are periodically spaced along a length of said containment tubes a distance from each other; or
   further comprising resealable caps affixed to said second access ports to seal said second end of said containment tubes; or
   wherein said containment tubes comprise a permeable membrane including an inner cell retentive layer and an outer vascularizing layer; or
   wherein said containment tubes have thereon a bioabsorbable material; or
   wherein said containment tubes are stacked upon one another in a z-direction; or
   wherein each of the plurality of containment tubes maintains a consistent cylindrical cross-section; or
   wherein said containment tubes comprise a shape memory material.

3. The device of claim 1, further comprising a removable manifold fluidly connected to said containment tubes at said first end.

4. The device of claim 3, further comprising a flush port and a tube fluidly connected to said removable manifold.

5. The device of claim 1, wherein said containment tube comprises a lumen for the reception and containment of a biological moiety or therapeutic device therein.

6. The device of claim 5, wherein the therapeutic device comprises a drug delivery device, a gene therapy device, a cell encapsulation device and combinations thereof.

7. The device of claim 6, wherein the one or more therapeutic devices are removably sealed to a manifold fluidly connected to said containment tubes at said first end.

8. The device of claim 7, wherein each of the one or more therapeutic devices includes a grasping structure.

9. The device of claim 6, wherein said biological moiety is a plurality of cells.

10. The device of claim 1, further comprising a bioabsorbable material in at least one of a solid form and a self-cohered web.

11. The device of claim 10, wherein the bio-absorbable material is formed at the first end or the second end as the solid form with a tapered leading edge.

12. A cell encapsulation device comprising:
a plurality of containment tubes, each said containment tube having a first access port at a first end thereof and a second access port at a second end thereof;
at least one port sealably connected to said containment tubes at said first end, said second end, or said first and second ends;
a manifold having one or more openings therein and being fluidly connected to said containment tubes; and
a flush port fluidly connected to said manifold by a tube.

13. The device of claim 12,
further comprising a sealable cap affixed to said flush port; or
wherein said manifold fluidly is connected to said containment tubes at said first end or at said second end; or
wherein said manifold is located at a point located between said end and said second end, and
wherein said port is sealably connected to said containment tubes at said first and second ends; or
wherein said manifold is centrally located between said first end and said second end; or
wherein said manifold comprises hinged structures positioned between said openings; or
wherein each said containment tube is affixed to one said one of more openings in said manifold; or
wherein said flush port and said tube lie in a same plane as said containment tubes; or
wherein said cell containment tubes comprise a permeable membrane including a cell retentive layer and a vascularizing layer; or
wherein each of the plurality of containment tubes maintains a consistent cylindrical cross-section; or
wherein said containment tubes comprise a shape memory material.

14. The device of claim 12, wherein said containment tube comprises a lumen for the reception and containment of a biological moiety or therapeutic device therein.

15. The device of claim 14, wherein the therapeutic device comprises a drug delivery device, a gene therapy device, a cell encapsulation device and combinations thereof.

16. The device of claim 14, wherein said biological moiety is a plurality of cells.

17. The device of claim 15, wherein the therapeutic device is removably sealed to a manifold fluidly connected to said containment tubes at said first end.

18. The device of claim 17, wherein the therapeutic device includes a grasping structure.

19. The device of claim 15, wherein said biological moiety is a plurality of cells.

20. The device of claim 12, wherein said containment tubes have thereon a bio-absorbable material.

21. The device of claim 20,
wherein said bio-absorbable material is in at least one of a solid form and a self-cohered web; or
wherein the bio-absorbable material is formed at the first end or the second end of the apparatus as the solid form with a tapered leading edge.

22. An implantable encapsulation device comprising:
a laminate sheet; and
a plurality of containment channels formed by adhered layers of the laminate sheet with seams interposed between each containment channel,
wherein the plurality of containment channels are periodically connected to each other via the seams along a length of the plurality of containment channels.

23. The device of claim 22,
wherein the plurality of containment channels are stacked upon one another in a z-direction; or
further comprising one or more therapeutic device housed within the plurality of containment channels; or
wherein the therapeutic device comprises a drug delivery device, a gene therapy device, a cell encapsulation device, and combinations thereof; or
further comprising at least one member selected from a manifold, an access port, and a flush port.

24. An encapsulation device comprising:
a plurality of containment tubes substantially parallel to each other, each said containment tube having a first access port at a first end thereof and a second access port at a second end thereof; and
a plurality of interconnection members fluidly connecting adjacent containment tubes.

25. The device of claim 24, wherein said interconnection members are positioned at an angle relative to said containment tubes.

26. The device of claim 25, wherein said interconnection members are positioned at an angle of zero degrees relative to said containment tubes.

27. The device of claim 24, further comprising a biological moiety housed within lumens of said containment tubes and interconnection members.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable encapsulation device comprising:
a plurality of containment tubes interconnected by connection members, each said containment tube having a first access port at a first end thereof and a second access port at a second end thereof, and
a removable manifold fluidly connected to said containment tubes at said first end,
wherein said containment tubes are substantially parallel to each other along a length of said device,
wherein said containment tubes comprise a porous composite material including:
an outer porous polymeric layer that permits ingrowth of vascular tissue; and
an inner polymeric layer disposed adjacent to said outer porous polymeric layer, said inner polymeric layer being impervious to cellular or vascular ingrowth,
wherein said connection members are periodically spaced along a length of said containment tubes a distance from each other, and
wherein said plurality of containment tubes are fluidly interconnected by said connection members.

2. The device of claim 1, further comprising a flush port and a tube fluidly connected to said removable manifold.

3. The device of claim 1, wherein said connection members are connected to said containment tubes at an angle greater than zero degrees and less than 90 degrees.

4. The device of claim 1, further comprising a woven textile, a non-woven textile, or a knit.

5. The device of claim 1, further comprising resealable caps affixed to each of said second access ports to seal said second end of said containment tubes.

6. The device of claim 1, wherein said containment tubes each comprise a lumen for reception and containment of a biological moiety or therapeutic device therein.

7. The device of claim 6, wherein the therapeutic device comprises a drug delivery device, a gene therapy device, a cell encapsulation device and combinations thereof.

8. The device of claim 7, wherein said biological moiety is a plurality of cells.

9. The device of claim 6, wherein the therapeutic device is removably sealed to said manifold, said manifold being fluidly connected to said containment tubes at said first end.

10. The device of claim 6, wherein the therapeutic device includes a grasping structure.

11. The device of claim 1, wherein said containment tubes have thereon a bio-absorbable material.

12. The device of claim 1, wherein said containment tubes are stacked upon one another in a z-direction.

13. The device of claim 1, wherein each of the plurality of containment tubes maintains a consistent cylindrical cross-section.

14. The device of claim 1, further comprising a bio-absorbable material in at least one of a solid form and a self-cohered web.

15. The device of claim 14, wherein the bio-absorbable material is formed as a solid structure with a tapered leading edge.

16. The device of claim 1, wherein said containment tubes comprise a shape memory material.

17. A cell encapsulation device comprising:
a plurality of containment tubes substantially parallel to each other along a length of the containment tubes, each said containment tube having a first access port at a first end thereof and a second access port at a second end thereof;
resealable caps sealably connected to each of said first access port of said containment tubes;
wherein the containment tubes are independently movable from each other down the length of the containment tubes, and
wherein said containment tubes comprise a porous composite material including:
an outer porous polymeric layer that permits ingrowth of vascular tissue; and
an inner polymeric layer disposed adjacent to said outer porous polymeric layer, said inner polymeric layer being impervious to cellular or vascular ingrowth.

18. The device of claim 17, comprising a manifold, wherein the containment tubes are fluidly connected by a flush port connected to the manifold via a tube.

19. The device of claim 18, wherein said manifold comprises at least two openings with hinged structures positioned between said at least two openings.

20. The device of claim 19, wherein each said containment tube is affixed to one of said openings in said manifold.

21. The device of claim 18, wherein said flush port and said tube lie in a same plane as said containment tubes.

22. The device of claim 17, wherein each said containment tube comprises a lumen for reception and containment of a biological moiety or therapeutic device therein.

23. The device of claim 22, wherein the therapeutic device comprises a drug delivery device, a gene therapy device, a cell encapsulation device and combinations thereof.

24. The device of claim 23, wherein said biological moiety is a plurality of cells.

25. The device of claim 22, wherein said biological moiety is a plurality of cells.

26. The device of claim 25, wherein the therapeutic device is removably sealed to a manifold.

27. The device of claim 26, wherein the therapeutic device includes a grasping structure.

28. The device of claim 17, wherein each of the plurality of containment tubes maintains a consistent cylindrical cross-section.

29. The device of claim 17, wherein said containment tubes have thereon a bio-absorbable material.

30. The device of claim 29, wherein said bio-absorbable material is in at least one of a solid form and a self-cohered web.

31. The device of claim 29, wherein the bio-absorbable material is a solid structure with a tapered leading edge.

32. The device of claim 17, wherein said containment tubes comprise a shape memory material.

33. The device of claim 17, comprising:
a manifold fluidly connected to each of the second access ports at the second ends; and
a flush port fluidly connected to the manifold via a tube.

34. The device of claim 17, wherein the containment tubes are connected by connection members spaced a distance from each other down a length of the containment tubes.

35. The device of claim 34, wherein the containment tubes are independently movable between the connection members.

36. The device of claim 34, wherein the containment tubes are fluidly interconnected by the connection members.

37. An encapsulation device comprising:
a plurality of containment tubes substantially parallel to each other, each of said containment tubes having a first access port at a first end thereof and a second access port at a second end thereof; and
a resealable first manifold fluidly connected to each of said first access ports,
a second manifold fluidly connected to each of said second access ports; and
a flush port fluidly connected to the second manifold,
wherein each of said containment tubes comprises a porous composite material including:
an outer porous polymeric layer that permits ingrowth of vascular tissue; and
an inner polymeric layer disposed adjacent to the outer porous polymeric layer, said inner polymeric layer being impervious to cellular or vascular ingrowth.

38. The device of claim 37, further comprising interconnection members, wherein a biological moiety is housed within lumens of each of said containment tubes and within each of said interconnection members.

39. The device of claim 38, wherein said biological moiety is a plurality of cells.

40. The device of claim 38, wherein said containment tubes and said interconnection members have thereon a bio-absorbable material.

41. The device of claim 40, wherein said bio-absorbable material is in at least one of a solid form and a self-cohered web.

42. The device of claim 40, wherein the bio-absorbable material is a solid structure with a tapered leading edge.

43. The device of claim 38, wherein each of the plurality of containment tubes and interconnection members maintain a consistent cylindrical cross-section.

44. The device of claim 37, wherein at least one containment tube of said plurality of containment tubes comprises a shape memory material.

45. The device of claim 37, further comprising a resealable cap to cover the flush port.

46. A cell encapsulation device comprising:
a plurality of containment tubes, each said containment tube having a first access port at a first end thereof and a second access port at a second end thereof;
a manifold located at a point a distance between said first ends and said second ends of said containment tubes, said manifold being fluidly connected to each of said containment tubes at said point;
a divider element located within said manifold to form a first portion and second portion of each said containment tube; and
a flush port fluidly connected to said manifold by a tube,
wherein said flush port is sealably connected to said containment tubes, and
wherein said point is centrally located between said first ends and said second ends.

47. An encapsulation device comprising:
a plurality of containment tubes substantially parallel to each other, each of said containment tubes having a first access port at a first end thereof and a second access port at a second end thereof;
a first removable manifold fluidly connected to each of the first access ports;
a second removable manifold fluidly connected to each of the second access ports;
a first flush port fluidly connected to the first manifold; and
a second flush port fluidly connected to the second manifold,
wherein each said containment tube comprises a porous composite material including:
an outer porous polymeric layer that permits ingrowth of vascular tissue; and
an inner polymeric layer disposed adjacent to said outer porous polymeric layer, said inner polymeric layer being impervious to cellular or vascular ingrowth.

* * * * *